(12) United States Patent
Frank-Foltyn et al.

(10) Patent No.: US 9,771,359 B1
(45) Date of Patent: Sep. 26, 2017

(54) SUBSTITUTED OXAZOLE- AND THIAZOLE-BASED CARBOXAMIDE AND UREA DERIVATIVES AS VANILLOID RECEPTOR LIGANDS II

(71) Applicant: MEDIFRON DBT INC., Seoul (KR)

(72) Inventors: Robert Frank-Foltyn, Beiseförth (DE); Christopher Habermann, Aachen (DE); Gregor Bahrenberg, Monschau-Konzen (DE); Bernhard Lesch, Aachen (DE); Nils Damann, Hürth (DE); Klaus Schiene, Jüchen (DE); Hannelore Stockhausen, Hürtgenwald (DE); Thomas Christoph, Aachen (DE); Sven Frormann, Aachen (DE); Derek Saunders, Aachen (DE); Jeewoo Lee, Seoul (KR)

(73) Assignee: Medifron DBT Inc., Seoul (KR)

( * ) Notice: Subject to any disclaimer, the term of this patent is extended or adjusted under 35 U.S.C. 154(b) by 0 days.

(21) Appl. No.: 15/603,280

(22) Filed: May 23, 2017

Related U.S. Application Data

(63) Continuation of application No. PCT/EP2015/002362, filed on Nov. 24, 2015.

(30) Foreign Application Priority Data

Nov. 24, 2014 (EP) .................................... 14003949

(51) Int. Cl.
| | |
|---|---|
| C07D 417/14 | (2006.01) |
| C07D 277/28 | (2006.01) |
| C07D 263/32 | (2006.01) |
| C07D 413/12 | (2006.01) |
| C07D 417/12 | (2006.01) |
| C07D 413/14 | (2006.01) |
| A61K 31/4439 | (2006.01) |
| A61K 31/421 | (2006.01) |
| A61K 31/426 | (2006.01) |
| A61K 31/506 | (2006.01) |

(52) U.S. Cl.
CPC ......... *C07D 417/14* (2013.01); *C07D 263/32* (2013.01); *C07D 277/28* (2013.01); *C07D 413/12* (2013.01); *C07D 413/14* (2013.01); *C07D 417/12* (2013.01)

(58) Field of Classification Search
None
See application file for complete search history.

(56) References Cited

U.S. PATENT DOCUMENTS

| 2013/0079373 A1 | 3/2013 | Frank et al. |
| 2013/0079377 A1 | 3/2013 | Frank et al. |

FOREIGN PATENT DOCUMENTS

| WO | 2013013815 | 1/2013 | |
| WO | 2013013817 | 1/2013 | |
| WO | 2013068462 | 3/2013 | |
| WO | 2013068464 | 5/2013 | |
| WO | 2013068467 | 5/2013 | |
| WO | WO 2014110298 A1 * | 7/2014 | ........... C07D 403/12 |

OTHER PUBLICATIONS

Search Report, dated Mar. 3, 2016, corresponding to International Application No. PCT/EP2015/002362 (filed Nov. 24, 2015), a related application, 2 pp.

* cited by examiner

*Primary Examiner* — Michael Barker
(74) *Attorney, Agent, or Firm* — Lathrop & Gage LLP

(57) ABSTRACT

The invention relates to oxazole and thiazole-based carboxamide and urea derivatives as vanilloid receptor ligands, to pharmaceutical compositions containing these compounds and also to these compounds for use in the treatment and/or prophylaxis of pain and further diseases and/or disorders.

19 Claims, No Drawings

SUBSTITUTED OXAZOLE- AND THIAZOLE-BASED CARBOXAMIDE AND UREA DERIVATIVES AS VANILLOID RECEPTOR LIGANDS II

CROSS-REFERENCE TO RELATED APPLICATIONS

This application is a continuation of PCT/EP2015/002362, filed Nov. 24, 2015, which claims the benefit of EP Application No. 14003949.6, filed Nov. 24, 2014. Both of these applications are hereby incorporated by reference in their entireties.

FIELD OF THE INVENTION

The invention relates to substituted oxazole and thiazole-based carboxamide and urea derivatives as vanilloid receptor ligands, to pharmaceutical compositions containing these compounds and also to these compounds for use in the treatment and/or prophylaxis of pain and further diseases and/or disorders.

BACKGROUND OF THE INVENTION

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain. This receptor is stimulated inter alia by vanilloids such as capsaicin, heat and protons and plays a central role in the formation of pain. In addition, it is important for a large number of further physiological and patho-physiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and urinary incontinence.

There is a demand for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example. A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions or no interactions at all, of pharmaceutical compositions are to be expected.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by vanilloid receptors 1 (VR1/TRPV1 receptors).

This object is achieved by the subject matter described herein.

It has surprisingly been found that the substituted compounds of general formula (I), as given below, display outstanding affinity to the subtype 1 vanilloid receptor (VR1/TRPV1 receptor) and are therefore particularly suitable for the prophylaxis and/or treatment of disorders or diseases which are at least partially mediated by vanilloid receptors 1 (VR1/TRPV1).

Particularly suitable are substituted compounds of general formula (I), as given below, that in addition to their activity with regard to the VR1-receptor show one or more additional advantageous properties, for example, suitable potency, suitable efficacy, no increase in body temperature and/or heat pain threshold; appropriate solubility in biologically relevant media such as aqueous media, in particular in aqueous media at a physiologically acceptable pH value, such as in buffer systems, for instance in phosphate buffer systems; suitable metabolic stability and diversity (e.g. sufficient stability towards the oxidative capabilities of hepatic enzymes such as cytochrome P450 (CYP) enzymes and sufficient diversity with regard to the metabolic elimination via these enzymes); and the like.

In a first aspect of the present invention, the present invention relates to a substituted compound of general formula (I),

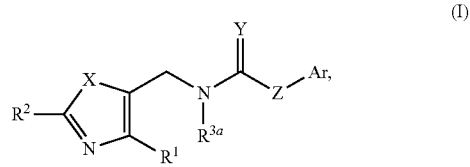

(I)

wherein
X represents O or S;
Y represents O, S or N—CN;
Z represents $N(R^{3b})$ or $C(R^{4a}R^{4b})$;
$R^1$ represents aryl or heteroaryl,
   wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, $C_{1-4}$-alkylS(O), hydroxy-$C_{1-4}$-alkylS(O), halo-$C_{1-4}$-alkylS(O), cyano-$C_{1-4}$-alkylS(O), $C_{1-4}$-alkoxy-$C_{1-4}$-alkylS(O), $C_{1-4}$-alkylS(O)$_2$, hydroxy-$C_{1-4}$-alkylS(O)$_2$, halo-$C_{1-4}$-alkylS(O)$_2$, cyano-$C_{1-4}$-alkylS(O)$_2$, $C_{1-4}$-alkoxy-$C_{1-4}$-alkylS(O)$_2$, $H_2N$, ($C_{1-4}$-alkyl)(H)N, (hydroxy-$C_{1-4}$-alkyl)(H)N, (halo-$C_{1-4}$-alkyl)(H)N, (cyano-$C_{1-4}$-alkyl)(H)N, ($C_{1-4}$-alkoxy-$C_{1-4}$-alkyl)(H)N, ($C_{3-6}$-cycloalkyl)(H)N, ($C_{3-7}$-heterocycloalkyl)(H)N, ($C_{1-4}$-alkyl)$_2$N, (hydroxy-$C_{1-4}$-alkyl)($C_{1-4}$-alkyl)N, (halo-$C_{1-4}$-alkyl)($C_{1-4}$-alkyl)N, (cyano-$C_{1-4}$-alkyl)($C_{1-4}$-alkyl)N, ($C_{1-4}$-alkoxy-$C_{1-4}$-alkyl)($C_{1-4}$-alkyl)N, ($C_{3-6}$-cycloalkyl)($C_{1-4}$-alkyl)N, ($C_{3-7}$-heterocycloalkyl)($C_{1-4}$-alkyl)N, (hydroxy-$C_{1-4}$-alkyl)$_2$N, ($C_{3-6}$-cycloalkyl)(hydroxy-$C_1$-4-alkyl)N and ($C_{3-7}$-heterocycloalkyl)(hydroxy-$C_{1-4}$-alkyl)N, $R^2$ represents $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, $C_{3-6}$-cycloalkyl or ($C_{3-6}$-cycloalkyl)-$C_{1-4}$-alkyl;

$R^{3a}$ and $R^{3b}$ each independently represent H, $C_{1-4}$-alkyl, hydroxy-$C_{1-4}$-alkyl, halo-$C_{1-4}$-alkyl, cyano-$C_{1-4}$-alkyl or $C_{1-4}$-alkoxy-$C_{1-4}$-alkyl;

$R^{4a}$ and $R^{4b}$ each independently represent H, F, Cl, CN, $C_{1-4}$-alkyl, hydroxy-$C_{1-4}$-alkyl, halo-$C_{1-4}$-alkyl, cyano-$C_{1-4}$-alkyl or $C_{1-4}$-alkoxy-$C_{1-4}$-alkyl;

or $R^{4a}$ and $R^{4b}$ together with the carbon atom connecting them form a $C_{3-6}$-cycloalkyl or a $C_{3-7}$-heterocycloalkyl;

Ar represents aryl or heteroaryl, wherein said aryl or heteroaryl may be condensed with an aromatic or aliphatic ring to form a bicycle, and wherein said aryl or heteroaryl and said condensed aromatic or aliphatic ring each independently may be unsubstituted or mono- or independently polysubstituted by one or more substituents, selected from the group consisting of F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, hydroxy-$C_{1-4}$-alkoxy-$C_{1-4}$-alkyl, $C_{1-4}$-alkylS(O), hydroxy-$C_{1-4}$-alkylS(O), halo-$C_{1-4}$-alkylS(O), cyano-$C_{1-4}$-alkylS(O), $C_{1-4}$-alkoxy-$C_{1-4}$-alkylS(O), $C_{1-4}$-alkylS(O)$_2$, hydroxy-$C_{1-4}$-alkylS(O)$_2$, halo-$C_{1-4}$-alkylS(O)$_2$, cyano-$C_{1-4}$-alkylS(O)$_2$, $C_{1-4}$-alkoxy-$C_{1-4}$-alkylS(O)$_2$, $C_{1-4}$-alkylS(O)$C_{1-4}$-alkyl, hydroxy-$C_{1-4}$-alkylS(O)$C_{1-4}$-alkyl, $C_{1-4}$-alkylS(O)$_2C_{1-4}$-alkyl, hydroxy-$C_{1-4}$-alkylS(O)$_2C_{1-4}$-alkyl, $H_2N$, ($C_{1-4}$-alkyl)(H)N, (hydroxy-$C_{1-4}$-alkyl)(H)N, (halo-$C_{1-4}$-alkyl)(H)N, (cyano-$C_{1-4}$-alkyl)(H)N, ($C_{1-4}$-alkoxy-$C_{1-4}$-alkyl)(H)N, ($C_{3-6}$-cycloalkyl)(H)N, ($C_{3-7}$-heterocycloalkyl)(H)N, ($C_{1-4}$-alkyl)$_2$N, (hydroxy-$C_{1-4}$-alkyl)($C_{1-4}$-alkyl)N, (halo-$C_{1-4}$-alkyl)($C_{1-4}$-alkyl)N, (cyano-$C_{1-4}$-alkyl)($C_{1-4}$-alkyl)N, ($C_{1-4}$-alkoxy-$C_{1-4}$-alkyl)($C_{1-4}$-alkyl)N, ($C_{3-6}$-cycloalkyl)($C_{1-4}$-alkyl)N, ($C_{3-7}$-heterocycloalkyl)($C_{1-4}$-alkyl)N, (hydroxy-$C_{1-4}$-alkyl)$_2$N, ($C_{3-6}$-cycloalkyl)(hydroxy-$C_{1-4}$-alkyl)N, ($C_{3-7}$-heterocycloalkyl)(hydroxy-$C_{1-4}$-alkyl)N, (H)$_2NC_{1-4}$-alkyl, [($C_{1-4}$-alkyl)(H)N]($C_{1-4}$-alkyl), [(hydroxy-$C_{1-4}$-alkyl)(H)N]($C_{1-4}$-alkyl), [(halo-$C_{1-4}$-alkyl)(H)N]($C_{1-4}$-alkyl), [(cyano-$C_{1-4}$-alkyl)(H)]($C_{1-4}$-alkyl), [($C_{1-4}$-alkoxy-$C_{1-4}$-alkyl)(H)N]($C_{1-4}$-alkyl), [($C_{3-6}$-cycloalkyl)(H)N]($C_{1-4}$-alkyl), [($C_{3-7}$-heterocycloalkyl)(H)N]($C_{1-4}$-alkyl), [($C_{1-4}$-alkyl)$_2$N]($C_{1-4}$-alkyl), [(hydroxy-$C_{1-4}$-alkyl)($C_{1-4}$-alkyl)N]($C_{1-4}$-alkyl), [(halo-$C_{1-4}$-alkyl)($C_{1-4}$-alkyl)N]($C_{1-4}$-alkyl), [(cyano-$C_{1-4}$-alkyl)($C_{1-4}$-alkyl)N]($C_{1-4}$-alkyl), [($C_{1-4}$-alkoxy-$C_{1-4}$-alkyl)($C_{1-4}$-alkyl)N]($C_{1-4}$-alkyl), [($C_{3-6}$-cycloalkyl)($C_{1-4}$-alkyl)N]($C_1$-4-alkyl), [($C_{3-7}$-heterocycloalkyl)($C_{1-4}$-alkyl)N]($C_{1-4}$-alkyl), [(hydroxy-$C_{1-4}$-alkyl)$_2$N]($C_{1-4}$-alkyl), [($C_{3-6}$-cycloalkyl)(hydroxy-$C_{1-4}$-alkyl)N]($C_{1-4}$-alkyl), [($C_{3-7}$-heterocycloalkyl)(hydroxy-$C_{1-4}$-alkyl)N]($C_{1-4}$-alkyl), $H_2NC(O)$, ($C_{1-4}$-alkyl)(H)NC(O), (hydroxy-$C_{1-4}$-alkyl)(H)NC(O), (halo-$C_{1-4}$-alkyl)(H)NC(O), (cyano-$C_{1-4}$-alkyl)(H)NC(O), ($C_{1-4}$-alkoxy-$C_{1-4}$-alkyl)(H)NC(O), ($C_{3-6}$-cyclo-alkyl)(H)NC(O), ($C_{3-7}$-heterocycloalkyl)(H)NC(O), ($C_{1-4}$-alkyl)$_2$NC(O), (hydroxy-$C_{1-4}$-alkyl)($C_{1-4}$-alkyl)NC(O), (halo-$C_{1-4}$-alkyl)($C_{1-4}$-alkyl)NC(O), (cyano-$C_{1-4}$-alkyl)($C_{1-4}$-alkyl)NC(O), ($C_{1-4}$-alkoxy-$C_{1-4}$-alkyl)($C_{1-4}$-alkyl)NC(O), ($C_{3-6}$-cycloalkyl)($C_{1-4}$-alkyl)NC(O), ($C_{3-7}$-heterocycloalkyl)($C_{1-4}$-alkyl)NC(O), (hydroxy-$C_{1-4}$-alkyl)$_2$NC(O), ($C_{3-6}$-cycloalkyl)(hydroxy-$C_{1-4}$-alkyl)NC(O), ($C_{3-7}$-heterocycloalkyl)(hydroxy-$C_{1-4}$-alkyl)NC(O), $H_2NS(O)_2$, ($C_{1-4}$-alkyl)(H)NS(O)$_2$, (hydroxy-$C_{1-4}$-alkyl)(H)NS(O)$_2$, (halo-$C_{1-4}$-alkyl)(H)NS(O)$_2$, (cyano-$C_{1-4}$-alkyl)(H)NS(O)$_2$, ($C_{1-4}$-alkoxy-$C_{1-4}$-alkyl)(H)—NS(O)$_2$, ($C_{3-6}$-cycloalkyl)(H)NS(O)$_2$, ($C_{3-7}$-heterocycloalkyl)(H)NS(O)$_2$, ($C_{1-4}$-alkyl)$_2$NS (O)$_2$, (hydroxy-$C_{1-4}$-alkyl)($C_{1-4}$-alkyl)NS(O)$_2$, (halo-$C_{1-4}$-alkyl)($C_{1-4}$-alkyl)NS(O)$_2$, (cyano-$C_{1-4}$-alkyl)($C_{1-4}$-alkyl)NS(O)$_2$, ($C_{1-4}$-alkoxy-$C_{1-4}$-alkyl)($C_{1-4}$-alkyl)NS(O)$_2$, ($C_{3-6}$-cycloalkyl)($C_{1-4}$-alkyl)NS(O)$_2$, ($C_{3-7}$-hetero-cycloalkyl)($C_{1-4}$-alkyl)NS(O)$_2$, (hydroxy-$C_{1-4}$-alkyl)$_2$NS(O)$_2$, ($C_{3-6}$-cycloalkyl)-(hydroxy-$C_{1-4}$-alkyl)NS(O)$_2$, ($C_{3-7}$-heterocycloalkyl)(hydroxy-$C_{1-4}$-alkyl)-NS(O)$_2$, $H_2NS(O)_2N(H)C_{1-4}$-alkyl, ($C_{1-4}$-alkyl)(H)NS(O)$_2N(H)C_{1-4}$-alkyl, (hydroxy-$C_{1-4}$-alkyl)(H)NS(O)$_2N(H)C_{1-4}$-alkyl, ($C_{1-4}$-alkyl)$_2$NS(O)$_2N(H)C_{1-4}$-alkyl, ($C_{1-4}$-alkyl)S(O)$_2N(H)C_{1-4}$-alkyl, (hydroxy-$C_{1-4}$-alkyl)S(O)$_2N(H)C_{1-4}$-alkyl, $C_{3-6}$-cycloalkyl, ($C_{3-6}$-cycloalkyl)-$C_{1-4}$-alkyl, ($C_{3-6}$-cycloalkyl)-$C_{1-4}$-alkoxy, $C_{3-7}$-heterocycloalkyl, ($C_{3-7}$-heterocycloalkyl)-$C_{1-4}$-alkyl, ($C_{3-7}$-heterocycloalkyl)-$C_{1-4}$-alkoxy, wherein said $C_{3-6}$-cycloalkyl or $C_{3-7}$-heterocycloalkyl may be unsubstituted or mono- or independently polysubstituted by one or more substituents, selected from H, F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

aryl, heteroaryl, (aryl)$C_{1-4}$-alkyl or (heteroaryl)$C_{1-4}$-alkyl, wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

optionally in the form of a single stereoisomer or a mixture of stereoisomers, in the form of the free compound and/or a physiologically acceptable salt or a solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base. A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals. A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

Unless otherwise specified, the term "$C_1$-$C_4$-alkyl" ("($C_1$-$C_4$)-alkyl") is understood to mean branched and unbranched alkyl groups consisting of 1 to 4 carbon atoms which is optionally mono- or polysubstituted. Examples of $C_1$-$C_4$-alkyl are methyl, ethyl, n-propyl, 1-methylethyl (2-propyl; isopropyl), n-butyl, 1-methylpropyl (2-butyl), 2-methylpropyl, 1,1-dimethylethyl (2-(2-methyl)propyl; tert-butyl). $C_1$-$C_3$-alkyl are particularly preferred, in particular methyl, ethyl n-propyl or iso-propyl. Unless otherwise stated, the definitions of propyl and butyl encompass all possible isomeric forms of the individual radicals.

Unless otherwise specified, the term "$C_1$-$C_4$-alkoxy" is understood to mean branched and unbranched alkyl groups consisting of 1 to 4 carbon atoms which are linked to the subordinate structure residue via an oxygene atom and which is optionally mono- or polysubstituted. Examples of $C_1$-$C_4$-alkoxy are $OCH_3$, $OCH_2CH_3$, $O(CH_2)_2CH_3$, $O(CH_2)_3CH_3$, $OCH(CH_3)_2$, $OCH_2CH(CH_3)_2$, $OCH(CH_3)(CH_2CH_3)$, $OC(CH_3)_3$—$C_1$-$C_3$-alkoxy are particularly preferred, in particular $OCH_3$, $OCH_2CH_3$ or $OCH(CH_3)_2$.

Unless otherwise specified, a "halo-$C_{1-4}$-alkyl" is understood to be a $C_{1-4}$-alkyl in which at least one hydrogen is exchanged for a halogen atom, preferably F, Cl or Br, particularly preferably F. The halo-$C_{1-4}$-alkyl can be branched or unbranched and optionally mono- or polysubstituted. Preferred halo-$C_{1-4}$-alkyl are $CHF_2$, $CH_2F$, $CF_3$, $CH_2CH_2F$, $CH_2CHF_2$, $CH_2CF_3$. Halo-$C_1$-$C_3$-alkyl are more preferred, in particular $CHF_2$, $CH_2F$, $CF_3$, $CH_2CH_2F$, $CH_2CHF_2$ and $CH_2CF_3$. Unless otherwise specified, a "halo-$C_{1-4}$-alkoxy" is understood to be a $C_{1-4}$-alkoxy in which at least one hydrogen is exchanged for a halogen atom, preferably F, Cl or Br, particularly preferably F. The halo-$C_{1-4}$-alkoxy can be branched or unbranched and optionally mono- or polysubstituted. Preferred halo-$C_{1-4}$-alkoxy are $OCHF_2$, $OCH_2F$, $OCF_3$, $OCH_2CFH_2$, $OCH_2CF_2H$, $OCH_2CF_3$. Halo-$C_{1-3}$-alkoxy are preferred, in particular $OCHF_2$, $OCH_2F$, $OCF_3$, $OCH_2CFH_2$, $OCH_2CF_2H$, $OCH_2CF_3$.

Unless otherwise specified, a "hydroxy-$C_{1-4}$-alkyl" radical is to be a $C_{1-4}$-alkyl in which at least one hydrogen is exchanged for a hydroxyl group. The hydroxy-$C_{1-4}$-alkyl can be branched or unbranched and optionally mono- or polysubstituted. hydroxy-$C_{1-3}$-alkyl are preferred, in particular $CH_2OH$, $CH_2CH_2OH$ and $CH_2CH_2CH_2OH$. Unless otherwise specified, a "cyano-$C_{1-4}$-alkyl" is understood to be a $C_{1-4}$-alkyl in which at least one hydrogen is exchanged for a cyano group. The cyano-$C_{1-4}$-alkyl can be branched or unbranched and optionally mono- or polysubstituted. Cyano-$C_{1-3}$-alkyl are preferred, in particular $CH_2CN$, $CH_2CH_2CN$ and $CH_2CH_2CH_2CN$. Unless otherwise specified, a "$C_{1-4}$-alkoxy-$C_{1-4}$-alkyl" is understood to be a $C_{1-4}$-alkyl in which at least one hydrogen is exchanged for $C_{1-4}$-alkoxy. The $C_{1-4}$-alkoxy-$C_{1-4}$-alkyl can be branched or unbranched and optionally mono- or polysubstituted. $C_{1-4}$-alkoxy-$C_{1-3}$-alkyl are preferred, in particular $CH_2OCH_3$, $CH_2CH_2OCH_3$, $CH_2CH_2CH_2OCH_3$, $CH_2OCH_2CH_3$ and $CH_2OCH(CH_3)_2$.

Unless otherwise specified, a "hydroxy-$C_{1-4}$-alkoxy", a "cyano-$C_{1-4}$-alkoxy" and a "$C_{1-4}$-alkoxy-$C_{1-4}$-alkoxy" each is understood to be a $C_{1-4}$-alkoxy in which at least one hydrogen is exchanged for a hydroxyl, a cyano or a $C_{1-4}$-alkoxy. The hydroxy-$C_{1-4}$-alkoxy, cyano-$C_{1-4}$-alkoxy and $C_{1-4}$-alkoxy-$C_{1-4}$-alkoxy can be branched or unbranched and optionally mono- or polysubstituted. Preferred hydroxy-$C_{1-4}$-alkoxy are $OCH_2CH_2OH$ and $OCH_2CH_2CH_2OH$. Preferred cyano-$C_{1-4}$-alkoxy are $OCH_2CN$, $OCH_2CH_2CN$ and $OCH_2CH_2CH_2CN$. Preferred $C_{1-4}$-alkoxy-$C_{1-4}$-alkoxy are $OCH_2CH_2OCH_3$, $OCH_2CH_2CH_2OCH_3$, $OCH(CH_3)OCH_3$, $OCH_2CH_2OCH_2CH_3$ and $OCH_2CH_2OCH(CH_3)_2$.

The term "$C_{3-6}$-cycloalkyl" means for the purposes of this invention cyclic aliphatic hydrocarbons containing 3, 4, 5 or 6 carbon atoms, wherein the hydrocarbons in each case can be unsubstituted or mono- or polysubstituted. The $C_{3-6}$-cycloalkyl can be bound to the respective superordinate general structure via any desired and possible ring member of the $C_{3-6}$-cycloalkyl. The $C_{3-6}$-cycloalkyl can also be condensed with further saturated, (partially) unsaturated, (hetero)cyclic, aromatic or heteroaromatic ring systems, i.e. with cycloalkyl, heterocycloalkyl, aryl or heteroaryl residues. Preferred $C_{3-6}$-cycloalkyls are selected from the group consisting of cyclopropyl, cyclobutyl, cyclopentyl, cyclohexyl, in particular cyclopropyl.

The terms "$C_{3-7}$-heterocycloalkyl" mean for the purposes of this invention heterocycloaliphatic saturated or unsaturated (but not aromatic) residues having 3 to 7, i.e. 3, 4, 5, 6 or 7 ring members, in which in each case at least one, if appropriate also two, three or four carbon atoms are replaced by a heteroatom or a heteroatom group each selected independently of one another from the group consisting of O, S, S(=O), S(=O)$_2$, N, NH and N($C_{1-6}$-alkyl) such as N($CH_3$), wherein the ring members can be unsubstituted or mono- or polysubstituted. The $C_{3-7}$-heterocycloalkyl can also be condensed with further saturated, (partially) unsaturated, (hetero)cyclic, aromatic or heteroaromatic ring systems, i.e. with cycloalkyl, heterocycloalkyl, aryl or heteroaryl residues. The $C_{3-7}$-heterocycloalkyl may be bound to the superordinate general structure via any possible ring member of the heterocycloalkyl if not indicated otherwise.

The term "aryl" for the purpose of this invention represents phenyl, 1-naphthyl or 2-naphthyl, wherein the aryl can be unsubstituted or mono- or polysubstituted.

The term "heteroaryl" for the purpose of this invention represents a cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. It is preferable for the heteroaryl residue to be selected from the group consisting of benzofuranyl, benzoimidazolyl, benzothienyl, benzothiadiazolyl, benzothiazolyl, benzotriazolyl, benzo-oxazolyl, benzooxadiazolyl, quinazolinyl, quinoxalinyl, carbazolyl, quinolinyl, dibenzo-furanyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

For the purpose of this invention, the term "said aryl or heteroaryl may be condensed with an aromatic or aliphatic ring to form a bicycle" is understood as meaning a bicyclic ring system wherein at least one ring is aromatic and wherein the link to the superordinate general structure is via an atom of aryl or heteroaryl. The bicyclic ring system may be fully aromatic (condensation of aryl or heteroaryl with an aromatic ring, so an aryl or heteroaryl moiety) or partially aromatic (condensation of aryl or heteroaryl with a non-aromatic ring, so a cycloalkyl or heterocycloalkyl moiety).

In connection with non-aromatic moieties such as "alkyl", "alkoxy", "cycloalkyl" and "heterocycloalkyl", in the context of this invention the term "substituted" is understood as meaning replacement of a hydrogen radical by a substituent selected from the group consisting of =O, OH, CN, F, Cl, Br, I, SH, $(C_1\text{-}C_4)$-alkyl, $(C_2\text{-}C_4)$-alkenyl, $(C_2\text{-}C_4)$-alkinyl, $(C_1\text{-}C_4)$-hydroxyalkyl, $(C_1\text{-}C_4)$-cyanoalkyl, $(C_1\text{-}C_4)$-alkoxy, $(C_1\text{-}C_4)$-thioalkyl, $(C_1\text{-}C_4)$-haloalkyl, $(C_1\text{-}C_4)$-thiohaloalkyl, $(C_1\text{-}C_4)$-haloalkoxy, $(C_1\text{-}C_4)$-alkyl-S—$(C_1\text{-}C_4)$-alkyl, $(C_3\text{-}C_6)$-cycloalkyl, $(C_3\text{-}C_6)$-cycloalkyl-$(C_1\text{-}C_3)$-alkyl, $(C_3\text{-}C_7)$-heterocycloalkyl, $NH_2$, $NH(C_1\text{-}C_4)$-alkyl, $N((C_1\text{-}C_4)\text{-alkyl})_2$, $NHCO(C_1\text{-}C_4)$-alkyl, $NHCOO(C_1\text{-}C_4)$-alkyl, $NH\text{—}C(O)NH_2$, $NHCONH(C_1\text{-}C_4)$-alkyl, $NHCON((C_1\text{-}C_4)\text{-alkyl})_2$, $NH((C_1\text{-}C_4)\text{-alkyl})COO(C_1\text{-}C_4)$-alkyl, $NH((C_1\text{-}C_4)\text{-alkyl})\text{-}CONH_2$, $NH((C_1\text{-}C_4)\text{-alkyl})CONH(C_1\text{-}C_4)$-alkyl, $NH((C_1\text{-}C_4)\text{-alkyl})CON((C_1\text{-}C_4)\text{-alkyl})_2$, $NHS(O)_2OH$, $NHS(O)_2(C_1\text{-}C_4)$-alkyl, $NHS(O)_2O(C_1\text{-}C_4)$-alkyl, $NHS(O)_2NH_2$, $NHS(O)_2NH(C_1\text{-}C_4)$-alkyl, $NHS(O)_2N((C_1\text{-}C_4)\text{-alkyl})_2$, $NH((C_1\text{-}C_4)\text{-alkyl})\text{-}S(O)_2OH$, $NH((C_1\text{-}C_4)\text{-alkyl})S(O)_2(C_1\text{-}C_4)$-alkyl, $NH((C_1\text{-}C_4)\text{-alkyl})S(O)_2O(C_1\text{-}C_4)$-alkyl, $NH((C_1\text{-}C_4)\text{-alkyl})S(O)_2NH_2$, $NH((C_1\text{-}C_4)\text{-alkyl})S(O)_2NH(C_1\text{-}C_4)$-alkyl, $CO_2H$, $CO(C_1\text{-}C_4)$-alkyl, $COO(C_1\text{-}C_4)$-alkyl, $OCO(C_1\text{-}C_4)$-alkyl, $OCOO(C_1\text{-}C_4)$-alkyl, $CONH_2$, $CONH(C_1\text{-}C_4)$-alkyl, $CON((C_1\text{-}C_4)\text{-alkyl})_2$, $OCONH(C_1\text{-}C_4)$-alkyl, $OCON((C_1\text{-}C_4)\text{-alkyl})_2$, $OS(O)_2(C_1\text{-}C_4)$-alkyl, $OS(O)_2OH$, $OS(O)_2(C_1\text{-}C_4)$-alkyl, $OS(O)_2NH_2$, $OS(O)_2NH(C_1\text{-}C_4)$-alkyl, $OS(O)_2N((C_1\text{-}C_4)\text{-alkyl})_2$, $S(O)(C_1\text{-}C_4)$-alkyl, $S(O)_2(C_1\text{-}C_4)$-alkyl, $S(O)_2OH$, $S(O)_2O(C_1\text{-}C_4)$-alkyl, $S(O)_2NH_2$, $S(O)_2NH(C_1\text{-}C_4)$-alkyl, and $S(O)_2N((C_1\text{-}C_4)\text{-alkyl})_2$. If a moiety is substituted with more than 1 substituent, e.g. by 2, 3, 4, or 5 substituents, these substituents may be present either on different or on the same atoms, e.g. as in the case of $CF_3$ or $CH_2CF_3$, or at different places, as in the case of $CH(Cl)CHCl_2$. Substitution with more than 1 substituent may include identical or different substituents, such as, for example, in the case of $CH(OH)CHCl_2$. Preferably, the substituents may be selected from the group consisting of F, Cl, Br, $CF_3$, $CHF_2$, $CH_2F$, $OCF_3$, OH, CN, $(C_1\text{-}C_4)$-alkyl, $(C_1\text{-}C_4)$-hydroxyalkyl, $(C_1\text{-}C_4)$-alkoxy, $(C_3\text{-}C_6)$-cycloalkyl, $NH_2$, $NH(C_1\text{-}C_4)$-alkyl, $N((C_1\text{-}C_4)\text{-alkyl})_2$, $NHCO(C_1\text{-}C_4)$-alkyl, $NHCONH(C_1\text{-}C_4)$-alkyl, $NHCON((C_1\text{-}C_4)\text{-alkyl})_2$, $NHS(O)_2(C_1\text{-}C_4)$-alkyl, $CONH_2$, $CONH(C_1\text{-}C_4)$-alkyl, $CON((C_1\text{-}C_4)\text{-alkyl})_2$, $S(O)(C_1\text{-}C_4)$-alkyl and $S(O)_2(C_1\text{-}C_4)$-alkyl.

In connection with aromatic moieties such as "aryl" and "heteroaryl", in the context of this invention the term "substituted" is understood as meaning replacement of a hydrogen radical by a substituent selected from the group consisting of OH, halogen, CN, SH, nitro, $(C_1\text{-}C_4)$-alkyl, $(C_2\text{-}C_4)$-alkenyl, $(C_2\text{-}C_4)$-alkinyl, $(C_1\text{-}C_4)$-hydroxyalkyl, $(C_1\text{-}C_4)$-cyanoalkyl, $(C_1\text{-}C_4)$-alkoxy, $(C_1\text{-}C_4)$-thioalkyl, $(C_1\text{-}C_4)$-haloalkyl, $(C_1\text{-}C_4)$-thiohaloalkyl, $(C_1\text{-}C_4)$-haloalkoxy, $(C_1\text{-}C_4)$-alkyl-S—$(C_1\text{-}C_4)$-alkyl, $(C_3\text{-}C_6)$-cycloalkyl, $(C_3\text{-}C_6)$-cycloalkyl-$(C_1\text{-}C_3)$-alkyl, $(C_3\text{-}C_7)$-heterocycloalkyl, $NH_2$, $NH(C_1\text{-}C_4)$-alkyl, $N((C_1\text{-}C_4)\text{-alkyl})_2$, $NHCO(C_1\text{-}C_4)$-alkyl, $NHCOO(C_1\text{-}C_4)$-alkyl, $NHC(O)NH_2$, $NHCONH(C_1\text{-}C_4)$-alkyl, $NHCON((C_1\text{-}C_4)\text{-alkyl})_2$, $NH((C_1\text{-}C_4)\text{-alkyl})COO(C_1\text{-}C_4)$-alkyl, $NH((C_1\text{-}C_4)\text{-alkyl})CONH_2$, $NH((C_1\text{-}C_4)\text{-alkyl})CONH(C_1\text{-}C_4)$-alkyl, $NH((C_1\text{-}C_4)\text{-alkyl})CON((C_1\text{-}C_4)\text{-alkyl})_2$, $NHS(O)_2OH$, $NHS(O)_2(C_1\text{-}C_4)$-alkyl, $NHS(O)_2O(C_1\text{-}C_4)$-alkyl, $NH\text{—}S(O)_2NH_2$, $NHS(O)_2NH(C_1\text{-}C_4)$-alkyl, $NH\text{—}S(O)_2N((C_1\text{-}C_4)\text{-alkyl})_2$, $NH((C_1\text{-}C_4)\text{-alkyl})\text{-}S(O)_2OH$, $NH((C_1\text{-}C_4)\text{-alkyl})S(O)_2(C_1\text{-}C_4)$-alkyl, $NH((C_1\text{-}C_4)\text{-alkyl})\text{-}S(O)_2O(C_1\text{-}C_4)$-alkyl, $NH((C_1\text{-}C_4)\text{-alkyl})S(O)_2NH_2$, $NH((C_1\text{-}C_4)\text{-alkyl})S(O)_2NH(C_1\text{-}C_4)$-alkyl, $CO_2H$, $CO(C_1\text{-}C_4)$-alkyl, $COO(C_1\text{-}C_4)$-alkyl, $OCO(C_1\text{-}C_4)$-alkyl, $OCOO(C_1\text{-}C_4)$-alkyl, $CONH_2$, $CONH(C_1\text{-}C_4)$-alkyl, $CON((C_1\text{-}C_4)\text{-alkyl})_2$, $OCONH(C_1\text{-}C_4)$-alkyl, $OCON((C_1\text{-}C_4)\text{-alkyl})_2$, $OS(O)_2(C_1\text{-}C_4)$-alkyl, $OS(O)_2OH$, $OS(O)_2(C_1\text{-}C_4)$-alkoxy, $OS(O)_2NH_2$, $OS(O)_2NH(C_1\text{-}C_4)$-alkyl, $OS(O)_2\text{—}N((C_1\text{-}C_4)\text{-alkyl})_2$, $S(O)(C_1\text{-}C_4)$-alkyl, $S(O)_2(C_1\text{-}C_4)$-alkyl, $S(O)_2OH$, $S(O)_2O(C_1\text{-}C_4)$-alkyl, $S(O)_2NH_2$, $S(O)_2NH(C_1\text{-}C_4)$-alkyl, and $S(O)_2N((C_1\text{-}C_4)\text{-alkyl})_2$. If a moiety is substituted with more than 1 substituent, e.g. by 2, 3, 4, or 5 substituents, these substituents may be identical or different. Preferably, the substituents may be selected from the group consisting of F, Cl, Br, $CF_3$, $CHF_2$, $CH_2F$, $OCF_3$, OH, CN, $(C_1\text{-}C_4)$-alkyl, $(C_1\text{-}C_4)$-hydroxyalkyl, $(C_1\text{-}C_4)$-alkoxy, $(C_3\text{-}C_6)$-cycloalkyl, $NH_2$, $NH(C_1\text{-}C_4)$-alkyl, $N((C_1\text{-}C_4)\text{-alkyl})_2$, $NHCO(C_1\text{-}C_4)$-alkyl, $NHCONH(C_1\text{-}C_4)$-alkyl, $NHCON((C_1\text{-}C_4)\text{-alkyl})_2$, $NHS(O)_2(C_1\text{-}C_4)$-alkyl, $CONH_2$, $CONH(C_1\text{-}C_4)$-alkyl, $CON((C_1\text{-}C_4)\text{-alkyl})_2$, $S(O)(C_1\text{-}C_4)$-alkyl and $S(O)_2(C_1\text{-}C_4)$-alkyl.

Within the scope of the present invention, the symbol

used in the formulae denotes a link of a corresponding residue to the respective superordinate general structure.

In one embodiment of the first aspect of the invention, the compound according to general formula (I) is characterized in that Y represents O.

In another embodiment of the first aspect of the invention, the compound according to general formula (I) is characterized in that $R^{3a}$ represents H.

In another embodiment of the first aspect of the invention, the compound according to general formula (I) is characterized in that
Z represents $N(R^{3b})$, wherein $R^{3b}$ represents H; or
Z represents $C(R^{4a}R^{4b})$, wherein $R^{4a}$ represents $CH_3$ and $R^{4b}$ represents H or wherein $R^{4a}$ and $R^{4b}$ each represent H.

In a preferred embodiment of the invention, Z represents $C(R^{4a}R^{4b})$, wherein $R^{4a}$ represents $CH_3$ and $R^{4b}$ represents H, therefore being in one enantiomeric form.

Preferably, Z represents $C(R^{4a}R^{4b})$, wherein $R^{4a}$ represents $CH_3$ and $R^{4b}$ represents H, and the carbon atom bearing the residues $R^{4a}$ and $R^{4b}$ has the (R)-configuration or has the (S)-configuration:

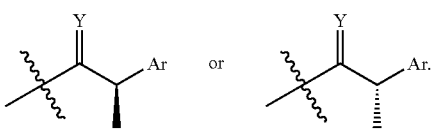

More preferably, the compound according to general formula (I) is characterized in that
Z represents $N(R^{3b})$, wherein $R^{3b}$ represents H.

In yet another embodiment of the first aspect of the invention, the compound according to general formula (I) is characterized in that $R^2$ represents $CH_3$, $CFH_2$, $CHF_2$, $CF_3$, $CH_2CH_3$, $CH(CH_3)_2$ or $C(CH_3)_3$.

In a preferred embodiment of the invention, the compound according to general formula (I) is characterized in that $R^2$ represents $CF_3$ or $C(CH_3)_3$.

In another preferred embodiment of the first aspect of the invention, the compound according to general formula (I) is characterized in that
$R^1$ represents

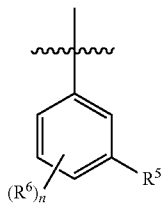

wherein
n is 0, 1, 2 or 3;
$R^5$ represents F, Cl, Br, CN, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy and $C_{1-4}$-alkoxy-$C_{1-4}$-alkoxy
and
each $R^6$ independently is selected from the group consisting of F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, $C_{1-4}$-alkylS(O), hydroxy-$C_{1-4}$-alkylS(O), $C_{1-4}$-alkylS(O)$_2$, hydroxy-$C_{1-4}$-alkylS(O)$_2$, $H_2N$, $(C_{1-4}$-alkyl)(H)N, (hydroxy-$C_{1-4}$-alkyl)(H)N, $(C_{1-4}$-alkyl)$_2$N, (hydroxy-$C_{1-4}$-alkyl)($C_{1-4}$-alkyl)N, (hydroxy-$C_{1-4}$-alkyl)$_2$N, [($C_{1-4}$-alkyl)(H)N]($C_{1-4}$-alkyl), [(hydroxy-$C_{1-4}$-alkyl)(H)N]($C_{1-4}$-alkyl), [($C_{1-4}$-alkyl)$_2$N]($C_{1-4}$-alkyl), [(hydroxy-$C_{1-4}$-alkyl)($C_{1-4}$-alkyl)N]($C_{1-4}$-alkyl), $H_2NC(O)$, ($C_{1-4}$-alkyl)(H)NC(O), (hydroxy-$C_{1-4}$-alkyl)(H)NC(O), ($C_{1-4}$-alkyl)$_2$NC(O), (hydroxy-$C_{1-4}$-alkyl)($C_{1-4}$-alkyl)NC(O), (hydroxy-$C_{1-4}$-alkyl)$_2$N—C(O), $H_2NS(O)_2$, ($C_{1-4}$-alkyl)(H)NS(O)$_2$, (hydroxy-$C_{1-4}$-alkyl)(H)N—S(O)$_2$, ($C_{1-4}$-alkyl)$_2$NS(O)$_2$, (hydroxy-$C_{1-4}$-alkyl)($C_{1-4}$-alkyl)NS(O)$_2$, (hydroxy-$C_{1-4}$-alkyl)$_2$NS(O)$_2$, $C_{3-6}$-cycloalkyl, ($C_{3-6}$-cycloalkyl)-$C_{1-4}$-alkyl, ($C_{3-6}$-cycloalkyl)-$C_{1-4}$-alkoxy, $C_{3-7}$-heterocycloalkyl, ($C_{3-7}$-heterocycloalkyl)-$C_{1-4}$-alkyl, ($C_{3-7}$-heterocycloalkyl)-$C_{1-4}$-alkoxy,
wherein said $C_{3-6}$-cycloalkyl or $C_{3-7}$-heterocycloalkyl may be unsubstituted or mono- or independently polysubstituted by one or more substituents, selected from H, F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;
aryl, heteroaryl, (aryl)$C_{1-4}$-alkyl or (heteroaryl)$C_{1-4}$-alkyl, wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy.

Preferably,
$R^1$ is selected from the group consisting of

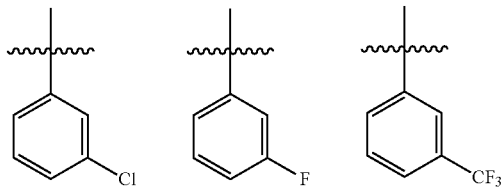

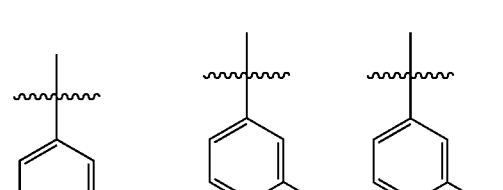

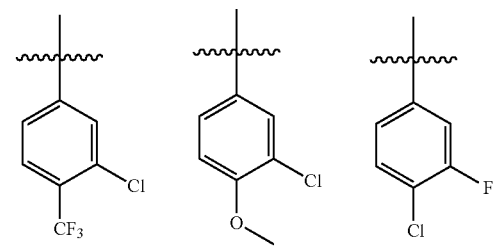

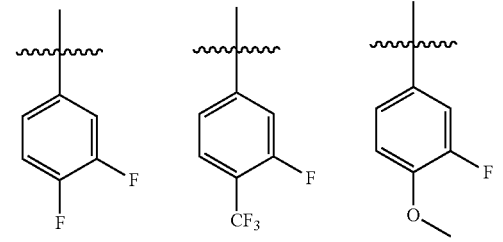

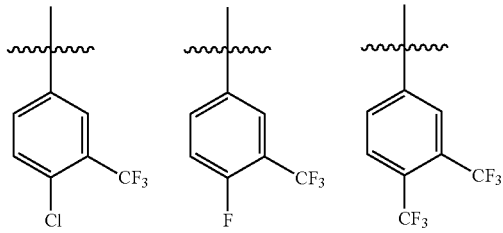

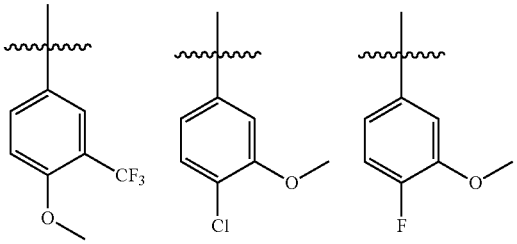

-continued

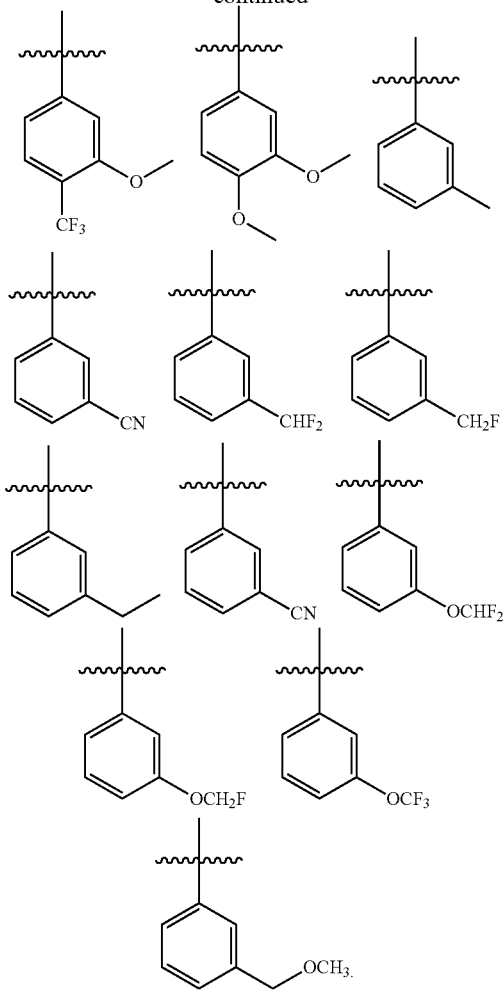

Particularly preferably, R¹ represents

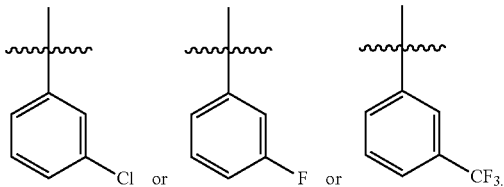 [SMILES: *c1cccc(Cl)c1 ; *c1cccc(F)c1 ; *c1cccc(C(F)(F)F)c1]

Even more preferably, R¹ represents

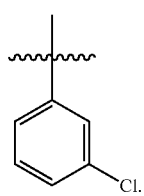 [SMILES: *c1cccc(Cl)c1]

In another preferred embodiment of the first aspect of the invention, the compound according to general formula (I) is characterized in that the compound of general formula (I) has general formula (Ia)

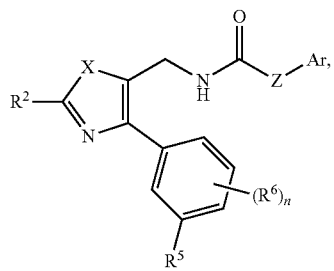

(Ia)

wherein
X represents O or S;
Z represents $N(R^{3b})$ or $C(R^{4a}R^{4b})$;
n is 0, 1 or 2;
$R^2$ represents $CH_3$, $CFH_2$, $CHF_2$, $CF_3$, $CH_2CH_3$, $CH(CH_3)_2$ or $C(CH_3)_3$,
$R^{3b}$ represents H, $C_{1-4}$-alkyl, hydroxy-$C_{1-4}$-alkyl, halo-$C_{1-4}$-alkyl, cyano-$C_{1-4}$-alkyl or $C_{1-4}$-alkoxy-$C_{1-4}$-alkyl;
$R^{4a}$ and $R^{4b}$ each independently represent H, F, Cl or $C_{1-4}$-alkyl;
$R^5$ represents F, Cl, Br, CN, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, and $C_{1-4}$-alkoxy-$C_{1-4}$-alkoxy;
each $R^6$ independently is selected from the group consisting of F, Cl, Br, CN, OH, $C_{1-4}$-alkyl, $CF_3$, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, $C_{1-4}$-alkylS(O), $C_{1-4}$-alkylS(O)$_2$, $H_2N$, ($C_{1-4}$-alkyl)(H)N, ($C_{1-4}$-alkyl)$_2$N, $H_2NC(O)$, ($C_{1-4}$-alkyl)(H)NC(O) and ($C_{1-4}$-alkyl)$_2$NC(O);
and
Ar represents aryl or heteroaryl,
wherein said aryl or heteroaryl may be condensed with an aromatic or aliphatic ring to form a bicycle,
and wherein said aryl or heteroaryl and said condensed aromatic or aliphatic ring each independently may be unsubstituted or mono- or independently polysubstituted by one or more substituents, selected from the group consisting of F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, hydroxy-$C_{1-4}$-alkoxy-$C_{1-4}$-alkyl, $C_{1-4}$-alkylS(O), hydroxy-$C_{1-4}$-alkylS(O), halo-$C_{1-4}$-alkylS(O), cyano-$C_{1-4}$-alkylS(O), $C_{1-4}$-alkoxy-$C_{1-4}$-alkylS(O), $C_{1-4}$-alkylS(O)$_2$, hydroxy-$C_{1-4}$-alkylS(O)$_2$, halo-$C_{1-4}$-alkylS(O)$_2$, cyano-$C_{1-4}$-alkylS(O)$_2$, $C_{1-4}$-alkoxy-$C_{1-4}$-alkylS(O)$_2$, $C_{1-4}$-alkylS(O)$C_{1-4}$-alkyl, hydroxy-$C_{1-4}$-alkylS(O)$C_{1-4}$-alkyl, $C_{1-4}$-alkylS(O)$_2C_{1-4}$-alkyl, hydroxy-$C_{1-4}$-alkyl-S(O)$_2C_{1-4}$-alkyl, $H_2N$, ($C_{1-4}$-alkyl)(H)N, (hydroxy-$C_{1-4}$-alkyl)(H)N, (halo-$C_{1-4}$-alkyl)(H)N, (cyano-$C_{1-4}$-alkyl)(H)N, ($C_{1-4}$-alkoxy-$C_{1-4}$-alkyl)(H)N, ($C_{3-6}$-cycloalkyl)(H)N, ($C_{3-7}$-heterocycloalkyl)(H)N, ($C_{1-4}$-alkyl)$_2$N, (hydroxy-$C_{1-4}$-alkyl)($C_{1-4}$-alkyl)N, (halo-$C_{1-4}$-alkyl)($C_{1-4}$-alkyl)N, (cyano-$C_{1-4}$-alkyl)($C_{1-4}$-alkyl)N, ($C_{1-4}$-alkoxy-$C_{1-4}$-alkyl)($C_{1-4}$-alkyl)N, ($C_{3-6}$-cycloalkyl)($C_{1-4}$-alkyl)N, ($C_{3-7}$-heterocycloalkyl)($C_{1-4}$-alkyl)N, (hydroxy-$C_{1-4}$-alkyl)$_2$N, ($C_{3-6}$-cyclo-alkyl)(hydroxy-$C_{1-4}$-alkyl)N, ($C_{3-7}$-heterocycloalkyl)(hydroxy-$C_{1-4}$-alkyl)N, $(H)_2NC_{1-4}$-alkyl, [($C_{1-4}$-alkyl)(H)N]($C_{1-4}$-alkyl), [(hydroxy-$C_{1-4}$-alkyl)

(H)N](C₁₋₄-alkyl), [(halo-C₁₋₄-alkyl)(H)N](C₁₋₄-alkyl), [(cyano-C₁₋₄-alkyl)(H)](C₁₋₄-alkyl), [(C₁₋₄-alkoxy-C₁₋₄-alkyl)(H)N](C₁₋₄-alkyl), [(C₃₋₆-cycloalkyl)(H)N](C₁₋₄-alkyl), [(C₃₋₇-heterocycloalkyl)(H)N](C₁₋₄-alkyl), [(C₁₋₄-alkyl)₂N](C₁₋₄-alkyl), [(hydroxy-C₁₋₄-alkyl)(C₁₋₄-alkyl)N](C₁₋₄-alkyl), [(halo-C₁₋₄-alkyl)(C₁₋₄-alkyl)N](C₁₋₄-alkyl), [(cyano-C₁₋₄-alkyl)(C₁₋₄-alkyl)N](C₁₋₄-alkyl), [(C₁₋₄-alkoxy-C₁₋₄-alkyl)(C₁₋₄-alkyl)N](C₁₋₄-alkyl), [(C₃₋₆-cycloalkyl)(C₁₋₄-alkyl)N](C₁-4-alkyl), [(C₃₋₇-heterocycloalkyl)(C₁₋₄-alkyl)N](C₁₋₄-alkyl), [(hydroxy-C₁₋₄-alkyl)₂N](C₁₋₄-alkyl), [(C₃₋₆-cycloalkyl)(hydroxy-C₁₋₄-alkyl)N](C₁₋₄-alkyl), [(C₃₋₇-heterocycloalkyl)(hydroxy-C₁₋₄-alkyl)N](C₁₋₄-alkyl), H₂NC(O), (C₁₋₄-alkyl)(H)NC(O), (hydroxy-C₁₋₄-alkyl)(H)NC(O), (halo-C₁₋₄-alkyl)(H)NC(O), (cyano-C₁₋₄-alkyl)(H)NC(O), (C₁₋₄-alkoxy-C₁₋₄-alkyl)(H)NC(O), (C₃₋₆-cyclo-alkyl)(H)NC(O), (C₃₋₇-heterocycloalkyl)(H)NC(O), (C₁₋₄-alkyl)₂NC(O), (hydroxy-C₁₋₄-alkyl)(C₁₋₄-alkyl)NC(O), (halo-C₁₋₄-alkyl)(C₁₋₄-alkyl)NC(O), (cyano-C₁₋₄-alkyl)(C₁₋₄-alkyl)NC(O), (C₁₋₄-alkoxy-C₁₋₄-alkyl)(C₁₋₄-alkyl)NC(O), (C₃₋₆-cycloalkyl)(C₁₋₄-alkyl)NC(O), (C₃₋₇-heterocycloalkyl)(C₁₋₄-alkyl)NC(O), (hydroxy-C₁₋₄-alkyl)₂NC(O), (C₃₋₆-cycloalkyl)(hydroxy-C₁₋₄-alkyl)NC(O), (C₃₋₇-heterocycloalkyl)(hydroxy-C₁₋₄-alkyl)NC(O), H₂NS(O)₂, (C₁₋₄-alkyl)(H)NS(O)₂, (hydroxy-C₁₋₄-alkyl)(H)NS(O)₂, (halo-C₁₋₄-alkyl)(H)NS(O)₂, (cyano-C₁₋₄-alkyl)(H)NS(O)₂, (C₁₋₄-alkoxy-C₁₋₄-alkyl)(H)—NS(O)₂, (C₃₋₆-cycloalkyl)(H)NS(O)₂, (C₃₋₇-heterocycloalkyl)(H)NS(O)₂, (C₁₋₄-alkyl)₂NS(O)₂, (hydroxy-C₁₋₄-alkyl)(C₁₋₄-alkyl)NS(O)₂, (halo-C₁₋₄-alkyl)(C₁₋₄-alkyl)NS(O)₂, (cyano-C₁₋₄-alkyl)(C₁₋₄-alkyl)NS(O)₂, (C₁₋₄-alkoxy-C₁₋₄-alkyl)(C₁₋₄-alkyl)NS(O)₂, (C₃₋₆-cycloalkyl)(C₁₋₄-alkyl)NS(O)₂, (C₃₋₇-hetero-cycloalkyl)(C₁₋₄-alkyl)NS(O)₂, (hydroxy-C₁₋₄-alkyl)₂NS(O)₂, (C₃₋₆-cycloalkyl)-(hydroxy-C₁₋₄-alkyl)NS(O)₂, (C₃₋₇-heterocycloalkyl)(hydroxy-C₁₋₄-alkyl)NS(O)₂, H₂NS(O)₂N(H)C₁₋₄-alkyl, (C₁₋₄-alkyl)(H)NS(O)₂N(H)C₁₋₄-alkyl, (hydroxy-C₁₋₄-alkyl)(H)NS(O)₂N(H)C₁₋₄-alkyl, (C₁₋₄-alkyl)₂NS(O)₂N(H)C₁₋₄-alkyl, (C₁₋₄-alkyl)S(O)₂N(H)C₁₋₄-alkyl, (hydroxy-C₁₋₄-alkyl)S(O)₂N(H)C₁₋₄-alkyl, C₃₋₆-cycloalkyl, (C₃₋₆-cycloalkyl)-C₁₋₄-alkyl, (C₃₋₆-cycloalkyl)-C₁₋₄-alkoxy, C₃₋₇-heterocycloalkyl, (C₃₋₇-heterocycloalkyl)-C₁₋₄-alkyl, (C₃₋₇-heterocycloalkyl)-C₁₋₄-alkoxy, wherein said C₃₋₆-cycloalkyl or C₃₋₇-heterocycloalkyl may be unsubstituted or mono- or independently polysubstituted by one or more substituents, selected from H, F, Cl, Br, CN, OH, =O, C₁₋₄-alkyl, hydroxy-C₁₋₄-alkyl, halo-C₁₋₄-alkyl, cyano-C₁₋₄-alkyl, C₁₋₄-alkoxy-C₁₋₄-alkyl, hydroxy-C₁₋₄-alkoxy, halo-C₁₋₄-alkoxy, cyano-C₁₋₄-alkoxy and C₁₋₄-alkoxy-C₁₋₄-alkoxy;

aryl, heteroaryl, (aryl)C₁₋₄-alkyl or (heteroaryl)C₁₋₄-alkyl, wherein said aryl or heteroaryl may be unsubstituted or mono- or independently polysubstituted by one or more substituents, selected from the group consisting of H, F, Cl, Br, CN, OH, C₁₋₄-alkyl, hydroxy-C₁₋₄-alkyl, halo-C₁₋₄-alkyl, cyano-C₁₋₄-alkyl, C₁₋₄-alkoxy-C₁₋₄-alkyl, hydroxy-C₁₋₄-alkoxy, halo-C₁₋₄-alkoxy, cyano-C₁₋₄-alkoxy and C₁₋₄-alkoxy-C₁₋₄-alkoxy;

optionally in the form of a single stereoisomer or a mixture of stereoisomers, in the form of the free compound and/or a physiologically acceptable salt or a solvate thereof.

In one preferred embodiment of the first aspect of the invention, the compound according to general formula (I) or according to general formula (Ia) is characterized in that X is O.

In another preferred embodiment of the first aspect of the invention, the compound according to general formula (I) or according to general formula (Ia) is characterized in that X is S.

In another preferred embodiment of the first aspect of the invention, the compound according to general formula (I) is characterized in that the compound has general formula (Ia), wherein n is 0.

In another preferred embodiment of the first aspect of the invention, the compound according to general formula (I) is characterized in that the compound has general formula (Ia), wherein R⁵ is F, Cl, CN, CH₃, CHF₂, CF₃, CH₂CH₃, OCH₃, OCF₃, OCHF₂ or CH₂OCH₃.

Preferably, the compound according to general formula (I) is characterized in that the compound has general formula (Ia), wherein R⁵ is F, Cl, CN, CH₃, CHF₂, CF₃, CH₂CH₃, OCH₃, OCF₃, OCHF₂ or CH₂OCH₃ and n is 0.

In yet another embodiment of the first aspect of the invention, the compound according to general formula (I) or general formula (Ia) is characterized in that Ar is selected from phenyl or pyridinyl, wherein said phenyl or pyridinyl may be condensed with an aromatic or aliphatic ring to form a bicycle, and wherein said phenyl or pyridinyl and said condensed aromatic or aliphatic ring each independently may be unsubstituted or mono- or independently polysubstituted by one or more substituents, selected from the group consisting of F, Cl, Br, CN, OH, =O, C₁₋₄-alkyl, hydroxy-C₁₋₄-alkyl, halo-C₁₋₄-alkyl, C₁₋₄-alkoxy-C₁₋₄-alkyl, hydroxy-C₁₋₄-alkoxy, halo-C₁₋₄-alkoxy, C₁₋₄-alkoxy-C₁₋₄-alkoxy, H₂N, (C₁₋₄-alkyl)(H)N, (hydroxy-C₁₋₄-alkyl)(H)N, H₂NC(O), (C₁₋₄-alkyl)(H)NC(O), (hydroxy-C₁₋₄-alkyl)(H)NC(O), (C₁₋₄-alkyl)₂NC(O), (hydroxy-C₁₋₄-alkyl)(C₁₋₄-alkyl)NC(O) and C₃₋₆-cycloalkyl.

In a preferred embodiment of the first aspect of the invention, the compound according to general formula (I) or general formula (Ia) is characterized in that Ar is selected from phenyl or pyridinyl, wherein said phenyl or said pyridinyl is condensed with an aromatic or aliphatic ring to form a bicycle.

Preferably, the compound according to general formula (I) or general formula (Ia) is characterized in that
Ar is selected from

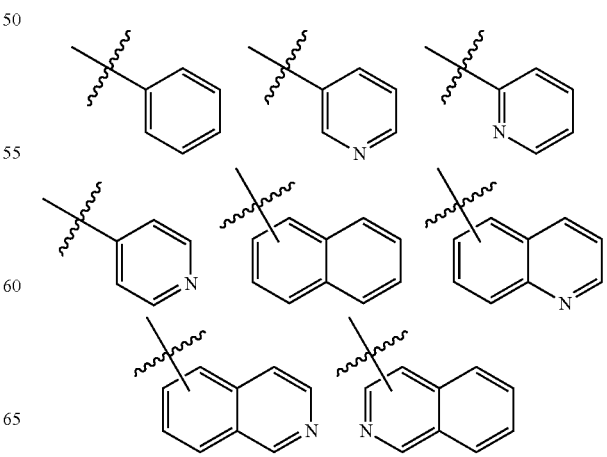

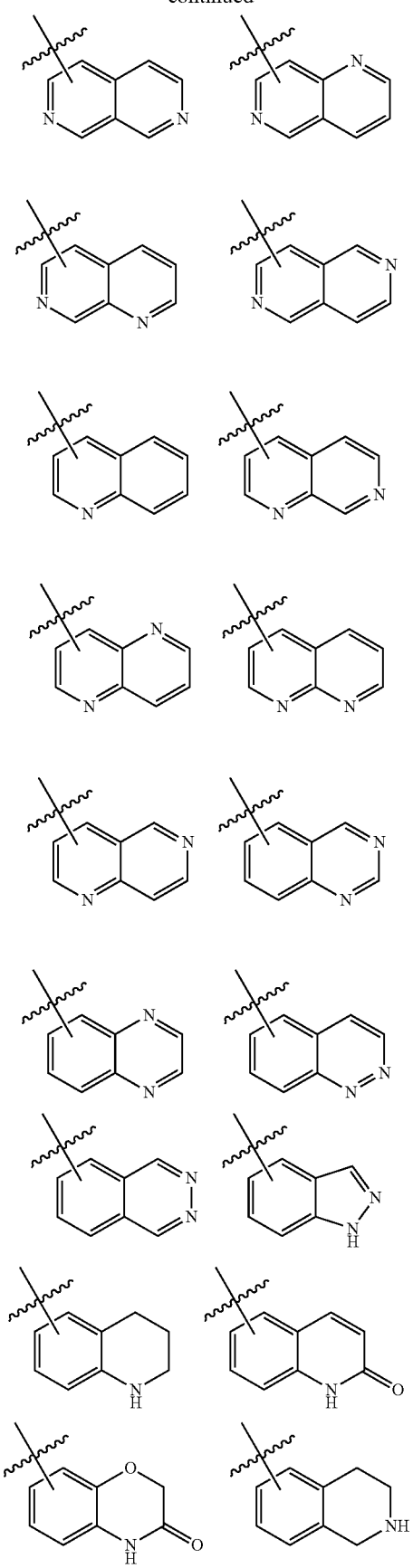
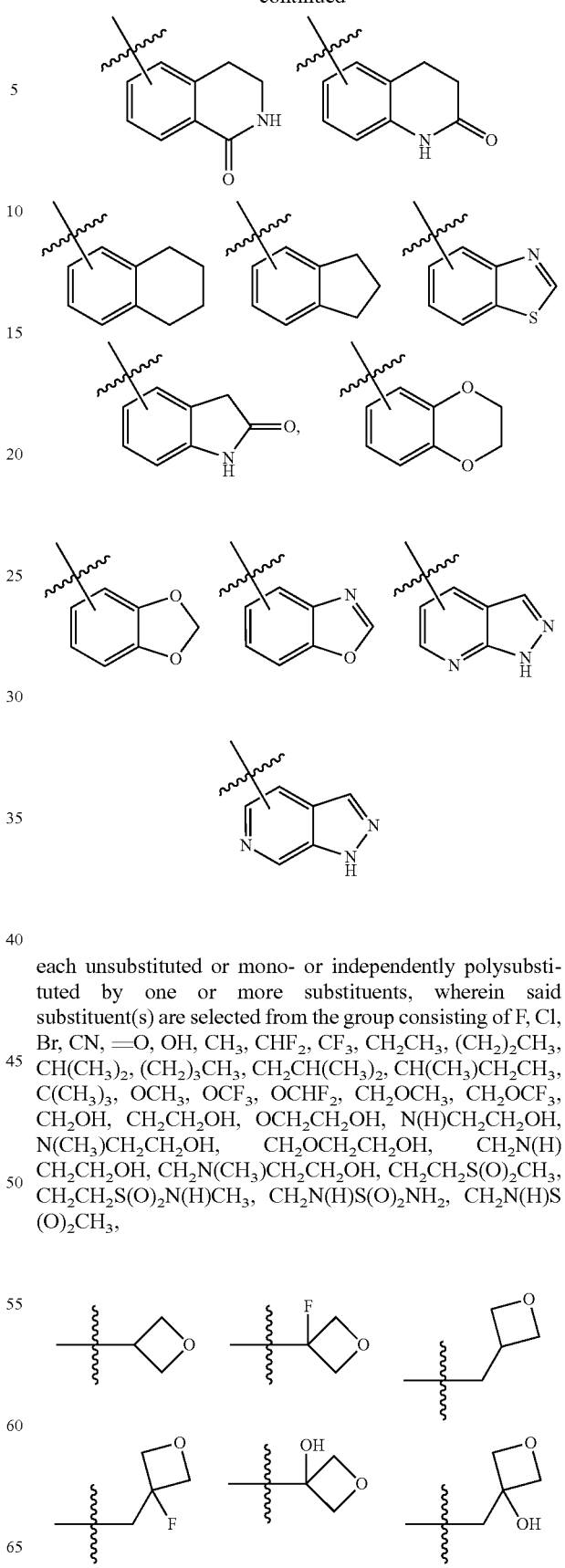

each unsubstituted or mono- or independently polysubstituted by one or more substituents, wherein said substituent(s) are selected from the group consisting of F, Cl, Br, CN, =O, OH, CH₃, CHF₂, CF₃, CH₂CH₃, (CH₂)₂CH₃, CH(CH₃)₂, (CH₂)₃CH₃, CH₂CH(CH₃)₂, CH(CH₃)CH₂CH₃, C(CH₃)₃, OCH₃, OCF₃, OCHF₂, CH₂OCH₃, CH₂OCF₃, CH₂OH, CH₂CH₂OH, OCH₂CH₂OH, N(H)CH₂CH₂OH, N(CH₃)CH₂CH₂OH, CH₂OCH₂CH₂OH, CH₂N(H) CH₂CH₂OH, CH₂N(CH₃)CH₂CH₂OH, CH₂CH₂S(O)₂CH₃, CH₂CH₂S(O)₂N(H)CH₃, CH₂N(H)S(O)₂NH₂, CH₂N(H)S (O)₂CH₃,

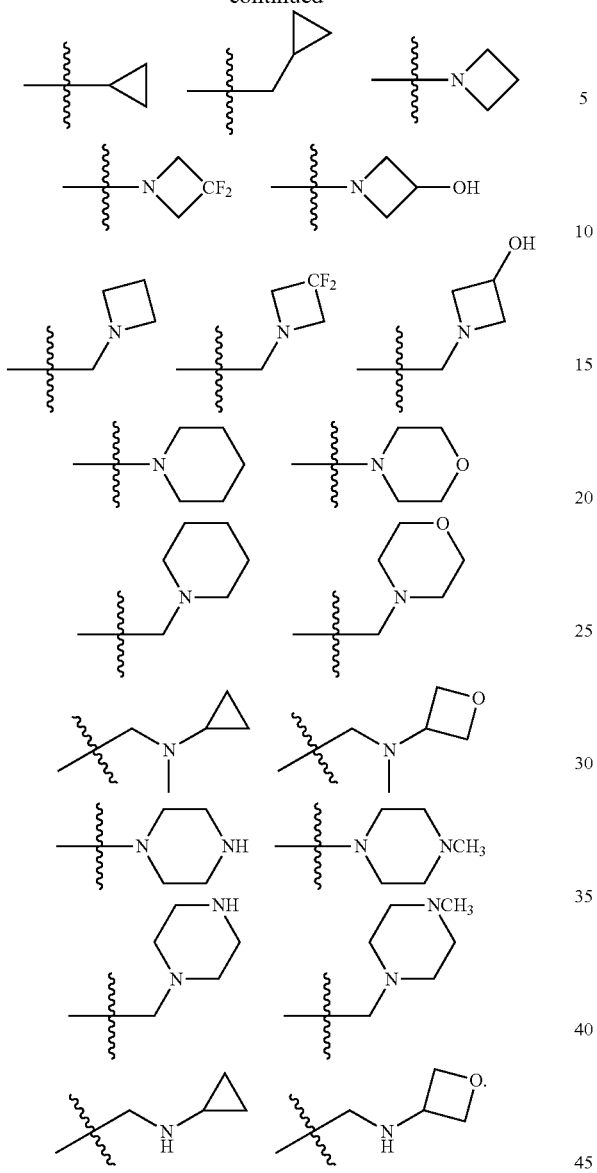

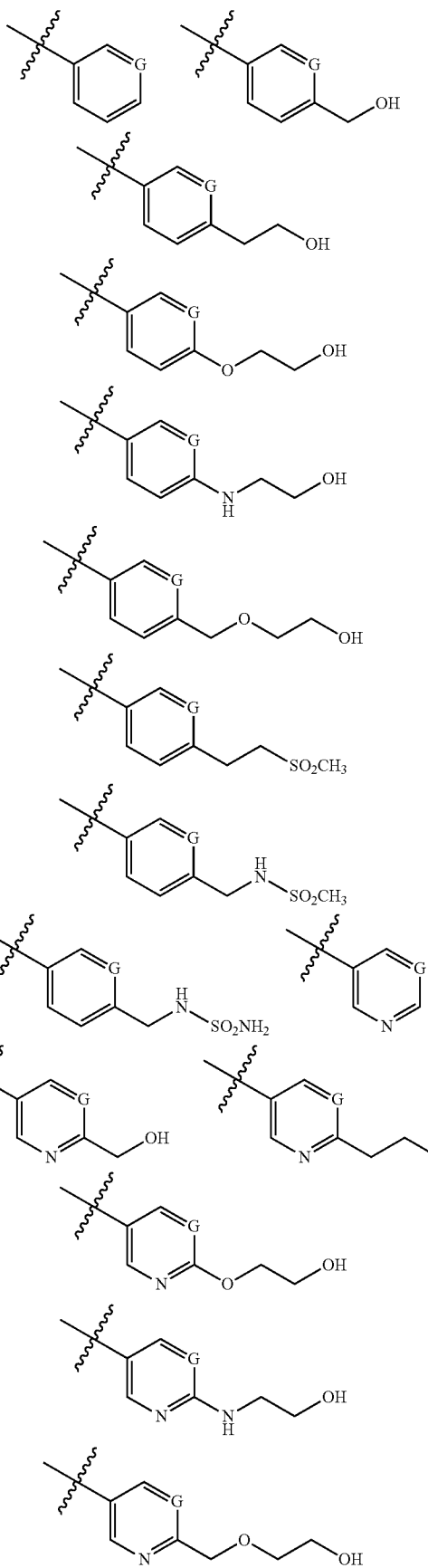

In a preferred embodiment of the first aspect of the invention, the compound according to general formula (I) or general formula (Ia) is characterized in that Ar is selected from 1-naphthyl, 2-naphthyl, 5-quinolinyl, 6-quinolinyl, 7-quinolinyl, 8-quinolinyl, 5-isoquinolinyl, 6-isoquinolinyl, 7-isoquinolinyl, 8-isoquinolinyl, 5-quinoxalinyl, 6-quinoxalinyl, 5-phthalazinyl, 6-phthalazinyl, 5-quinazolinyl, 6-quinazolinyl, 7-quinazolinyl, 8-quinazolinyl, 5-cinnolinyl, 6-cinnolinyl, 7-cinnolinyl, 8-cinnolinyl, 5-indazolyl, 5-(1-methyl)-indazolyl, 4-indazolyl, 4-(1-methyl)-indazolyl, 1-(5,6,7,8-tetrahydro)-naphthyl, 2-(5,6,7,8-tetrahydro)-naphthyl, 4-(2,3-dihydro)-1H-indenyl, 5-(2,3-dihydro)-1H-indenyl, 4-benzo[d][1,3]dioxolyl, 5-benzo[d][1,3]dioxolyl, 5-(2,3-dihydro)-benzo[b][1,4]dioxinyl, 6-(2,3-dihydro)-benzo[b][1,4]dioxinyl.

In a preferred embodiment of the first aspect of the invention, the compound according to general formula (I) or general formula (Ia) is characterized in that Ar is selected from

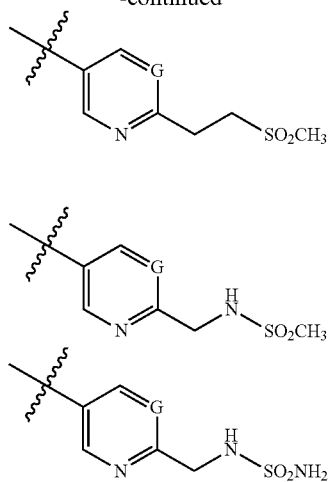

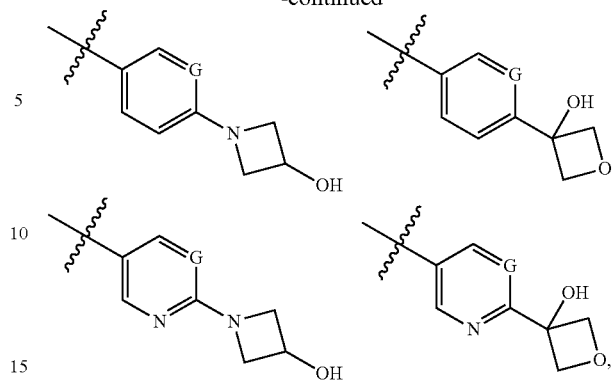

wherein G is CH or CF.

Particularly preferred are compounds according to the invention from the group

| | | |
|---|---|---|
| 1 | N-((4-(3-chlorophenyl)-2-(trifluoromethyl)thiazol-5-yl)methyl)-2-(3-fluoro-4-(2-hydroxyethyl)phenyl)-propanamide | EX-01 |
| 2 | N-((4-(3-chlorophenyl)-2-(trifluoromethyl)oxazol-5-yl)methyl)-2-(3-fluoro-4-(2-hydroxyethyl)-phenyl)propanamide | EX-02 |
| 3 | N-((2-(tert-butyl)-4-(3-chlorophenyl)thiazol-5-yl)methyl)-2-(3-fluoro-4-(methylsulfonamido-methyl)phenyl)propanamide | EX-03 |
| 4 | N-((2-(tert-butyl)-4-(m-tolyl)thiazol-5-yl)methyl)-2-(3-fluoro-4-(methylsulfonamidomethyl)phenyl)propanamide | EX-04 |
| 5 | N-((4-(3-chlorophenyl)-2-(trifluoromethyl)oxazol-5-yl)methyl)-2-(4-((sulfamoylamino)methyl)-phenyl)propanamide | EX-05 |
| 6 | N-((4-(3-chlorophenyl)-2-(trifluoromethyl)thiazol-5-yl)methyl)-2-(4-((sulfamoylamino)methyl)-phenyl)propanamide | EX-06 |
| 7 | N-((2-(tert-butyl)-4-(3-chlorophenyl)thiazol-5-yl)methyl)-2-(3-fluoro-4-(hydroxymethyl)phenyl)propanamide | EX-07 |
| 8 | N-((2-(tert-butyl)-4-(m-tolyl)thiazol-5-yl)methyl)-2-(3-fluoro-4-(hydroxymethyl)phenyl)propanamide | EX-08 |
| 9 | N-((4-(3-chlorophenyl)-2-(trifluoromethyl)oxazol-5-yl)methyl)-2-(4-(3-hydroxyoxetan-3-yl)phenyl)propanamide | EX-09 |
| 10 | N-((4-(3-chlorophenyl)-2-(trifluoromethyl)thiazol-5-yl)methyl)-2-(4-(3-hydroxyoxetan-3-yl)phenyl)propanamide | EX-10 |
| 11 | N-((4-(3-chlorophenyl)-2-(trifluoromethyl)oxazol-5-yl)methyl)-2-(5-fluoro-6-(2-(methylsulfonyl)ethyl)pyridin-3-yl)propanamide | EX-11 |
| 12 | N-((4-(3-chlorophenyl)-2-(trifluoromethyl)thiazol-5-yl)methyl)-2-(5-fluoro-6-(2-(methylsulfonyl)ethyl)pyridin-3-yl)propanamide | EX-12 |
| 13 | N-((4-(3-chlorophenyl)-2-(trifluoromethyl)oxazol-5-yl)methyl)-2-(6-((2-hydroxyethyl)amino)pyridin-3-yl)propanamide | EX-13 |
| 14 | N-((4-(3-chlorophenyl)-2-(trifluoromethyl)thiazol-5-yl)methyl)-2-(6-((2-hydroxyethyl)amino)pyridin-3-yl)propanamide | EX-14 |
| 15 | N-((4-(3-chlorophenyl)-2-(trifluoromethyl)thiazol-5-yl)methyl)-2-(6-((2-hydroxyethyl)amino)pyridin-3-yl)propanamide (enantiomer 1) | EX-15 |
| 16 | N-((4-(3-chlorophenyl)-2-(trifluoromethyl)thiazol-5-yl)methyl)-2-(6-((2-hydroxyethyl)amino)pyridin-3-yl)propanamide (enantiomer 2) | EX-16 |
| 17 | N-((4-(3-chlorophenyl)-2-(trifluoromethyl)oxazol-5-yl)methyl)-2-(6-((2-hydroxyethyl)amino)pyridin-3-yl)propanamide (nenantiomer 1) | EX-17 |
| 18 | N-((4-(3-chlorophenyl)-2-(trifluoromethyl)oxazol-5-yl)methyl)-2-(6-((2-hydroxyethyl)amino)pyridin-3-yl)propanamide (enantiomer 2) | EX-18 |
| 19 | N-((4-(3-chlorophenyl)-2-(trifluoromethyl)oxazol-5-yl)methyl)-2-(5-fluoro-6-(hydroxymethyl)pyridin-3-yl)propanamide | EX-19 |
| 20 | N-((4-(3-chlorophenyl)-2-(trifluoromethyl)thiazol-5-yl)methyl)-2-(5-fluoro-6-(hydroxymethyl)pyridin-3-yl)propanamide (enantiomer 1) | EX-20 |
| 21 | N-((4-(3-chlorophenyl)-2-(trifluoromethyl)oxazol-5-yl)methyl)-2-(5-fluoro-6-(hydroxymethyl)pyridin-3-yl)propanamide | EX-21 |
| 22 | N-((4-(3-chlorophenyl)-2-(trifluoromethyl)oxazol-5-yl)methyl)-2-(5-fluoro-6-(hydroxymethyl)pyridin-3-yl)propanamide (enantiomer 2) | EX-22 |
| 23 | N-((4-(3-chlorophenyl)-2-(trifluoromethyl)oxazol-5-yl)methyl)-2-(3-fluoro-4-((sulfamoylamino)methyl)phenyl)propanamide | EX-23 |
| 24 | N-((4-(3-chlorophenyl)-2-(trifluoromethyl)thiazol-5-yl)methyl)-2-(3-fluoro-4-((sulfamoylamino)methyl)phenyl)propanamide | EX-24 |

| | | |
|---|---|---|
| 25 | 1-((2-(tert-butyl)-4-(3-chlorophenyl)oxazol-5-yl)methyl)-3-(6-(hydroxymethyl)pyridin-3-yl)urea | EX-25 |
| 26 | 1-((2-(tert-butyl)-4-(3-chlorophenyl)thiazol-5-yl)methyl)-3-(6-(hydroxymethyl)pyridin-3-yl)urea | EX-26 |
| 27 | 1-((4-(3-chlorophenyl)-2-(trifluoromethyl)oxazol-5-yl)methyl)-3-(6-(hydroxymethyl)pyridin-3-yl)urea | EX-27 |
| 28 | 1-((4-(3-chlorophenyl)-2-(trifluoromethyl)thiazol-5-yl)methyl)-3-(6-(hydroxymethyl)pyridin-3-yl)urea | EX-28 |
| 29 | 1-((2-(tert-butyl)-4-(3-chlorophenyl)thiazol-5-yl)methyl)-3-(2-methoxypyrimidin-5-yl)urea | EX-29 |
| 30 | 1-((4-(3-chlorophenyl)-2-(trifluoromethyl)oxazol-5-yl)methyl)-3-(6-(2-(methylsulfonyl)ethyl)pyridin-3-yl)urea | EX-30 |
| 31 | 1-((4-(3-chlorophenyl)-2-(trifluoromethyl)thiazol-5-yl)methyl)-3-(6-(2-(methylsulfonyl)ethyl)pyridin-3-yl)urea | EX-31 |
| 32 | 1-((4-(3-chlorophenyl)-2-(trifluoromethyl)oxazol-5-yl)methyl)-3-(6-(3-hydroxyazetidin-1-yl)pyridin-3-yl)urea | EX-32 |
| 33 | 1-((4-(3-chlorophenyl)-2-(trifluoromethyl)thiazol-5-yl)methyl)-3-(6-(3-hydroxyazetidin-1-yl)pyridin-3-yl)urea | EX-33 |
| 34 | 1-((4-(3-chlorophenyl)-2-(trifluoromethyl)thiazol-5-yl)methyl)-3-(6-(2-hydroxyethyl)pyridin-3-yl)urea | EX-34 |
| 35 | 1-((2-(tert-butyl)-4-(3-chlorophenyl)oxazol-5-yl)methyl)-3-(6-(2-hydroxyethyl)pyridin-3-yl)urea | EX-35 |
| 36 | 1-((2-(tert-butyl)-4-(3-chlorophenyl)thiazol-5-yl)methyl)-3-(6-(2-hydroxyethyl)pyridin-3-yl)urea | EX-36 |
| 37 | 1-((4-(3-chlorophenyl)-2-(trifluoromethyl)oxazol-5-yl)methyl)-3-(6-(2-hydroxyethyl)pyridin-3-yl)urea | EX-37 |
| 38 | N-(4-(3-((2-(tert-butyl)-4-(3-chlorophenyl)oxazol-5-yl)methyl)ureido)benzyl)methanesulfonamide | EX-38 |
| 39 | N-(4-(3-((2-(tert-butyl)-4-(3-fluorophenyl)thiazol-5-yl)methyl)ureido)benzyl)methanesulfonamide | EX-39 |
| 40 | 1-((2-(tert-butyl)-4-(3-chlorophenyl)oxazol-5-yl)methyl)-3-(6-(2-hydroxyethoxy)pyridin-3-yl)urea | EX-40 |
| 41 | 1-((2-(tert-butyl)-4-(3-chlorophenyl)thiazol-5-yl)methyl)-3-(6-(2-hydroxyethoxy)pyridin-3-yl)urea | EX-41 |
| 42 | 1-((4-(3-chlorophenyl)-2-(trifluoromethyl)oxazol-5-yl)methyl)-3-(6-(2-hydroxyethoxy)pyridin-3-yl)urea | EX-42 |
| 43 | 1-((4-(3-chlorophenyl)-2-(trifluoromethyl)thiazol-5-yl)methyl)-3-(6-(2-hydroxyethoxy)pyridin-3-yl)urea | EX-43 |
| 44 | N-((5-(3-chlorophenyl)-2-(tertbutyl)oxazol-4-yl)methyl)-N'-(4-((sulfamoylamino)methyl)phenyl)urea | EX-44 |
| 45 | N-((5-(3-chlorophenyl)-2-(tertbutyl)thiazol-5-yl)methyl)-N'-(4-((sulfamoylamino)methyl)phenyl)urea | EX-45 |
| 46 | 1-((2-(tert-butyl)-4-(3-chlorophenyl)oxazol-5-yl)methyl)-3-(6-((2-hydroxyethoxy)methyl)pyridin-3-yl)urea dihydrochloride | EX-46 |
| 47 | 1-((2-(tert-butyl)-4-(3-chlorophenyl)thiazol-5-yl)methyl)-3-(6-((2-hydroxyethoxy)-methyl)pyridin-3-yl)urea dihydrochloride | EX-47 |
| 48 | 1-((4-(3-chlorophenyl)-2-(trifluoromethyl)oxazol-5-yl)methyl)-3-(6-((2-hydroxyethoxy)methyl)pyridin-3-yl)urea dihydrochloride | EX-48 |
| 49 | 1-((4-(3-chlorophenyl)-2-(trifluoromethyl)thiazol-5-yl)methyl)-3-(6-((2-hydroxyethoxy)methyl)pyridin-3-yl)urea dihydrochloride | EX-49 |
| 50 | 1-(benzo[d][1,3]dioxol-5-yl)-3-((2-(tert-butyl)-4-(3-chlorophenyl)thiazol-5-yl)methyl)urea | EX-50 |
| 51 | 1-((2-(tert-butyl)-4-(3-chlorophenyl)thiazol-5-yl)methyl)-3-(2,3-dihydro-1H-inden-4-yl)urea | EX-51 |
| 52 | 1-((2-(tert-butyl)-4-(3-chlorophenyl)thiazol-5-yl)methyl)-3-(isoquinolin-6-yl)urea | EX-52 |
| 53 | 1-((2-(tert-butyl)-4-(3-chlorophenyl)thiazol-5-yl)methyl)-3-(quinolin-5-yl)urea | EX-53 |
| 54 | 1-((2-(tert-butyl)-4-(3-chlorophenyl)thiazol-5-yl)methyl)-3-(2,3-dihydrobenzo[b][1,4]dioxin-6-yl)urea | EX-54 |
| 55 | 1-((2-(tert-butyl)-4-(3-chlorophenyl)thiazol-5-yl)methyl)-3-(2,3-dihydro-1H-inden-5-yl)urea | EX-55 |
| 56 | 1-((2-(tert-butyl)-4-(3-chlorophenyl)thiazol-5-yl)methyl)-3-(isoquinolin-5-yl)urea | EX-56 |
| 57 | N-(4-(3-((2-(tert-butyl)-4-(3-chlorophenyl)thiazol-5-yl)methyl)ureido)-2-fluorobenzyl)methanesulfonamide | EX-57 |
| 58 | N-(4-(3-((2-(tert-butyl)-4-(m-tolyl)thiazol-5-yl)methyl)ureido)-2-fluorobenzyl)methanesulfonamide | EX-58 |
| 59 | 1-((2-(tert-butyl)-4-(3-chlorophenyl)thiazol-5-yl)methyl)-3-(3-fluoro-4-(hydroxymethyl)phenyl)urea | EX-59 |
| 60 | 1-((2-(tert-butyl)-4-(m-tolyl)thiazol-5-yl)methyl)-3-(3-fluoro-4-(hydroxymethyl)phenyl)urea | EX-60 |
| 61 | 1-((2-(tert-butyl)-4-(3-chlorophenyl)thiazol-5-yl)methyl)-3-(3-methoxypyridin-4-yl)urea | EX-61 |
| 62 | 1-((2-(tert-butyl)-4-(3-chlorophenyl)thiazol-5-yl)methyl)-3-(pyrimidin-5-yl)urea | EX-62 |
| 63 | 1-((2-(tert-butyl)-4-(3-chlorophenyl)thiazol-5-yl)methyl)-3-(5-methylpyridin-2-yl)urea | EX-63 |

-continued

| | | |
|---|---|---|
| 64 | 1-((2-(tert-butyl)-4-(3-chlorophenyl)thiazol-5-yl)methyl)-3-(pyridin-4-yl)urea | EX-64 |
| 65 | 1-((2-(tert-butyl)-4-(3-chlorophenyl)thiazol-5-yl)methyl)-3-(pyridin-2-yl)urea | EX-65 |
| 66 | 1-((2-(tert-butyl)-4-(3-chlorophenyl)thiazol-5-yl)methyl)-3-(pyridin-3-yl)urea | EX-66 |
| 67 | 1-((2-(tert-butyl)-4-(3-chlorophenyl)thiazol-5-yl)methyl)-3-(3-methylpyridin-4-yl)urea | EX-67 |
| 68 | 1-((2-(tert-butyl)-4-(3-chlorophenyl)thiazol-5-yl)methyl)-3-(2-methylpyridin-4-yl)urea | EX-68 |
| 69 | 1-((2-(tert-butyl)-4-(3-chlorophenyl)thiazol-5-yl)methyl)-3-(6-fluoropyridin-3-yl)urea | EX-69 |
| 70 | 1-((2-(tert-butyl)-4-(3-chlorophenyl)thiazol-5-yl)methyl)-3-(6-methylpyridin-3-yl)urea | EX-70 |
| 71 | 1-((2-(tert-butyl)-4-(3-chlorophenyl)thiazol-5-yl)methyl)-3-(2-methylpyrimidin-5-yl)urea | EX-71 |

Furthermore, preference may be given to compounds according to the first aspect of the invention that cause a 50% displacement of capsaicin, which is present at a concentration of 100 nM, in a FLIPR assay with CHO K1 cells which were transfected with the human VR1 gene at a concentration of less than 2 000 nM, preferably less than 1 000 nM, particularly preferably less than 300 nM, most particularly preferably less than 100 nM, even more preferably less than 75 nM, additionally preferably less than 50 nM, most preferably less than 10 nM. In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The compounds according to the first aspect of the invention and corresponding stereoisomers and also the respective corresponding acids, bases, salts and solvates are toxicologically safe and are therefore suitable as pharmaceutical active ingredients in pharmaceutical compositions.

In second aspect of the invention, the invention therefore further relates to a pharmaceutical composition containing at least one compound according to the first aspect of the invention, in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect. Likewise, the pharmaceutical compositions according to the invention are preferably suitable for the prophylaxis and/or treatment of disorders or diseases which are mediated, at least in part, by vanilloid receptors 1. The pharmaceutical composition according to the invention is suitable for administration to adults and children, including toddlers and babies. The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In a preferred embodiment of the second aspect of the invention, the pharmaceutical composition according to the invention is suitable for the treatment and/or prophylaxis of pain, preferably of pain selected from the group consisting of acute pain, chronic pain, neuropathic pain and visceral pain.

In a third aspect of the invention, the present invention further relates to a compound according to the first aspect of the invention for use in vanilloid receptor 1-(VR1/TRPV1) regulation, preferably for use in vanilloid receptor 1-(VR1/TRPV1) inhibition and/or vanilloid receptor 1-(VR1/TRPV1) stimulation.

The present invention therefore further relates to a compound according to the first aspect of the invention and also for use in the prophylaxis and/or treatment of disorders and/or diseases which are mediated, at least in part, by vanilloid receptors 1.

In particular, the present invention therefore further relates to a compound according to the first aspect of the invention for use in the prophylaxis and/or treatment of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists.

A preferred embodiment of the third aspect of the invention is a compound according to the first aspect of the invention for use in the prophylaxis and/or treatment of pain, preferably of pain selected from the group consisting of acute pain, chronic pain, neuropathic pain and visceral pain.

In a fourth aspect of the invention, the present invention further relates to the use of at least one compound according to the first aspect of the present invention for the preparation of a pharmaceutical composition for the prophylaxis and/or treatment of disorders and/or diseases which are mediated, at least in part, by vanilloid receptors 1.

A fifth aspect of the present invention is a method for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further, a method of treatment and/or prophylaxis of disorders and/or diseases, which are mediated, at least in part, by vanilloid receptors 1, in a mammal, which comprises administering an effective amount of at least one compound according to the first aspect of the invention to the mammal.

A preferred embodiment of the fifth aspect of the invention is hence a method of treatment and/or prophylaxis of pain, preferably of pain selected from the group consisting of acute pain, chronic pain, neuropathic pain, visceral pain and joint pain, which comprises administering an effective amount of at least one compound according to the first aspect of the invention to the mammal.

The effectiveness against pain can be shown, for example, in the Bennett or Chung model (Bennett, G. J. and Xie, Y. K., Pain 1988, 33(1), 87-107; Kim, S. H. and Chung, J. M., Pain 1992, 50(3), 355-363), by tail flick experiments (e.g. D'Amour and Smith, J. Pharm. Exp. Ther. 1941, 72, 74-79) or by the formalin test (e.g. D. Dubuisson et al., Pain 1977, 4, 161-174).

EXAMPLES

The indication "equivalents" ("eq." or "eq" or "equiv." or "equiv") means molar equivalents, "RT" or "rt" means room temperature (23±7° C.), "M" are indications of concentration in mol/l, "aq." means aqueous, "sol." means solution.

Further abbreviations: conc.: concentrated; DBU: 1,8-Diazabicyclo[5.4.0]undec-7-ene; DCM: dichloromethane; DIBAL:diisobylaluminiumhydride; DMAP: 4-dimethyaminopyridine; DMS: dimethylsulfide; DMF: dimethylformamide; DPPA: diphenylphosphoryl azide; EDCl: 1-ethyl-3-(3-dimethylaminopropyl)carbodiimide hydrochloride; Et$_2$O: diethyl ether; EtOAc: ethyl acetate; EtOH: ethanol; h: hour(s); HOBt: hydroxybenzotriazole; KO$^t$Bu: potassium tert.-butanolate; LAH: lithium aluminium hydride; MeOH: methanol; MCPBA:m-chloroperbenzoic acid; min: minutes; PE: petroleum ether; PPh$_3$: triphenylphosphine; RM: reaction mixture; sat.: saturated; TBDM-SCl: tert-butyldimethylsilylchloirde; TEA: triethylamine; TFA: trifluoroacetic acid; THF: tetrahydrofuran; TLC: thin layer chromatography.

The yields of the compounds prepared were not optimized. All temperatures are uncorrected. All starting materials which are not explicitly described were either commercially available (the details of suppliers such as for example Acros, Avocado, Aldrich, Apollo, Bachem, Fluka, Fluoro-Chem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The stationary phase used for the column chromatography was silica gel 60 (0.04-0.063 mm) from E. Merck, Darmstadt. The mixing ratios of solvents or eluents for chromatography are specified in v/v. All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

Synthesis of Exemplary Compounds

In general, the 5-methylamino azoles INT-10 can be synthesized according to Scheme 1. In brief, thioamides INT-2a,b required for thiazole synthesis can be prepared by reacting the corresponding amides INT-1a,b with Lawesson's reagent.

Phenylethanone (INT-3) is reacted with dimethyl carbonate (4) to yield 3-oxopropanoates (INT-5). Oxidation of INT-5 with Dess-Martin periodinane in the presence of p-TsOH gives rise to methyl 3-oxo-2-(tosyloxy)propanoates (INT-6). Reaction of INT-6 with the amides INT-1 or thioamides INT-2 resulted in the oxazoles INT-7a,b-i and thiazoles INT-7-ab-ii, respectively. Reduction of the various INT-7 with LiAlH$_4$ yields the alcohols INT-8, which can be converted to the azides INT-9. Finally, Staudinger reduction with TPP in aqueous THF yields the 5-methylamino azoles INT-10, which were isolated as their hydrochlorides.

Scheme 1: Synthesis of methylamino azoles INT-10.

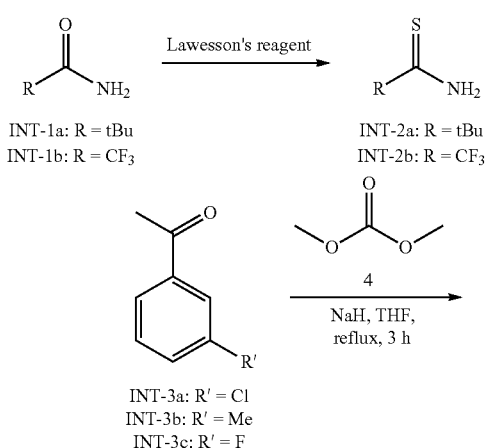

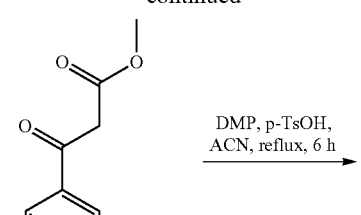

INT-5

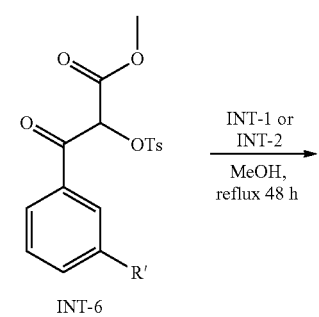

INT-6

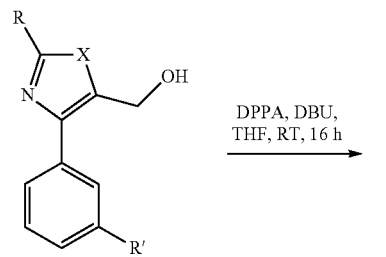

INT-7a-i: R = tBu, R' = Cl, X = O
INT-7a-ii: R = tBu, R' = Cl, X = S
INT-7a-iii: R = tBu, R' = Me, X = S
INT-7a-iv: R = tBu, R' = F, X = S
INT-7b-i: R = CF₃, X = O
INT-7b-ii: R = CF₃, X = S

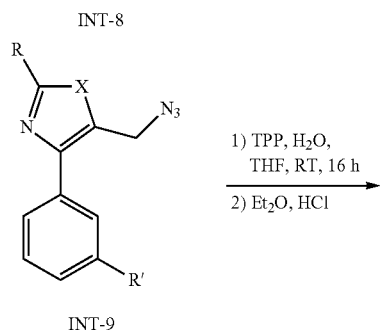

INT-8

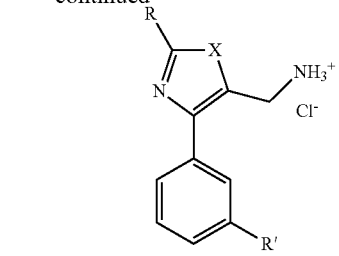

INT-9

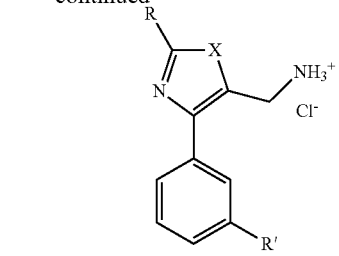

INT-10
INT-10a-i: R = tBu, R' = Cl, X = O
INT-10a-ii: R = tBu, R' = Cl, X = S
INT-10a-iii: R = tBu, R' = Me, X = S
INT-10a-iv: R = tBu, R' = F, X = S
INT-10b-i: R = CF₃, X = O
INT-10b-ii: R = CF₃, X = S Synthesis azole methylamine hydrochlorides INT-10

Synthesis of (2-(tert-butyl)-4-(3-chlorophenyl)thiazol-5-yl)methanamine hydrochloride (INT-10a-ii)

Synthesis of 2,2-dimethylpropanethioamide (INT-2a)

To a stirred solution of pivalamide (INT-1a, 5.0 g, 49.43 mmol, 1.0 eq) in THF (150 mL) was added Lawesson's reagents (29.9 g, 74.1 mmol, 1.5 eq) and the RM was stirred at 70° C. for 4 h. The RM was concentrated, diluted with Et$_2$O (30 mL) and washed with NaHCO$_3$ solution (30 mL), the organic layer was dried over MgSO$_4$ and concentrated under reduced pressure. The crude was washed with hexane (25 mL) to get 2,2-dimethylpropanethioamide (INT-2a, 4.0 g, 70%) which was used without further purification. TLC system: EtOAc/PE (7:3), R$_f$: 0.6

Synthesis of methyl 3-(3-chlorophenyl)-3-oxopropanoate (INT-5a)

To a stirred suspension of NaH (170 mg, 7.11 mmol, 1.1 eq) in THF (30 mL) at 0° C. was added 1-(3-chlorophenyl)ethanone (INT-3a, 1.00 g, 6.46 mmol, 1.0 eq) followed by dimethyl carbonate (4, 1.17 g, 12.9 mmol, 2.0 eq) and the RM was heated to reflux for 3 h. The RM was quenched with water (10 ml) and extracted with EtOAC (20 mL), the organic layer was dried over Na$_2$SO$_4$ filtered and evaporated to get methyl 3-(3-chlorophenyl)-3-oxopropanoate (INT-5a, 700 mg, 73%) which was used without further purification. TLC system: EtOAc/PE (3:2)

Synthesis of methyl 3-(3-chlorophenyl)-3-oxo-2-(tosyloxy)propanoate (INT-6a)

To a stirred solution of DMP (6.2 g, 14.1 mmol, 1.5 eq) in ACN (20 mL) was added p-TsOH (3.57 g, 18.8 mmol, 2.0 eq) followed by methyl 3-(3-chlorophenyl)-3-oxopropanoate (5, 2.0 g, 9.4 mmol, 1.0 eq) and the RM heated to reflux for 6 h. The RM was filtered, the filtrate was diluted with water (50 mL) and extracted with EtOAc (70 mL). The organic layer was washed with NaHCO$_3$ solution (30 mL), dried over anhydrous Na$_2$SO$_4$, concentrated and the resulting crude was purified by silica gel (100-200 mesh) column chromatography using EtOAc/PE (1:9) as an eluent to get methyl 3-(3-chlorophenyl)-3-oxo-2-(tosyloxy)propanoate (INT-6a, 1.0 g, 28%). TLC system: EtOAc/PE (2:3), $R_f$: 0.55

Synthesis of methyl 2-(tert-butyl)-4-(3-chlorophenyl)thiazole-5-carboxylate (INT-7a-ii)

To a stirred solution of methyl 3-(3-chlorophenyl)-3-oxo-2-(tosyloxy) (INT-6, 1.0 g, 2.6 mmol, 1.0 eq) in MeOH (10 mL) was 2,2-dimethylpropanethioamide (INT-2a, 0.367 g, 3.1 mmol, 1.2 eq) and the RM was heated to reflux for 16 h. The RM was concentrated under reduced pressure and the crude was purified by silica gel (100-200 mesh) column chromatography using EtOAc/PE (1:9) as eluent to get methyl 2-(tert-butyl)-4-(3-chlorophenyl)thiazole-5-carboxylate (INT-7a-ii, 0.450 g, 55%). TLC system: PE (2:3), $R_f$: 0.55

Synthesis of (2-(tert-butyl)-4-(3-chlorophenyl)thiazol-5-yl)methanol (INT-8a-ii)

To a stirred solution of methyl 2-(tert-butyl)-4-(3-chlorophenyl)thiazole-5-carboxylate (INT-7a-ii, 450 mg, 1.4 mmol, 1.0 eq) in THF (10 mL) was added LiAlH$_4$ (0.055 g, 1.4 mmol, 1.0 eq) at 0° C. and the RM was stirred at same temperature for 2 h. The RM was quenched with MeOH (2 mL), filtered through a pad of celite and concentrated under reduced to get (2-(tert-butyl)-4-(3-chlorophenyl)thiazol-5-yl)methanol (INT-8a-ii, 400 mg, 90%) as colorless liquid which was used without further purification. TLC system: EtOAc/PE (2:3), $R_f$: 0.4

Synthesis of 5-(azidomethyl)-2-(tert-butyl)-4-(3-chlorophenyl)thiazole (INT-9a-ii)

To a stirred solution of (2-(tert-butyl)-4-(3-chlorophenyl)thiazol-5-yl)methanol (INT-8a-ii, 400 mg, 1.36 mmol, 1.0 eq) in THF (10 mL) was added DBU (620 mg, 4.08 mmol, 3.0 eq) followed by DPPA (748 mg, 2.72 mmol, 2.0 eq) and the RM was stirred at RT for 16 h. The RM was concentrated and diluted with EtOAc (20 mL), washed with water (30 mL), dried over Na$_2$SO$_4$ and concentrated under reduced pressure. The crude was purified by silica gel column chromatography (100-200 mesh) using EtOAc/PE (1:9) as eluent to get 5-(azidomethyl)-2-(tert-butyl)-4-(3-chlorophenyl)thiazole (INT-9a-ii, 400 mg, 90%) as yellow liquid. TLC system: EtOAc/PE (2:8), $R_f$: 0.6

Synthesis (2-(tert-butyl)-4-(3-chlorophenyl)thiazol-5-yl)methanamine hydrochloride (INT-10a-ii)

To a stirred solution of 5-(azidomethyl)-2-(tert-butyl)-4-(3-chlorophenyl)thiazole (INT-9a-ii, 400 mg, 1.3 mmol, 1.0 eq) in THF (10 mL) was added TPP (685 mg, 2.6 mmol, 2.0 eq) followed by water (1.0 mL) and the RM was stirred at RT for 16 h. The RM was concentrated and the resulting crude was dissolved in toluene (10 mL) and extracted with 2N HCl (2×10 mL). The aqueous layer was basified with 2N NaOH and extracted with ether (3×10 mL). The organic layers were dried over Na$_2$SO$_4$ and HCl in ether was added to get (2-(tert-butyl)-4-(3-chlorophenyl)thiazol-5-yl)methanamine hydrochloride (INT-10a-ii, 300 mg, 80%) as a white solid. TLC system: MeOH/DCM (1:9), $R_f$: 0.4

The following azole methylamine hydrochlorides INT-10 were prepared according to the procedure described above.

TABLE 1

List of INT-10 prepared according to the procedure described for INT-10a-ii.

| | | |
|---|---|---|
| (2-(tert-butyl)-4-(3-chlorophenyl)oxazol-5-yl)methanamine hydrochloride | INT-10a-i | Using INT-1a instead of INT-2a |
| (4-(3-chlorophenyl)-2-(trifluoromethyl)oxazol-5-yl)methanamine hydrochloride | INT-10b-i | Using INT-1b instead of INT-2a |
| (4-(3-chlorophenyl)-2-(trifluoromethyl)thiazol-5-yl)methanamine hydrochloride | INT-10b-ii | Using INT-2b instead of INT-2a |
| (2-(tert-butyl)-4-(m-tolyl)thiazol-5-yl)methanaminium chloride | INT-10a-iii | Using INT-3b instead of INT-3a |
| (2-(tert-butyl)-4-(3-fluorophenyl)thiazol-5-yl)methanaminium chloride | INT-10a-iv | Using INT-3c instead of INT-3a |

Hydrochlorides INT-10 could be converted to the azole amides by coupling with the acids INT-11 in the presence of EDCl.HCl (Scheme 2).

Scheme 2: Synthesis of amides.

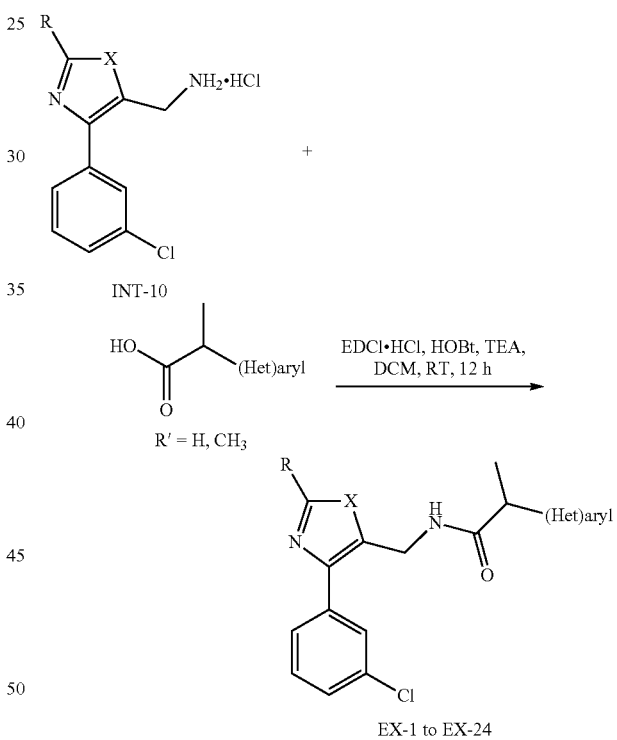

EX-1 to EX-24

The acids INT-10 used in this invention are summarized in Table 2.

TABLE 2

List of acids

| | | |
|---|---|---|
| 2-(3-fluoro-4-(2-hydroxyethyl)phenyl)propanoic acid | INT-11a | Synthesis see below |
| 2-(3-fluoro-4-(methylsulfonamidomethyl)phenyl)propanoic acid | INT-11b | Synthesized as described in US20130079373, pp. 15 |
| 2-(4-(((N-(tert-butoxycarbonyl)sulfamoyl)amino)methyl)phenyl)propanoic acid | INT-11c | Synthesized as described in US20130079377, pp. 39 |

TABLE 2-continued

List of acids

| | | |
|---|---|---|
| 2-(3-fluoro-4-(hydroxymethyl)phenyl)propanoic acid | INT-11d | Synthesis see below |
| 2-(4-(3-hydroxyoxetan-3-yl)phenyl)propanoic acid | INT-11e | Synthesis see below |
| 2-(5-fluoro-6-(2-(methylsulfonyl)ethyl)pyridin-3-yl)propanoic acid | INT-11f | Synthesis see below |
| 2-(6-((2-methoxyethyl)amino)pyridin-3-yl)propanoic acid | INT-11g | Synthesized as described in WO2013013817, pp. 115 |
| 2-(5-fluoro-6-(hydroxymethyl)pyridin-3-yl)propanoic acid | INT-11h | Synthesis see below |
| 2-(4-(((N-(tert-butoxycarbonyl)sulfamoyl)amino)methyl)-3-fluorophenyl)propanoic acid | INT-11i | Synthesis see below |

Synthesis of 2-(3-fluoro-4-(2-hydroxyethyl)phenyl) propanoic acid (INT-11a)

Synthesis of ethyl 2-(3-fluoro-4-nitrophenyl)propanoate

To a stirred solution of KO$^t$Bu (1.5 g, 7 mmol, 2 eq) in DMF (10 mL) was added a solution of 1-fluoro-2-nitrobenzene (1.0 g, 7.00 mmol, 1 eq) and ethyl 2-chloropropanoate (0.952 g, 7.00 mmol, 1 eq) dropwise at 0° C. The mixture was stirred for 30 min at 0° C. The RM was quenched with 1N HCl and extracted with Et$_2$O, dried (MgSO$_4$), and concentrated. The crude was purified by silica gel column chromatography (100-200 Mesh) using EtOAc/PE (1:19) to get ethyl 2-(3-fluoro-4-nitrophenyl)propanoate (800 mg, 47%) system: EtOAc/PE (1:9), R$_f$: 0.25

Synthesis of ethyl 2-(4-amino-3-fluorophenyl)propanoate

To a stirred solution of ethyl 2-(3-fluoro-4-nitrophenyl) propanoate (0.80 g, 3.3 mmol, 1.0 eq) in MeOH (20 mL) was added 10% Pd—C (0.2 g) and stirred under hydrogen atmosphere at RT for 1 h. The RM was filtered through celite pad and filtrate was concentrated under reduced pressure to get ethyl 2-(4-amino-3-fluorophenyl)propanoate (0.62 g, 88%) as a pale brown liquid. TLC system: EtOAc/PE (2:8), R$_f$: 0.2

Synthesis of ethyl 2-(3-fluoro-4-iodophenyl)propanoate

To a stirred solution of ethyl 2-(4-amino-3-fluorophenyl) propanoate (0.12 g, 0.56 mmol, 1.0 eq) and in conc.HCl (3 mL) was added NaNO$_2$ (0.078 g, 1.1 mmol, 2 eq) in water (5 mL) and stirred at −5° C. for 30 min. Then KI (0.466 g, 2.80 mmol, 5 eq), I$_2$ (0.576 g, 2.20 mmol, 4 eq) in water (5 mL) was added and stirred at same temperature for another 30 min. The RM was diluted with EtOAc, and washed with NaOCl solution, dried over Na$_2$SO$_4$ and concentrated to get ethyl 2-(3-fluoro-4-iodophenyl)propanoate (0.3 g, 43%). TLC system: EtOAc/PE (1:9), R$_f$: 0.5.

Synthesis of ethyl 2-(3-fluoro-4-vinylphenyl)propanoate

LiCl (490 mg, 11.6 mmol, 1.5 eq), Pd (PPh$_3$)$_4$ (444 mg, 0.38 mmol, 0.05 eq), were suspended in DMF (10 mL) and argon gas was purged into the solution for 15 min. The tributylvinyltin (3.6 g, 11.6 mmol, and 1.5 eq) and ethyl 2-(3-fluoro-4-iodophenyl)propanoate were added and heated to 55° C. for 16 h. The RM was filtered through a pad of celite and washed with EtOAc. The organic layer was washed with water, dried and concentrated. The crude was purified by column chromatography using 10% EtOAc in PE as an eluent to get ethyl 2-(3-fluoro-4-vinylphenyl)propanoate (1.1 g, 64%). TLC system: EtOAc/PE (1:9), R$_f$: 0.5

Synthesis of ethyl 2-(3-fluoro-4-(2-hydroxyethyl)phenyl)propanoate

To a stirred solution of ethyl 2-(3-fluoro-4-vinylphenyl) propanoate (150 mg, 0.9 mmol, 1.0 eq) in THF (2.5 mL) was added BH$_3$.DMS (0.18 mL, 1.6 mmol, 1.78 eq) at 0° C. and stirred at RT for 1 h. The RM was cooled to 0° C. the 1N NaOH (3 mL) and 30% H$_2$O$_2$ (2 mL) added and stirred for 30 min and at RT for another 30 min and extracted with EtOAc, dried over Na$_2$SO$_4$ and concentrated to get ethyl 2-(3-fluoro-4-(2-hydroxyethyl)phenyl)propanoate (240 mg crude). This crude was purified by column chromatography using 100-200 silica gel and 20% EtOAc in PE as an eluent to get ethyl 2-(3-fluoro-4-(2-hydroxyethyl)phenyl)propanoate (100 mg, 46%) as a colourless liquid. TLC system: EtOAc/PE (2:8), R$_f$: 0.25

Synthesis of 2-(3-fluoro-4-(2-hydroxyethyl)phenyl) propanoic acid (INT-11a)

To a stirred solution of ethyl 2-(3-fluoro-4-(2-hydroxyethyl)phenyl)propanoate (0.4 g, 1.6 mmol, 1.0 eq) in MeOH and H$_2$O (6 mL, 1:1) was added LiOH.H$_2$O (349 mg, 8.3 mmol, 5.0 eq) and stirred at RT for 2 h. The RM was concentrated and acidified with 2N HCl to get 2-(3-fluoro-4-(2-hydroxyethyl)phenyl)propanoic acid (INT-10a, 150 mg, 42%) as a colorless liquid. TLC system: EtOAc/PE (1:1), R$_f$: 0.2

Synthesis of 2-(3-fluoro-4-(hydroxymethyl)phenyl) propanoic acid (INT-11d)

Synthesis of (4-bromo-2-fluorophenyl)methanol

To a stirred solution of 4-bromo-2-fluoro benzaldehyde (15 g, 79.4 mmol) in MeOH (100 mL) at −5° C. to 0° C. was added NaBH$_4$ (6.0 g, 9 mmol) in portions and stirred at RT for 1 h until the starting material was completely consumed, as evidenced by TLC analysis. The RM was then diluted with ice cold water (100 mL) and concentrated under reduced pressure. The residue obtained on concentration was extracted with EtOAc (2×200 mL) and separated. The EtOAc layer was washed with brine (50 mL), dried over anhydrous NaSO$_4$, filtered and concentrated to afford (4-bromo-2-fluorophenyl)methanol (29 g, from 2 batches each of 15 g of of 4-bromo-2-fluoro benzaldehyde, 95%) as colorless oil. TLC system: EtOAcPE (3:7), R$_f$: 0.3

Synthesis of ((4-bromo-2-fluorobenzyl)oxy)(tert-butyl)dimethylsilane

A stirred solution of 4-bromo-2-fluoro benzaldehyde (49 g, 239 mmol, 1 eq) in DCM (400 mL) was treated with imidazole (32.5 g, 478 mmol, 2 eq) followed by TBDMS chloride (39.6 g, 263 mmol, 1.1 eq). The resulting solution was stirred at RT for 1 h, quenched with water (100 mL) and the layers were separated. The aqueous layer was extracted with DCM (2×100 mL). The combined organic layer was washed with brine (100 mL), dried (Na$_2$SO$_4$) and concentrated. The residue upon purification by column chromatography (silica gel 100-200, EtOAc/PE; 10:90) afforded ((4-bromo-2-fluorobenzyl)oxy)(tert-butyl)dimethylsilane (53 g, 70%) as a brown liquid. TLC system: EtOAc/PE (1:9), R$_f$: 0.6

Synthesis of tert-butyl((2-fluoro-4-(4,4,5,5-tetramethyl-1,3,2-dioxaborolan-2-yl)benzyl)oxy)dimethylsilane To a stirred solution of ((4-bromo-2-fluorobenzyl)oxy)(tert-butyl)dimethylsilane (1.2 g, 3.7 mmol, 1 eq) in 1,4-dioxane (10 mL) was treated with bis-pinacolato diboron (1.05 g, 4.15 mmol, 1.1 eq) and KOAc (0.74 g, 7.5 mmol, 2 eq) at RT. The RM was purged with Ar for 20 min. Pd(PPh$_3$)$_2$Cl$_2$ (0.26 g, 0.37 mmol, 0.1 eq) was then added and the RM was again purged with Ar for an additional 15 min. The RM was heated to 100° C. for 3 h until complete consumption of starting material, as evidenced by TLC analysis. The RM was concentrated and the obtained crude compound was purified by column chromatography (60-120 mesh) using PE as eluent to afford tert-butyl((2-fluoro-4-(4,4,5,5-tetramethyl-1,3,2-dioxaborolan-2-yl)benzyl)oxy)dimethylsilane (1 g, 74%) as a pale yellow oil. TLC solvent system: EtOAc/PE (1:9), Rf: 0.7

Synthesis of benzyl 2-bromoacrylate

A suspension of 2-bromoacrylic acid (25.0 g, 167 mmol), BnBr (21.8 mL, 183 mmol) and K$_2$CO$_3$ (46 g, 0.33 mol) in acetonitrile (250 mL) was stirred at 80° C. for 3 h until complete consumption of starting material, as evidenced by TLC analysis. The RM was filtered and concentrated. The obtained crude compound was purified by column chromatography (100-200 mesh silica gel) using EtOAc/PE (5:95) as eluent to afford benzyl 2-bromoacrylate (22 g, 53%) as a yellow liquid. (TLC solvent system: EtOAc/PE (5:95), Rf: 0.7

Synthesis of benzyl 2-(4-(((tert-butyldimethylsilyl)oxy)methyl)-3-fluorophenyl)acrylate A suspension of tert-butyl((2-fluoro-4-(4,4,5,5-tetramethyl-1,3,2-dioxaborolan-2-yl)benzyl)oxy)dimethylsilane (500 mg, 1.36 mmol, 1 eq), Cs$_2$CO$_3$ (1.3 g, 4.1 mmol, 3 eq) in DMF (5 mL) was deoxygenated by purging Ar for 30 min at RT. Pd(dppf)Cl$_2$ (55.6 mg, 0.068 mmol, 0.04 eq) was added and purging continued. After 10 min, benzyl 2-bromoacrylate (497 mg, 2.05 mmol, 1.5 eq) was added and stirred at 100° C. for 2 h until complete consumption boronate, as evidenced by TLC analysis. The RM was diluted with EtOAc (10 mL), filtered through celite and washed with EtOAc (20 mL). The combined filtrate was washed with water (3×20 mL), brine (50 mL), dried over anhydrous Na$_2$SO$_4$, filtered and concentrated. The obtained crude compound was purified by column chromatography (100-200 mesh silica gel) using 5% EtOAc in PE as eluent to afford benzyl 2-(4-(((tert-butyldimethylsilyl)oxy)methyl)-3-fluorophenyl)acrylate (200 mg, 42%) as a pale brown oil. TLC system: EtOAc/PE (1:9), Rf: 0.65

Synthesis of 2-(3-fluoro-4-(hydroxymethyl)phenyl)propanoic acid (INT-11d)

A suspension of benzyl 2-(4-(((tert-butyldimethylsilyl)oxy)methyl)-3-fluorophenyl)acrylate (20 mg, 0.050 mmol), 10% Pd(OH)$_2$ (4 mg) and 10% Pd—C (4 mg) in EtOH (1 mL) was hydrogenated (balloon pressure) at RT for 16 h until complete consumption of starting material, as evidenced by TLC analysis. The RM was filtered through Celite, washed with MeOH (2×10 mL). The combined filtrate was concentrated and the obtained crude compound was purified by dissolving in EtOAc (20 mL) and shaken with aq 10% NaHCO$_3$ solution (15 mL). The EtOAc layer was separated; the aq layer was acidified with aq citric acid solution (pH 5) and extracted with EtOAc (2×20 mL). The combined EtOAc layer was washed with water (15 mL), brine (15 mL) dried over anhydrous Na$_2$SO$_4$, filtered and concentrated to afford 2-(3-fluoro-4-(hydroxymethyl)phenyl)propanoic acid (INT-11d, 6.7 mg, 69%; colorless oil). TLC solvent system: EtOAc/PE (6:4), Rf: 0.2

Synthesis of 2-(4-(3-hydroxyoxetan-3-yl)phenyl)propanoic acid (INT-11e)

Synthesis of 3-(4-bromophenyl)oxetan-3-ol

To a stirred solution of 1,4-dibromobenzene (5.00 g, 21.4 mmol) in THF (40 mL) at −78° C. was added n-BuLi (8.5 mL, 21.4 mmol, 2.5 M solution in hexane), stirred for 30 min and added a solution of oxetan-3-one (1.25 mL, 21.4 mmol) in THF (10 mL) over a period of 15 min. The resultant RM was allowed to warm to RT and stirred for 3 h. The RM was cooled to 0° C., quenched with aq.NH$_4$Cl solution, diluted with water (30 mL) and extracted with EtOAc (2×50 mL), washed with brine (20 mL), dried over Na$_2$SO$_4$ and evaporated to get the crude compound. The crude was purified by silica gel (100-200 mesh) column chromatography using EtOAc/PE (1:9) as an eluent to get 3-(4-bromophenyl)oxetan-3-ol (3.0 g, 60%). TLC system: EtOAc/PE (1:4), R$_f$: 0.2

Synthesis of 3-(4-(4,4,5,5-tetramethyl-1,3,2-dioxaborolan-2-yl)phenyl)oxetan-3-ol To a degassed solution of 3-(4-bromophenyl)oxetan-3-ol (0.500 g, 2.20 mmol), bis(pinacolato)diboron (0.61 g, 2.41 mmol) in 1,4-dioxane (10 mL) under Ar was added KOAc (0.65 g, 6.60 mmol) followed by PdCl$_2$(dppf).DCM complex (0.09 g, 0.11 mmol) and degassed for 30 min. The resultant RM was heated at 100° C. for 2 h. The RM was evaporated under reduced pressure and the crude was triturated with EtOAc/PE (3:7), filtered hot through a pad of neutral alumina and evaporated to get crude compound. The crude was triturated with pentane, filtered and dried under vacuum to get 3-(4-(4,4,5,5-tetramethyl-1,3,2-dioxaborolan-2-yl)phenyl)oxetan-3-ol (0.42 g, 70%). TLC system: EtOAc/hexane (1:1), R$_f$: 0.4

Synthesis of benzyl 2-(4-(3-hydroxyoxetan-3-yl)phenyl)acrylate

To a degassed solution of cesium carbonate (0.94 g, 2.9 mmol) in 1,4-dioxane (10 mL), water (1 mL) under Ar was added benzyl 2-bromoacrylate (0.35 g, 1.5 mmol, synthesis: see above), 3-(4-(4,4,5,5-tetramethyl-1,3,2-dioxaborolan-2-yl)phenyl)oxetan-3-ol (0.40 g, 1.5 mmol) followed by Pd(PPh$_3$)$_4$ (0.085 g, 0.073 mmol), degassed for 30 min and heated at 100° C. for 4 h. The RM was evaporated under reduced pressure and the crude was diluted with water (10 mL), extracted with EtOAc (2×20 mL), washed with brine (10 mL), dried over Na$_2$SO$_4$ and evaporated the solvent to get crude compound. The crude was purified by silica gel column chromatography (100-200 mesh) using EtOAc/PE (3:7) as eluent to get benzyl 2-(4-(3-hydroxyoxetan-3-yl) phenyl)acrylate (0.36 g, ~80%). TLC system: EtOAc/PE (1:1), $R_f$: 0.3

Synthesis of 2-(4-(3-hydroxyoxetan-3-yl)phenyl) propanoic acid (INT-11e)

A solution of benzyl 2-(4-(3-hydroxyoxetan-3-yl)phenyl) acrylate (0.35 g, 1.1 mmol) in EtOH (5 mL) was hydrogenated under hydrogen balloon atmosphere with 10% Pd/C (70 mg) at RT for 4 h. The RM was filtered through celite pad, washed with EtOH and the solvent was evaporated under reduced pressure. The residue was dried under vacuum to get crude 2-(4-(3-hydroxyoxetan-3-yl)phenyl) propanoic acid (INT-11e, 0.25 g) which was used without further purification. TLC system: 100% EtOAc, $R_f$: 0.05

Synthesis of 2-(5-fluoro-6-(2-(methylsulfonyl)ethyl) pyridin-3-yl)propanoic acid (INT-11f)

Synthesis of 5-bromo-3-fluoro-2-vinylpyridine

To a degassed solution of 2,5-dibromo-3-fluoropyridine (0.500 g, 1.97 mmol), tributyl (vinyl) tin (0.70 mL, 2.4 mmol) in anhydrous DMF (5 mL) under Ar was added LiCl (0.12 g, 2.95 mmol), followed by Pd(PPh$_3$)$_4$ (0.12 g, 0.098 mmol). The mixture was degassed for 30 min and heated at 60° C. for 16 h. The RM was filtered through celite pad, diluted with water (10 mL) and extracted with Et$_2$O (2×20 mL), washed with brine (10 mL), dried over Na$_2$SO$_4$ and evaporated to get the crude compound. The crude was purified by silica gel (100-200 mesh) column chromatography using 2% EtOAc/PE as an eluent to get crude 5-bromo-3-fluoro-2-vinylpyridine (0.30 g) which was used without further purification. TLC system: EtOAc/PE (1:9), $R_f$: 0.8

Synthesis of 5-bromo-3-fluoro-2-(2-(methylsulfonyl)ethyl)pyridine

To a stirred solution of 5-bromo-3-fluoro-2-vinylpyridine (0.30 g, 1.5 mmol) in EtOH (5 mL) was added sodium methanesulfinate (0.46 g, 4.5 mmol) followed by trifluoroacetic acid (0.33 mL, 4.5 mmol) and heated at 60° C. for 2 h. The RM was cooled, diluted with water (10 mL) and basified with 10% NaHCO$_3$, extracted with DCM (2×25 mL), washed with brine (10 mL), dried over Na$_2$SO$_4$ and evaporated to get crude compound. The crude was triturated with pentane, filtered and dried under vacuum to get 5-bromo-3-fluoro-2-(2-(methylsulfonyl)ethyl)pyridine (130 mg, 23% over 2 steps). TLC system: EtOAc/PE (1:1), $R_f$: 0.3

Synthesis of 3-fluoro-2-(2-(methylsulfonyl)ethyl)-5-(4,4,5,5-tetramethyl-1,3,2-dioxaborolan-2-yl)pyridine To a degassed solution of 5-bromo-3-fluoro-2-(2-(methylsulfonyl)ethyl)pyridine (0.25 g, 0.89 mmol), bis(pinacolato)diboron (0.23 g, 0.89 mmol) in 1,4-dioxane (10 mL) under Ar was added KOAc (0.26 g, 2.7 mmol) followed by PdCl$_2$(dppf).DCM complex (0.075 g, 0.089 mmol). The RM was degassed for 30 min and heated at 100° C. for 2 h. The RM was concentrated under reduced pressure and the crude was triturated with EtOAc/PE (3:7), filtered through a pad of neutral alumina and evaporated. The crude product was triturated with pentane, filtered the solid and dried under vacuum to get 3-fluoro-2-(2-(methylsulfonyl)ethyl)-5-(4,4, 5,5-tetramethyl-1,3,2-dioxaborolan-2-yl)pyridine (0.15 g, 51%). TLC system: EtOAc/hexane (3:7), $R_f$: 0.05

Synthesis of benzyl 2-(5-fluoro-6-(2-(methylsulfonyl)ethyl)pyridin-3-yl)acrylate To a degassed solution of cesium carbonate (0.54 g, 1.7 mmol) in 1,4-dioxane (5 mL) and water (1 mL) under Ar was added benzyl 2-bromoacrylate (0.20 g, 0.83 mmol, synthesis: see above), 3-fluoro-2-(2-(methylsulfonyl)ethyl)-5-(4,4, 5,5-tetramethyl-1,3,2-dioxaborolan-2-yl)pyridine (0.30 g, 0.91 mmol) followed by Pd(PPh$_3$)$_4$ (0.050 g, 0.040 mmol), degassed for 30 min and heated at 100° C. for 2 h. The RM was filtered through a pad of celite, the solvent was evaporated under reduced pressure and the crude was diluted with water (10 mL), extracted with EtOAc (2×20 mL), washed with brine (10 mL), dried over Na$_2$SO$_4$ and evaporated. The crude was purified by silica gel column chromatography (100-200 mesh) using EtOAc/PE (1:1) as eluent to get benzyl 2-(5-fluoro-6-(2-(methylsulfonyl)ethyl)pyridin-3-yl) acrylate (0.21 g, 70%). TLC system: EtOAc/PE (1:1), $R_f$: 0.2

Synthesis of 2-(5-fluoro-6-(2-(methylsulfonyl)ethyl) pyridin-3-yl)propanoic acid (INT-11f)

A solution of 2-(5-fluoro-6-(2-(methylsulfonyl)ethyl) pyridin-3-yl)acrylate (0.20 g, 0.55 mmol), 10% Pd/C (50 mg) in EtOH (5 mL) was hydrogenated under hydrogen balloon atmosphere at RT for 3 h. The RM was filtered through celite pad, washed with EtOH and the solvent was evaporated under reduced pressure and dried under vacuum to get crude 2-(5-fluoro-6-(2-(methylsulfonyl)ethyl)pyridin-3-yl)propanoic acid (INT-11f, 0.10 g). The compound was used without further purification. TLC system: MeOH/DCM (1:9), $R_f$: 0.05

Synthesis of 2-(5-fluoro-6-(hydroxymethyl)pyridin-3-yl)propanoic acid (INT-11h)

Synthesis of ethyl 2, 6-dichloro-5-fluoronicotinate

Thionyl chloride (50.0 mL, 655 mmol) was added to a stirred solution of 2,6-dichloro,5-fluoro,3-nicotinic acid (55.0 g, 262 mmol) in EtOH (300 mL) at 0° C. The resulting RM was stirred at reflux for 16 h. The RM was cooled to RT. EtOH was evaporated in vacuo; crude compound was dissolved in sat NaHCO$_3$ solution (300 mL) and extracted with EtOAc (3×200 mL). Combined organic layers were washed with water, brine (200 mL), dried (Na$_2$SO$_4$) and concentrated to give ethyl 2,6-dichloro-5-fluoronicotinate (61 g, 98%) as a light brown oil which was used without further purification. TLC System: EtOAc/PE (1:1), $R_f$: 0.6).

Synthesis of diethyl 2-(6-chloro-5-(ethoxycarbonyl)-3-fluoropyridin-2-yl)malonate Diethyl malonate (48.0 mL, 311 mmol) was added drop wise to a suspension of NaH (60% in mineral oil; 10.3 g, 259 mmol) in DMF (150 mL) at 0° C., stirred at RT for 1 h. A solution of ethyl 2,6-dichloro-5-fluoronicotinate (62.0 g, 259. mmol) in DMF (100 mL) was added at 0° C. and the whole stirred at 50° C. for 16 h. The RM was quenched with sat NH$_4$Cl (200 mL) solution and extracted with EtOAc (3×300 mL). Combined organic layer was washed successively with water, brine (200 mL), dried (Na$_2$SO$_4$) and concentrated to give crude compound, which was purified by silica gel column chromatography eluting 5% EtOAc in PE to give diethyl 2-(6-chloro-5-(ethoxycarbonyl)-3-fluoropyridin-2-yl)malonate (90.0 g, 96%) as light yellow oil. TLC system: EtOAc/PE (1:9); $R_f$: 0.4

Synthesis of diethyl 2-(5-(ethoxycarbonyl)-3-fluoropyridin-2-yl)malonate

10% palladium hydroxide (9.0 g) was added to a degassed solution of diethyl 2-(6-chloro-5-(ethoxycarbonyl)-3-fluoropyridin-2-yl)malonate (90.0 g, 249 mmol) and triethyl amine (70.0 mL, 499 mmol) in EtOH (450 mL) at RT. The RM was hydrogenated at RT and 20 psi for 2 h. RM was filtered through celite bed, washed with excess EtOH, concentrated to give crude compound, which was dissolved in water and extracted with EtOAc (2×100 mL). Combined organic layer was washed with water (100 mL), brine (50 mL), dried ($Na_2SO_4$) and concentrated to give diethyl 2-(5-(ethoxycarbonyl)-3-fluoropyridin-2-yl)malonate (80.0 g, 98%) as light yellow oil. TLC system: EtOAc/PE (1:9), $R_f$: 0.4)

Synthesis of 5-fluoro-6-methylnicotinic acid hydrochloride

Conc. HCl (400 mL) was added to diethyl 2-(5-(ethoxycarbonyl)-3-fluoropyridin-2-yl)malonate (80.0 g, 245 mmol) at 0° C. The resulting RM was stirred at 120° C. for 24 h. The RM was cooled to RT and aqueous layer was evaporated under reduced pressure, azeotropically dried with toluene to give 5-fluoro-6-methylnicotinic acid hydrochloride (45 g, 96%) as light yellow solid. TLC System: MeOH/DCM (1:9), $R_f$: 0.5

Synthesis of ethyl 5-fluoro-6-methylnicotinate

Thionyl chloride (53.0 mL, 711 mmoles) was added to a stirred solution of 5-fluoro-6-methylnicotinic acid hydrochloride (45.0 g, 237 mmol) in EtOH (250 mL) at 0° C. The resulting RM was stirred at reflux for 16 h. The RM was cooled to RT, EtOH was evaporated, crude compound was dissolved in sat $NaHCO_3$ solution (200 mL) and extracted with EtOAc (3×200 mL). Combined organic layers were washed with water, brine (200 mL), dried ($Na_2SO_4$) and concentrated to give ethyl 5-fluoro-6-methylnicotinate (40.0 g, 92%) as a light brown oil which was used in next without further purification. TLC System: EtOAc/PE (1:1), $R_f$: 0.6

Synthesis of (5-fluoro-6-methylpyridin-3-yl)methanol $NaBH_4$ (24.9 g, 655.73 mmoles) was added to a stirred solution of ethyl 5-fluoro-6-methylnicotinate (40.0 g, 219 mmol) in EtOH (400 mL) at 0° C. The resulting RM was stirred at RT for 16 h, EtOH was evaporated, crude compound was dissolved in water (200 mL) and extracted with EtOAc (3×200 mL). Combined organic layers were washed with water, brine (200 mL), dried ($Na_2SO_4$) and concentrated to give (5-fluoro-6-methylpyridin-3-yl)methanol (30 g, 96%) as a light brown oil which was used without further purification. TLC System: EtOAc/PE (1:1), $R_f$: 0.2

Synthesis of 5-(chloromethyl)-3-fluoro-2-methylpyridine

Thionyl chloride (150 mL) was added to (5-fluoro-6-methylpyridin-3-yl)methanol (30.0 g, 213 mmol) at 0° C. The resulting RM was stirred at reflux for 6 h. Thionyl chloride was evaporated in vacuo; the residue was dissolved in sat $NaHCO_3$ solution (200 mL) and extracted with EtOAc (3×200 mL). Combined organic layers were washed with brine (200 mL), dried ($Na_2SO_4$) and concentrated to give 5-(chloromethyl)-3-fluoro-2-methylpyridine (28 g, 82%) as a brown oil which was used without further purification. TLC System: EtOAc/PE (1:1), $R_f$: 0.5

Synthesis of 2-(5-fluoro-6-methylpyridin-3-yl)acetonitrile

Sodium cyanide (18.0 g, 352 mmoles) was added to a stirred solution of 5-(chloromethyl)-3-fluoro-2-methylpyridine (28.0 g, 176 mmol) in mixture of EtOH/water (200/20 mL) at 0° C. The resulting RM was stirred at reflux for 6 h. The RM was cooled to RT, quenched with ice cold water (300 mL) and extracted with EtOAc (3×500 mL). Combined organic layers were washed with water, brine (300 mL), dried ($Na_2SO_4$) and concentrated to give crude 2-(5-fluoro-6-methylpyridin-3-yl)acetonitrile (24.0 g, 90%) as a brown oil which was used without further purification. TLC system: EtOAc/PE (1:1), $R_f$: 0.35

Synthesis of Methyl 2-(5-fluoro-6-methylpyridin-3-yl)acetate

Trimethylsilyl chloride (100 mL, 800 mmol) was added to a stirred solution of 2-(5-fluoro-6-methylpyridin-3-yl)acetonitrile (24.0 g, 160 mmol) in MeOH (300 mL) at 0° C. The resulting RM was stirred at 90° C. for 8 h in a sealed tube. The RM was cooled to RT. MeOH was evaporated; crude compound was dissolved in sat $NaHCO_3$ solution (200 mL) and extracted with EtOAc (3×200 mL). Combined organic layers were washed with water, brine (200 mL), dried ($Na_2SO_4$) and concentrated to get crude, which was purified by silica gel column chromatography eluting with 20% EtOAc in PE to get methyl 2-(5-fluoro-6-methylpyridin-3-yl)acetate (22.0 g, 75%) as light yellow oil. TLC system: EtOAc/PE (1:1), $R_f$: 0.50)

Synthesis of methyl 2-(5-fluoro-6-methylpyridin-3-yl)propanoate

A solution of methyl 2-(5-fluoro-6-methylpyridin-3-yl)acetate (22.0 g, 120 mmol) in THF (200 mL) was added drop wise to a suspension of 60% NaH (4.80 g, 120 mmol) in THF (150 mL) at 0° C., stirred at same temperature for 15 min and then a solution of methyl iodide (7.75 mL, 120 mmol) in THF (100 mL) was added at 0° C. and the RM was stirred at 0° C. for 2 h. The RM was quenched with sat $NH_4Cl$ (100 mL) and extracted with EtOAc (3×200 mL). Combined organic layers were washed with water, brine (200 mL), dried ($Na_2SO_4$) and concentrated to give crude, which was purified by silica gel column chromatography eluting 5% EtOAc in PE to give methyl 2-(5-fluoro-6-methylpyridin-3-yl)propanoate (10.0 g, 44%) as a light yellow oil. TLC system: EtOAc/PE (1:1), $R_f$: 0.68

Synthesis of methyl 2-(5-fluoro-6-methylpyridin-3-yl)propanoate N-oxide

MCPBA (10.4 g, 60.9 mmol) was added to a stirred solution of methyl 2-(5-fluoro-6-methylpyridin-3-yl)propanoate (10.0 g, 50.8 mmol) in chloroform (200 mL) at 0° C. The resulting RM was stirred at RT for 4 h. The RM was diluted with chloroform and successively washed with sat $NaHCO_3$ solution (200 mL), water, brine (200 mL), dried ($Na_2SO_4$) and concentrated to give methyl 2-(5-fluoro-6-methylpyridin-3-yl)propanoate N-oxide (11.0 g) as a light yellow oil which was used without further purification. TLC system: EtOAc/PE (1:1), $R_f$: 0.1

Synthesis of methyl 2-(6-(acetoxymethyl)-5-fluoro-pyridin-3-yl)propanoate

Acetic anhydride (110 mL) was added to 2-(5-fluoro-6-methylpyridin-3-yl)propanoate N-oxide (11.0 g, 51.6 mmol) at 0° C. The resulting RM was stirred at reflux for 4 h, cooled to RT and quenched with ice cold water. Basified with solid $NaHCO_3$ and extracted with EtOAc (3×200 mL). Combined organic layers were washed with water, brine (200 mL), dried ($Na_2SO_4$) and concentrated to get crude, which was purified by neutral alumina eluting with 5% EtOAc in PE to get methyl 2-(6-(acetoxymethyl)-5-fluoropyridin-3-yl)propanoate (5.5 g, 42% over 2 steps) as a light yellow oil. TLC system: EtOAc/PE (1:1), $R_f$: 0.58

Synthesis of 2-(5-fluoro-6-(hydroxymethyl)pyridin-3-yl)propanoic acid (INT-11h)

Conc. HCl (60.0 mL) was added to 2-(6-(acetoxymethyl)-5-fluoropyridin-3-yl)propanoate (5.5 g, 21.6 mmol) at 0° C. The resulting RM was stirred at RT for 5 h. The water was evaporated under reduced pressure. Resulting crude was redissolved in conc. HCl (60 mL) and stirred at RT for 10 h. The solvent was evaporated under reduced pressure and azeotropically dried with toluene to give 2-(5-fluoro-6-(hydroxymethyl)pyridin-3-yl)propanoic acid (INT-11h, 3.5 g, 83%) as an off white sticky solid which was used without further purification. TLC System: (MeOH/DCM (15:85), $R_f$: 0.33

Synthesis of 2-(4-(((N-(tert-butoxycarbonyl)sulfamoyl)amino)methyl)-3-fluorophenyl)propanoic acid (INT-11i)

Synthesis of ethyl 2-(3-fluoro-4-nitrophenyl)propanoate

To a stirred solution of KO$^t$Bu (16.0 g, 142 mmol, 2 eq) in DMF (100 mL) were added a mixture of 1-fluoro-2-nitrobenzene (10.0 g, 70.9 mmol, 1.0 eq) and ethyl 2-chloropropanoate (9.0 mL, 70.9 mmol, 1.0 eq) at −50° C. and stirred for 10 min at 0° C. The RM was cooled to −40° C. and quenched with 2N HCl, diluted with water (100 mL), extracted into EtOAc (2×200 mL), dried over $Na_2SO_4$ and evaporated under reduced pressure. The crude was purified by silica gel (60-120 mesh) column chromatography using 2-5% EtOAc in PE as eluent to get ethyl 2-(3-fluoro-4-nitrophenyl)propanoate (10 g, 58%) as a yellow liquid. TLC system: 10% EtOAc in PE, $R_f$: 0.4

Synthesis of ethyl 2-(4-amino-3-fluorophenyl)propanoate

To a stirred solution of ethyl 2-(3-fluoro-4-nitrophenyl) propanoate (9.00 g, 37.3 mmol, 1.0 eq) in MeOH (70 mL) was added 10% Pd—C (4.0 g) and the RM was stirred for 1 h at RT under hydrogen atmosphere (50 psi). The RM filtered through celite bed and evaporated to get ethyl 2-(4-amino-3-fluorophenyl)propanoate (7.0 g, 88%) as a light brown liquid which was used without further purification. TLC system: 10% EtOAc in PE, $R_f$: 0.1

Synthesis of ethyl 2-(3-fluoro-4-iodophenyl)propanoate

To a stirred solution of p-TsOH (20.2 g, 106 mmol, 3 eq) in ACN (100 mL) was added ethyl 2-(4-amino-3-fluorophenyl)propanoate (7.50 g, 35.5 mmol, 1.0 eq) at 0° C., stirred for 10 min and added a mixture of KI (14.8 g, 88.9 mmol, 2.5 eq.), $NaNO_2$ (4.90 g, 71.1 mmol, 2 eq) in water (20 mL). The RM was stirred for 2 h at RT, diluted with water (200 mL), neutralized with sat. $NaHCO_3$ and extracted with EtOAc (2×30 mL). The organic layer was washed with brine (20 mL), dried over $Na_2SO_4$ and evaporated under reduced pressure. The crude compound was purified by silica gel (60-120 mesh) column chromatography using 2-3% EtOAc in PE as eluent to get ethyl 2-(3-fluoro-4-iodophenyl)propanoate (6.5 g, 65%) as a pale yellow liquid. TLC system: 10% EtOAc in PE $R_f$: 0.6

Synthesis of ethyl 2-(4-cyano-3-fluorophenyl)propanoate

To a stirred solution of ethyl 2-(3-fluoro-4-iodophenyl) propanoate (6.8 g, 21.1 mmol, 1.0 eq) in NMP (50 mL) was added CuCN (1.84 g, 21.1 mmol, 1.0 eq) and stirred for 3 h at 180° C. The RM was diluted with water (100 mL) and extracted into EtOAc (2×50 mL). The organic layer was washed with brine (30 mL), dried over $Na_2SO_4$ and concentrated under reduced pressure. The crude was purified by silica gel (60-120) column chromatography using 5-10% EtOAc in PE as eluent to get ethyl 2-(4-cyano-3-fluorophenyl)propanoate (4.5 g, 90%) as a black colour liquid. TLC system: 10% EtOAc in PE, $R_f$: 0.4

Synthesis of ethyl 2-(4-(aminomethyl)-3-fluorophenyl)propanoate

To a stirred solution of ethyl 2-(4-cyano-3-fluorophenyl) propanoate (4.50 g, 20.4 mmol, 1.0 eq) in EtOH (40 mL) were added Raney-Ni (2.0 g) followed by aq. $NH_3$ (2 mL) and the mixture was stirred for 2 h at RT under hydrogen atmosphere (50 psi). The RM was filtered through celite pad and the filtrate was evaporated under reduced pressure. The crude product was co-distilled twice with toluene to get ethyl 2-(4-(aminomethyl)-3-fluorophenyl)propanoate (3.0 g, 75%) as a pale green liquid. TLC system: EtOAc/PE (1:5), $R_f$: 0.05

Synthesis of ethyl 2-(4-(((N-(tert-butoxycarbonyl) sulfamoyl)amino)methyl)-3-fluorophenyl)propanoate To a stirred solution of t-BuOH (4.27 mL, 44.4 mmol, 2.5 eq) in DCM (10 mL) at RT was added Sulfuryl chloride isocyanate (3.13 mL, 35.4 mmol, 2.0 eq) and stirred at RT for 1 h. This RM was added to a solution of ethyl 2-(4-(aminomethyl)-3-fluorophenyl)propanoate (4.00 g, 17.7 mmol, 1.0 eq), TEA (7.4 mL, 53 mmol, 3.0 eq) in DCM at 50° C. and refluxed for 2 h. The RM was diluted with water (50 mL), extracted with DCM (2×50 mL), dried over $Na_2SO_4$ and evaporated to get crude ethyl 2-(4-(((N-(tert-butoxycarbonyl)sulfamoyl)amino)methyl)-3-fluorophenyl) propanoate (2.0 g) as an off white solid which was used without further purification. TLC system: EtOAc/PE (1:1), $R_f$: 0.6

Synthesis of 2-(4-(((N-(tert-butoxycarbonyl)sulfamoyl)amino)methyl)-3-fluorophenyl)propanoic acid (INT-11i)

To a stirred solution of ethyl 2-(4-(((N-(tert-butoxycarbonyl)sulfamoyl)amino)methyl)-3-fluorophenyl)propanoate (4.0 g, 9.9 mmol, 1.0 eq) in MeOH (20 mL) and H$_2$O (20 mL) was added LiOH.H$_2$O (2.0 g, 50 mmol, 5.0 eq) and the mixture was stirred for 16 h at RT. The RM was evaporated, acidified with 10% citric acid solution (~pH 5), extracted with EtOAc (2×50 mL). The organic layer was dried over Na$_2$SO$_4$ and evaporated under reduced pressure. The crude was washed with n-pentane to get 2-(4-(((N-(tert-butoxycarbonyl)sulfamoyl)amino)methyl)-3-fluorophenyl)propanoic acid (INT-11i, 1.5 g, 39%) as white solid. TLC system: EtOAc/PE (1:1), R$_f$: 0.25

Synthesis of Azole Amides

Synthesis of N-((4-(3-chlorophenyl)-2-(trifluoromethyl)thiazol-5-yl)methyl)-2-(3-fluoro-4-(2-hydroxyethyl)phenyl)propanamide (EX-1)

To a stirred solution of 2-(3-fluoro-4-(2-hydroxyethyl)phenyl)propanoic acid (INT-11a, 100 mg, 0.36 mmol, 1.0 eq) in DCM at 0° C. were added EDC.HCl (107 mg, 0.56 mmol, 1.2 eq), HOBT (76 mg, 0.56 mmol, 1.2 eq), TEA (0.203 mL, 1.4 mmol, 3.0 eq) and (4-(3-chlorophenyl)-2-(trifluoromethyl)thiazol-5-yl)methanamine hydrochloride (INT-10b-ii, 154 mg, 0.47 mmol, 1.0 eq) and stirred at RT for 12 h. The RM was diluted with water (10 mL) and extracted with DCM (10 mL), dried (Na$_2$SO$_4$) and evaporated. The resulting crude was purified by silica gel column chromatography (100-200) using EtOAc/PE (3:7) to get N-((4-(3-chlorophenyl)-2-(trifluoromethyl)thiazol-5-yl)methyl)-2-(3-fluoro-4-(2-hydroxyethyl)phenyl)propanamide (EX-1, 72 mg, 33%) as a pale yellow solid. TLC system: EtOAc/PE (1:1), R$_f$: 0.65; ESI (m/z, MH$^+$): 487.0

According to the procedure described for EX-1, the following amides were prepared:

N-((4-(3-chlorophenyl)-2-(trifluoromethyl)oxazol-5-yl)methyl)-2-(3-fluoro-4-(2-hydroxyethyl)phenyl)propanamide (EX-2) from INT-10b-i and INT-11a. TLC system: EtOAc/PE (1:1), R$_f$: 0.65; ESI (m/z, MH$^+$): 471.0

N-((2-(tert-butyl)-4-(3-chlorophenyl)thiazol-5-yl)methyl)-2-(3-fluoro-4-(methylsulfonamidomethyl)phenyl)propanamide (EX-3) from INT-10a-ii and INT-11b.

N-((2-(tert-butyl)-4-(3-tolyl)thiazol-5-yl)methyl)-2-(3-fluoro-4-(methylsulfonamidomethyl)-phenyl)propanamide (EX-4) from INT-10a-iii and INT-11 b. ESI (m/z, MH$^+$): 518.1

N-((2-(tert-butyl)-4-(3-chlorophenyl)thiazol-5-yl)methyl)-2-(3-fluoro-4-(hydroxymethyl)phenyl)propanamide (EX-7) from INT-10a-ii and INT-11d.

N-((2-(tert-butyl)-4-(m-tolyl)thiazol-5-yl)methyl)-2-(3-fluoro-4-(hydroxymethyl)phenyl)propanamide (EX-8) from INT-10a-iii and INT-11d. ESI (m/z, MH$^+$): 441.3

N-((4-(3-chlorophenyl)-2-(trifluoromethyl)oxazol-5-yl)methyl)-2-(4-(3-hydroxyoxetan-3-yl)phenyl)propanamide (EX-9) from INT-10b-i and INT-11e. TLC system: EtOAc/PE (1:1), R$_f$: 0.2; ESI (m/z, MH$^+$): 479.1

N-((4-(3-chlorophenyl)-2-(trifluoromethyl)thiazol-5-yl)methyl)-2-(4-(3-hydroxyoxetan-3-yl)phenyl)propanamide (EX-10) from INT-10b-ii and INT-11e. TLC system: EtOAc/PE (1:1), R$_f$: ESI (m/z, MH$^+$): 497.0

N-((4-(3-chlorophenyl)-2-(trifluoromethyl)oxazol-5-yl)methyl)-2-(5-fluoro-6-(2-(methylsulfonyl)ethyl)pyridin-3-yl)propanamide (EX-11) from INT-10b-i and INT-11f. TLC system: EtOAc, R$_f$: 0.4; ESI (m/z, MH$^+$): 534.1

N-((4-(3-chlorophenyl)-2-(trifluoromethyl)thiazol-5-yl)methyl)-2-(5-fluoro-6-(2-(methylsulfonyl)ethyl)pyridin-3-yl)propanamide (EX-12) from INT-10b-ii and INT-11f. TLC system: EtOAc, R$_f$: 0.4; ESI (m/z, MH$^+$): 550.1

N-((4-(3-chlorophenyl)-2-(trifluoromethyl)oxazol-5-yl)methyl)-2-(5-fluoro-6-(hydroxymethyl)pyridin-3-yl)propanamide (EX-19) from INT-10b-i and INT-11h. TLC system: EtOAc/PE (1:1), R$_f$: 0.25; ESI (m/z, MH$^+$): 458.2

N-((4-(3-chlorophenyl)-2-(trifluoromethyl)thiazol-5-yl)methyl)-2-(5-fluoro-6-(hydroxymethyl)pyridin-3-yl)propanamide (EX-20) from INT-10b-ii and INT-11h. TLC system: EtOAc, R$_f$: 0.2; ESI (m/z, MH$^+$): 474.1

Synthesis of N-((4-(3-chlorophenyl)-2-(trifluoromethyl)oxazol-5-yl)methyl)-2-(4-((sulfamoylamino)methyl)phenyl)propanamide (EX-5)

Synthesis of tert-butyl N-(4-(1-(((4-(3-chlorophenyl)-2-(trifluoromethyl)oxazol-5-yl)methyl)amino)-1-oxopropan-2-yl)benzyl)sulfamoylcarbamate To a stirred solution of 2-(4-(((N-(tert-butoxycarbonyl)sulfamoyl)amino)methyl)phenyl)propanoic acid (INT-11c, 200 mg, 0.550 mmol, 1.0 eq) in DCM (10 mL) under inert atmosphere was added EDC.HCl (126 mg, 0.660 mmol, 1.2 eq) followed by HOBT (89 mg, 0.66 mmol, 1.2 eq), TEA (0.23 mL, 1.7 mmol, 3.0 eq) at RT and stirred for 15 min, then added (4-(3-chlorophenyl)-2-(trifluoromethyl)oxazol-5-yl)methanamine hydrochloride (INT-10b-i, 174 mg, 0.550 mmol, 1.0 eq) and stirred at RT for 12 h. The RM was diluted with water (50 mL) and extracted into DCM (100 mL), dried over Na$_2$SO$_4$ and evaporated under reduced pressure to get tert-butyl N-(4-(1-(((4-(3-chlorophenyl)-2-(trifluoromethyl)oxazol-5-yl)methyl)amino)-1-oxopropan-2-yl)benzyl)sulfamoylcarbamate (300 mg, 87%) as a pale yellow solid. TLC system: EtOAc/PE (1:1), R$_f$: 0.6

Synthesis of N-((4-(3-chlorophenyl)-2-(trifluoromethyl)oxazol-5-yl)methyl)-2-(4-((sulfamoylamino)methyl)phenyl)propanamide (EX-5)

To a stirred solution of tert-butyl N-(4-(1-(((4-(3-chlorophenyl)-2-(trifluoromethyl)oxazol-5-yl)methyl)amino)-1-oxopropan-2-yl)benzyl)sulfamoylcarbamate (300 mg, 0.480 mmol, 1.0 eq) in DCM (10 mL) was slowly added TFA (4.0 mL) at 0° C. and the RM was stirred for 3 h at RT. The RM was diluted with water (30 mL) and basified (pH 8) with sat. NaHCO$_3$ solution and extracted into DCM (50 mL), washed with brine, dried over Na$_2$SO$_4$ and evaporated under reduced pressure to get crude compound. The crude was washed with Et$_2$O to get N-((4-(3-chlorophenyl)-2-(trifluoromethyl)oxazol-5-yl)methyl)-2-(4-((sulfamoylamino)methyl)phenyl)propanamide (EX-5, 125 mg, 49%) as a white solid. TLC system: EtOAc/PE (1:1), R$_f$: 0.4; ESI (m/z; MH$^+$): 515.1

According to the procedure described for EX-5, the following amides were prepared:

N-((4-(3-chlorophenyl)-2-(trifluoromethyl)thiazol-5-yl)methyl)-2-(4-((sulfamoylamino)methyl)phenyl)propanamide (EX-6) from INT-10b-ii and INT-11c. TLC system: EtOAc/PE (1:1), R$_f$: 0.4; ESI (m/z, MH$^+$): 533.1

N-((4-(3-chlorophenyl)-2-(trifluoromethyl)oxazol-5-yl)methyl)-2-(3-fluoro-4-((sulfamoylamino)methyl)phenyl)propanamide (EX-23) from INT-10b-i and INT-11i. TLC system: EtOAc/PE (1:1), R$_f$: 0.25; ESI (m/z, MH$^+$): 535.4

N-((4-(3-chlorophenyl)-2-(trifluoromethyl)thiazol-5-yl)methyl)-2-(3-fluoro-4-((sulfamoylamino)methyl)phenyl)propanamide (EX-24) from INT-10b-ii and INT-11i. TLC system: EtOAc/PE (1:1), R$_f$: 0.05; ESI (m/z, MH$^+$): 551.3

Synthesis of N-((4-(3-chlorophenyl)-2-(trifluoromethyl)oxazol-5-yl)methyl)-2-(6-((2-hydroxyethyl)amino)pyridin-3-yl)propanamide (EX-13)

Synthesis of N-((4-(3-chlorophenyl)-2-(trifluoromethyl)oxazol-5-yl)methyl)-2-(6-((2-methoxyethyl)amino)pyridin-3-yl)propanamide To a stirred solution of 2-(6-((2-methoxyethyl)amino)pyridin-3-yl)propanoic acid (INT-11g, 200 mg, 0.890 mmol, 1.0 eq) in DCM at 0° C. were added EDC.HCl (203 mg, 1.06 mmol, 1.2 eq), HOBt (144 mg, 1.06 mmol, 1.2 eq), TEA (0.38 mL, 2.67 mmol, 3.0 eq) and (4-(3-chlorophenyl)-2-(trifluoromethyl)oxazol-5-yl)methanamine hydrochloride (INT-10b-i, 278 mg, 0.89 mmol, 1.0 eq) and the RM was stirred at RT for 16 h. The RM was diluted with water (10 mL) and extracted with DCM (10 mL), dried ($Na_2SO_4$) and concentrated. The resulting crude was purified by silica gel column chromatography (60-120 mesh) using EtOAc/PE (1:1) as eluent to get N-((4-(3-chlorophenyl)-2-(trifluoromethyl)oxazol-5-yl)methyl)-2-(6-((2-methoxyethyl)amino)pyridin-3-yl)propanamide (200 mg, 46%) as a pale yellow solid. TLC system: EtOAc (100%), $R_f$: 0.5

Synthesis of N-((4-(3-chlorophenyl)-2-(trifluoromethyl)oxazol-5-yl)methyl)-2-(6-((2-hydroxyethyl)amino)pyridin-3-yl)propanamide (EX-13)

To a stirred solution of N-((4-(3-chlorophenyl)-2-(trifluoromethyl)oxazol-5-yl)methyl)-2-(6-((2-methoxyethyl)amino)pyridin-3-yl)propanamide (150 mg, 0.310 mmol, 1.0 eq) in isopropanethiol (5 mL) was added $BF_3.Et_2O$ (5 mL) at RT and the RM was refluxed for 12 h. The RM was quenched with aq. $NaHCO_3$ solution and extracted with DCM (15 mL), dried over $Na_2SO_4$ and evaporated. The crude was purified by preparative TLC using EtOAc as eluent and was further washed with $Et_2O$/pentane (1:9) (2×10 mL) to get N-((4-(3-chlorophenyl)-2-(trifluoromethyl)oxazol-5-yl)methyl)-2-(6-((2-hydroxyethyl)amino)pyridin-3-yl)propanamide (EX-13, 110 mg, 75%) as a colorless solid. TLC system: EtOAc, $R_f$: 0.15; ESI (m/z; $MH^+$): 469.4

According to the procedure described for EX-13, N-((4-(3-chlorophenyl)-2-(trifluoromethyl)thiazol-5-yl)methyl)-2-(6-((2-hydroxyethyl)amino)pyridin-3-yl)propanamide (EX-14) was prepared from INT-10b-ii and INT-11g. TLC system: EtOAc/PE (9:1), $R_f$: 0.2; ESI (m/z, $MH^+$): 485.1

Chiral Separation of Amides

Racemic EX-14 was subjected to chiral preparative SFC. Column: Chiralpak-ASH (250×30 mm); eluent $CO_2$/MeOH 3/1; flow 70 g/min; pressure 100 bar; loading per injection: 35 mg.
First eluting enantiomer (EX-15): ESI (m/z, $MH^+$): 485.2
Second eluting enantiomer: (EX-16): ESI (m/z, $MH^+$): 485.3

Racemic EX-13 was subjected to chiral preparative HPLC. Column: Chiralpak-IB (250×20 mm); eluent hexane/DCM/EtOH/diethylamine 80/10/10/0.1; flow 22 mL/min; loading per injection: 5 mg.
First eluting enantiomer (EX-17): ESI (m/z, $MH^+$): 468.8
Second eluting enantiomer (EX-18): ESI (m/z, $MH^+$): 468.9

Racemic EX-19 was subjected to chiral preparative HPLC. Column: Chiralpak-AY-H (250×30 mm); eluent hexane/isopropanol/EtOH/trifluoroacetic acid 80/20/2/0.1; flow 30 mL/min; loading per injection: 30 mg.
First eluting enantiomer (EX-21): ESI (m/z, $MH^+$): 457.9
Second eluting enantiomer (EX-22): ESI (m/z, $MH^+$): 457.8

Azoleureas can be synthesized from azole methylamines hydrochlorides INT-10 and the carbamates INT-14. These carbamates can be prepared by reacting the amines INT-12 with phenylchloroformiate 13 (Scheme 3)

Scheme 2: Synthesis of ureas.

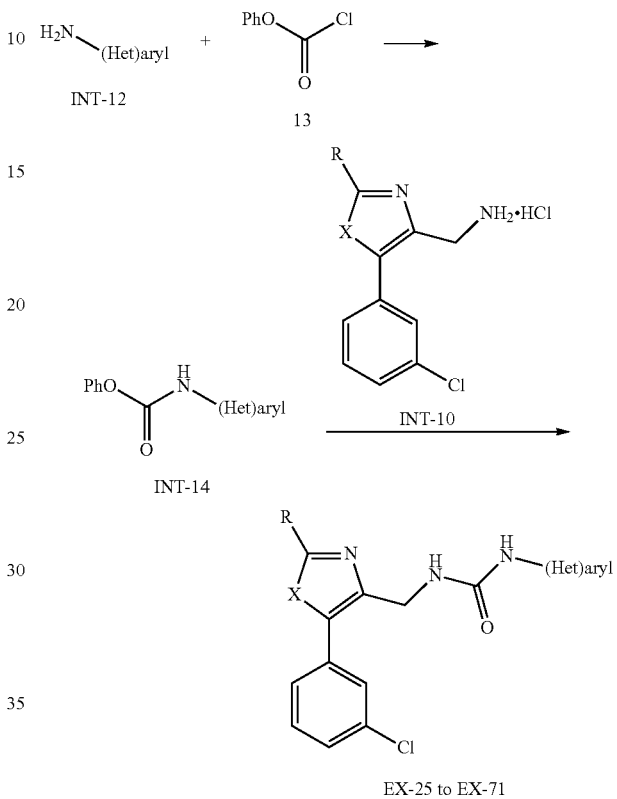

EX-25 to EX-71

Synthesis of phenyl carbamates INT-14

Table 3 summarizes the phenyl cabamates INT-14 which syntheses has already been described in literature.

TABLE 3

| Literature described phenyl carbamates INT-14. | | |
|---|---|---|
| phenyl (6-(((tert-butyldimethylsilyl)oxy)methyl)pyridin-3-yl)carbamate | INT-14a | WO2013013815, pp. 230 |
| phenyl (6-(2-((tert-butyldimethylsilyl)oxy)ethyl)pyridin-3-yl)carbamate | INT-14b | WO2013013815, pp. 141 |
| phenyl (4-(methylsulfonamidomethyl)phenyl)carbamate | INT-14c | WO2013068462, pp. 72 |
| tert-butyl N-(4-(phenyloxycarbonylamino)-benzyl)sulfamoylcarbamate | INT-14e | WO2013068462, pp. 78 |
| phenyl (3-fluoro-4-(methylsulfonamidomethyl)phenyl)carbamate | INT-14n | WO2013068462, pp. 76 |
| phenyl (3-fluoro-4-(hydroxymethyl)phenyl)carbamate | INT-14o | WO2013068467, pp. 65 |

Synthesis of phenyl (6-((2-methoxyethoxy)methyl)
pyridin-3-yl)carbamate (INT-14f)

Synthesis of 5-bromopicolinaldehyde

To a stirred solution of 5-bromopicolinonitrile (5.00 g, 27.3 mmol, 1 eq) in THF (50 mL) was added 1M DIBAL (41 mL, 40.98 mmol, 1 eq) slowly dropwise at −78° C. and the RM was stirred for 6 h at same temperature. The RM was quenched with 1N HCl at −78° C. and neutralized with saturated NaHCO$_3$ solution, extracted with EtOAc, dried (Na$_2$SO$_4$), and concentrated to get 5-bromopicolinaldehyde (3.00 g, 59%), which was used without further purification. TLC system: EtOAc/PE (2:3), R$_f$: 0.5

Synthesis of (5-bromopyridin-2-yl)methanol

To a stirred solution of 5-bromopicolinaldehyde (3.0 g, 16 mmol, 1.0 eq) in MeOH (30 mL) at 0° C. was added NaBH$_4$ (1.16 g, 32.0 mmol, 2.0 eq) and the RM was stirred for 1 h at 0° C., warmed to RT and stirred for 1 h. The RM was concentrated, diluted with water and extracted with EtOAc, dried (Na$_2$SO$_4$) and evaporated to get (5-bromopyridin-2-yl)methanol (1.5 g, ~49%), which was used without further purification. TLC system: EtOAc/PE (2:3), R$_f$: 0.55

Synthesis of
5-bromo-2-((2-methoxyethoxy)methyl)pyridine

To a stirred solution of (5-bromopyridin-2-yl)methanol (0.100 g, 0.531 mmol, 1.0 eq) in THF (10 mL) was added NaH (38 mg, 1.5 mmol, 3.0 eq) at 0° C. and stirred for 10 min, then 1-bromo-2-methoxyethane (0.1 mL, 1.0 mmol, 2.0 eq) was added and the RM was stirred at RT for 16 h. The RM was quenched with ice cold water, extracted with EtOAc, dried (Na$_2$SO$_4$) and evaporated to get 5-bromo-2-((2-methoxyethoxy)methyl)pyridine (0.1 g, crude). TLC system: EtOAc/PE (1:9), R$_f$: 0.5

Synthesis of N-(diphenylmethylene)-6-((2-methoxyethoxy)methyl)pyridin-3-amine

To a stirred solution of 5-bromo-2-((2-methoxyethoxy) methyl)pyridine (0.15 g, 0.61 mmol, 1.0 eq) in toluene (5 mL) were added benzophenoneimine (0.12 mL, 0.73 mmol, 1.2 eq), Pd$_2$dba$_3$ (56 mg, 0.061 mmol, 0.1 eq) Cs$_2$CO$_3$ (0.3 g, 0.92 mmol, 1.5 eq), under N$_2$. The RM was refluxed for 16 h, diluted with water (5 mL) and extracted with EtOAc (10 mL), dried over Na$_2$SO$_4$ and evaporated to get N-(diphenylmethylene)-6-((2-methoxyethoxy)methyl)pyridin-3-amine (200 mg, crude). The crude was used directly for next step without further purification.

Synthesis of
6-((2-methoxyethoxy)methyl)pyridin-3-amine

To a solution of N-(diphenylmethylene)-6-((2-methoxyethoxy)methyl)pyridin-3-amine (200 mg) in MeOH was added conc HCl (2 mL) and the RM was stirred at RT for 30 min. The RM was diluted with water (5 mL), neutralized with TEA and extracted with EtOAc (10 mL) and evaporated under reduced pressure. The crude obtained was washed with Et$_2$O (10 mL) to get 6-((2-methoxyethoxy)methyl) pyridin-3-amine (100 mg), which was used without further purification. TLC system: MeOH/DCM (1:19), R$_f$: 0.2

Synthesis of phenyl (6-((2-methoxyethoxy)methyl)
pyridin-3-yl)carbamate (INT-14f)

To a stirred solution of 6-((2-methoxyethoxy)methyl) pyridin-3-amine (450 mg, 2.48 mmol, 1.0 eq) in acetone (5 mL) were added phenyl chloroformiate (13, 0.313 mL, 2.48 mmol, 1.0 eq), and pyridine (0.6 mL, 7.5 mmol, 3.0 eq) at 0° C. The RM was stirred at same temperature for 2 h. The RM was concentrated under reduced pressure, the residue was diluted with DCM (20 mL and washed with water (8 mL). The aqueous phase was extracted with DCM, the combined organic phases were dried over Na$_2$SO$_4$ and concentrated under reduced pressure. The crude was purified by silica gel (100-200 mesh) column chromatography using EtOAc/PE (4:1) as eluent to get to get phenyl (6-((2-methoxyethoxy)methyl)pyridin-3-yl)carbamate (INT-14f, 400 mg, 53%) as a colorless solid. TLC system MeOH/DCM (1:19), R$_f$: 0.4

Synthesis of phenyl (6-(2-((tert-butyldimethylsilyl)
oxy)ethoxy)pyridin-3-yl)carbamate (INT-14d)

Synthesis of 2-((5-nitropyridin-2-yl)oxy)ethanol

To a stirred solution of 60% NaH in mineral oil (302 mg, 12.6 mmol, 2.0 eq) in THF (10 mL) was added ethylene glycol (783 mg, 12.6 mmol, 2.0 eq.) at 0° C. and stirred for 15 min. 2-chloro-5-nitropyridine (1.00 g, 6.31 mmol, 1.0 eq.) in DMF (3 mL) was added, the RM was allowed to warm to RT and heated to 50° C. for 3 h. The RM was cooled and quenched with ice cold water (10 mL), extracted with EtOAc (2×15 mL), washed with brine, dried over anhydrous Na$_2$SO$_4$, evaporated and dried under vacuum to get crude. The crude was purified by silica gel column chromatography (100-200 mesh) using EtOAc/PE (1:4) as eluent to get 2-((5-nitropyridin-2-yl)oxy)ethanol (900 mg, 77%) as a colourless liquid. TLC system: EtOAc/PE (7:3), R$_f$: 0.5

Synthesis of 2-(2-((tert-butyldimethylsilyl)oxy)
ethoxy)-5-nitropyridine

To a stirred solution of 2-((5-nitropyridin-2-yl)oxy)ethanol (900 mg, 4.89 mmol, 1.0 eq.) in DCM (10 mL) was added imidazole (665 mg, 9.78 mmol, 2 eq.), the RM was cooled to 0° C. and TBDMSCl (820 mg, 5.40 mmol, 1.1 eq.) was added. The RM was stirred for 2 h at RT, diluted with water (20 mL), extracted with DCM (2×25 mL), washed with brine (10 mL), dried over anhydrous Na$_2$SO$_4$ and evaporated to get 2-(2-((tert-butyldimethylsilyl)oxy) ethoxy)-5-nitropyridine (1.26 g, 87%) which was used without further purification. TLC system: EtOAc/PE (1:1), R$_f$: 0.5.

Synthesis of 6-(2-((tert-butyldimethylsilyl)oxy)
ethoxy)pyridin-3-amine

To a stirred solution of 2-(2-((tert-butyldimethylsilyl)oxy) ethoxy)-5-nitropyridine (1.25 g, 4.36 mmol, 1.0 eq.) in MeOH (20 mL) was added 10% Pd/C (200 mg) and the mixture was hydrogenated using H$_2$ balloon at RT for 2 h. The RM was filtered through celite bed and concentrated under reduced pressure to get crude. The crude was purified by preparative HPLC to get 6-(2-((tert-butyldimethylsilyl) oxy)ethoxy)-pyridin-3-amine (820 mg, 72%) as a brown solid. TLC system: EtOAC/PE (9:1), R$_f$: 0.2

Synthesis of phenyl (6-(2-((tert-butyldimethylsilyl)oxy)ethoxy)pyridin-3-yl)carbamate (INT-14d)

To a stirred solution of 6-(2-((tert-butyldimethylsilyl)oxy)ethoxy)pyridin-3-amine (150 mg, 0.600 mmol, 1.0 eq.) in acetone (5 mL) were added PhOCOCl (0.078 mL, 0.67 mmol, 1.1 eq.) and pyridine (0.14 mL, 1.8 mmol, 3 eq.) at 0° C. The RM was stirred at same temperature for 1 h. The solvent was evaporated and the residue was diluted with DCM (10 mL), washed with water (10 mL), dried over $Na_2SO_4$ and concentrated under reduced pressure. The crude was washed with $Et_2O$ (5 mL) to get phenyl (6-(2-((tert-butyldimethylsilyl)oxy)ethoxy)pyridin-3-yl)carbamate (INT-14d, 125 mg, 56%) as a white solid. TLC system: EtOAC/PE (3:7), $R_f$: 0.6.

Synthesis of phenyl (6-(3-((tert-butyldimethylsilyl)oxy)azetidin-1-yl)pyridin-3-yl)carbamate (INT-14ac)

Synthesis of 1-(5-nitropyridin-2-yl)azetidin-3-ol

A mixture of 2-chloro-5-nitropyridine (1.00 g, 6.32 mmol), azetidin-3-ol hydrochloride (1.04 g, 9.50 mmol) and TEA (1.3 mL, 9.5 mmol) in DMF (33 mL) was heated at 100° C. for 20 h. The RM was cooled to RT, diluted with water (30 mL), extracted with EtOAc (2×30 mL), washed with water (30 mL) and brine (20 mL), dried over $Na_2SO_4$ and evaporated the solvent to get 1-(5-nitropyridin-2-yl)azetidin-3-ol (0.52 g, 42%) which was used without further purification. TLC system: EtOAc/PE (1:9), $R_f$: 0.2

Synthesis of 2-(3-((tert-butyldimethylsilyl)oxy)azetidin-1-yl)-5-nitropyridine To a stirred solution of 1-(5-nitropyridin-2-yl)azetidin-3-ol (0.52 g, 2.7 mmol) in DCM (10 mL) at 0° C. was added imidazole (0.32 g, 5.3 mmol) followed by TBDMSCl (0.80 g, 5.3 mmol) and stirred at RT for 16 h. The RM was diluted with water (10 mL), extracted with DCM (2×20 mL), washed with brine (10 mL), dried over $Na_2SO_4$ and evaporated to get crude compound. The crude was purified by silica gel column chromatography (100-200 mesh) using 6% EtOAc/PE as eluent to get 2-(3-((tert-butyldimethylsilyl)oxy)azetidin-1-yl)-5-nitropyridine (0.60 g, 75%). TLC system: EtOAc/PE (3:7), $R_f$: 0.6

Synthesis of 6-(3-((tert-butyldimethylsilyl)oxy)azetidin-1-yl)pyridin-3-amine A solution of 2-(3-((tert-butyldimethylsilyl)oxy)azetidin-1-yl)-5-nitropyridine (0.60 g, 1.94 mmol), 10% Pd/C (300 mg) in EtOH (20 mL) was hydrogenated under hydrogen balloon at RT for 14 h. The RM was filtered through a celite pad, washed with EtOH and the solvent was evaporated under reduced pressure to get 6-(3-((tert-butyldimethylsilyl)oxy)azetidin-1-yl)pyridin-3-amine (0.41 g, 76%). TLC system: EtOAc/PE (3:7), $R_f$: 0.6

Synthesis of phenyl (6-(3-((tert-butyldimethylsilyl)oxy)azetidin-1-yl)pyridin-3-yl)carbamate (INT-14ac)

To a stirred solution 6-(3-((tert-butyldimethylsilyl)oxy)azetidin-1-yl)pyridin-3-amine (0.40 g, 1.4 mmol) in acetone (10 mL) at 0° C. was added pyridine (0.17 mL, 2.1 mmol) followed by phenyl chloroformiate (0.22 mL, 1.7 mmol) and the RM was stirred for 2 h. The RM was evaporated under reduced pressure and the crude residue was diluted with water (10 mL), extracted with EtOAc (2×20 mL), washed with brine (10 mL), dried over $Na_2SO_4$ and evaporated to get phenyl (6-(3-((tert-butyldimethylsilyl)oxy)-azetidin-1-yl)pyridin-3-yl)carbamate (INT-14ac, 0.30 g, 52%). TLC system: EtOAc/PE (3:7), $R_f$: 0.7

Table 4 summarizes the phenyl carbamates INT-14 which were obtained from commercially available amines INT-12 and phenyl chloroformiate (13) as described for INT-14f.

TABLE 4

| phenyl carbamates from commercially available amines | |
|---|---|
| phenyl benzo[d][1,3]dioxol-5-ylcarbamate | INT-14g |
| phenyl (2,3-dihydro-1H-inden-4-yl)carbamate | INT-14h |
| phenyl isoquinolin-6-ylcarbamate | INT-14i |
| phenyl quinolin-5-ylcarbamate | INT-14j |
| phenyl (2,3-dihydrobenzo[b][1,4]dioxin-6-yl)carbamate | INT-14k |
| phenyl (2,3-dihydro-1H-inden-5-yl)carbamate | INT-14l |
| phenyl isoquinolin-5-ylcarbamate | INT-14m |
| phenyl (3-methoxypyridin-4-yl)carbamate | INT-14p |
| phenyl pyrimidin-5-ylcarbamate | INT-14q |
| phenyl (5-methylpyridin-2-yl)carbamate | INT-14r |
| phenyl pyridin-4-ylcarbamate | INT-14s |
| phenyl pyridin-2-ylcarbamate | INT-14t |
| phenyl pyridin-3-ylcarbamate | INT-14u |
| phenyl (3-methylpyridin-4-yl)carbamate | INT-14v |
| phenyl (2-methylpyridin-4-yl)carbamate | INT-14w |
| phenyl (6-fluoropyridin-3-yl)carbamate | INT-14x |
| phenyl (6-methylpyridin-3-yl)carbamate | INT-14y |
| phenyl (2-methylpyrimidin-5-yl)carbamate | INT-14z |
| phenyl (2-methoxypyrimidin-5-yl)carbamate | INT-14aa |

Phenyl (6-(2-(methylsulfonyl)ethyl)pyridin-3-yl)carbamate (INT-14ab) was synthesized from 6-(2-(methylsulfonyl)ethyl)pyridin-3-amine (synthesis: see WO20130131815, pp. 129) and phenyl chloroformiate (13) as described for INT-14f.

Synthesis of Azole Ureas

Synthesis of 1-((2-(tert-butyl)-4-(3-chlorophenyl)oxazol-5-yl)methyl)-3-(6-(hydroxymethyl)pyridin-3-yl)urea (EX-25)

Synthesis of 1-((2-(tert-butyl)-4-(3-chlorophenyl)oxazol-5-yl)methyl)-3-(6-(((tert-butyldimethylsilyl)oxy)methyl)pyridin-3-yl)urea To a stirred solution of (2-(tert-butyl)-4-(3-chlorophenyl)oxazol-5-yl)methanamine hydrochloride (INT-10a-i, 200 mg, 0.600 mmol, 1.0 eq) in DCM (5 mL) were added TEA (192 mg, 1.800 mmol, 3 eq) and phenyl (6-(((tert-butyldimethylsilyl)oxy)methyl)pyridin-3-yl)carbamate (INT-14a, 245 mg, 0.600 mmol, 1.0 eq) at 0° C. and the mixture was stirred at RT for 16 h. The RM was diluted with DCM, washed with water and extracted with DCM. Organic layer was dried over $Na_2SO_4$, concentrated under reduced pressure to get 1-((2-(tert-butyl)-4-(3-chlorophenyl)oxazol-5-yl)methyl)-3-(6-(((tert-butyldimethylsilyl)oxy)methyl)pyridin-3-yl)urea (300 mg, 85%) as a brown liquid. TLC system: EtOAc/PE (1:1), $R_f$: 0.4

Synthesis of 1-((2-(tert-butyl)-4-(3-chlorophenyl)oxazol-5-yl)methyl)-3-(6-(hydroxymethyl)pyridin-3-yl)urea (EX-25)

To a stirred solution of 1-((2-(tert-butyl)-4-(3-chlorophenyl)oxazol-5-yl)methyl)-3-(6-(((tert-butyldimethylsilyl)

oxy)methyl)pyridin-3-yl)urea (300 mg, 0.568 mmol, 1.0 eq) in THF (20 mL) was added 2N HCl (10 mL) at 0° C. and the RM was stirred at RT for 4 h. Then the RM was concentrated, diluted with EtOAc (20 mL) and washed with water (20 mL), dried over $Na_2SO_4$ and concentrated under reduced pressure. The crude was purified by silica gel column chromatography (100-200 mesh) using MeOH/DCM (1:9) as eluent to get 1-((2-(tert-butyl)-4-(3-chlorophenyl)oxazol-5-yl)methyl)-3-(6-(hydroxymethyl)pyridin-3-yl)urea (EX-25, 110 mg, 46%) as pale yellow solid. TLC system: MeOH/DCM (1:9), $R_f$: 0.2; ESI (m/z, MH$^+$): 415.0

According to the procedure described for EX-25, the following ureas were prepared:

1-((2-(tert-butyl)-4-(3-chlorophenyl)thiazol-5-yl)methyl)-3-(6-(hydroxymethyl)pyridin-3-yl)urea (EX-26) from INT-10a-ii and INT-14a. TLC system: MeOH/DCM (1:9), $R_f$: 0.2; ESI (m/z, MH$^+$): 431.0

1-((4-(3-chlorophenyl)-2-(trifluoromethyl)oxazol-5-yl)methyl)-3-(6-(hydroxymethyl)pyridin-3-yl)urea (EX-27) from INT-10b-i and INT-14a. TLC system: MeOH/DCM (1:9), $R_f$: 0.2; ESI (m/z, MH$^+$): 427.3

1-((4-(3-chlorophenyl)-2-(trifluoromethyl)thiazol-5-yl)methyl)-3-(6-(hydroxymethyl)pyridin-3-yl)urea (EX-28) from INT-10b-ii and INT-14a. TLC system: MeOH/DCM (1:9), $R_f$: 0.2; ESI (m/z, MH$^+$): 443.3

1-((4-(3-chlorophenyl)-2-(trifluoromethyl)oxazol-5-yl)methyl)-3-(6-(3-hydroxyazetidin-1-yl)pyridin-3-yl)urea (EX-32) from INT-10b-i and INT-14ac. TLC system: MeOH/DCM (1:9), $R_f$: 0.2; ESI (m/z, MH$^+$): 451.2

1-((4-(3-chlorophenyl)-2-(trifluoromethyl)thiazol-5-yl)methyl)-3-(6-(3-hydroxyazetidin-1-yl)pyridin-3-yl)urea (EX-33) from INT-10b-ii and INT-14ac. TLC system: MeOH/DCM (1:9), $R_f$: 0.1; ESI (m/z, MH$^+$): 484.2

1-((4-(3-chlorophenyl)-2-(trifluoromethyl)thiazol-5-yl)methyl)-3-(6-(2-hydroxyethyl)pyridin-3-yl)urea (EX-34) from INT-10b-ii and INT-14b. TLC system: EtOAc, $R_f$: 0.2; ESI (m/z, MH$^+$): 457.3

1-((2-(tert-butyl)-4-(3-chlorophenyl)oxazol-5-yl)methyl)-3-(6-(2-hydroxyethyl)pyridin-3-yl)urea (EX-35) from INT-10a-i and INT-14b. TLC system: MeOH/DCM (1:9), $R_f$: 0.2; ESI (m/z, MH$^+$): 429.0

1-((2-(tert-butyl)-4-(3-chlorophenyl)thiazol-5-yl)methyl)-3-(6-(2-hydroxyethyl)pyridin-3-yl)urea (EX-36) from INT-10a-ii and INT-14b. TLC system: MeOH/DCM (1:9), $R_f$: 0.2; ESI (m/z, MH$^+$): 445.0

1-((4-(3-chlorophenyl)-2-(trifluoromethyl)oxazol-5-yl)methyl)-3-(6-(2-hydroxyethyl)pyridin-3-yl)urea (EX-37) from INT-10b-i and INT-14b. TLC system: EtOAc, $R_f$: 0.2; ESI (m/z, MH$^+$): 441.3

1-((2-(tert-butyl)-4-(3-chlorophenyl)oxazol-5-yl)methyl)-3-(6-(2-hydroxyethoxy)pyridin-3-yl)urea (EX-40) from INT-10a-i and INT-14d. TLC system: EtOAc/PE (1:1), $R_f$: 0.4; ESI (m/z, MH$^+$): 445.0

1-((2-(tert-butyl)-4-(3-chlorophenyl)thiazol-5-yl)methyl)-3-(6-(2-hydroxyethoxy)pyridin-3-yl)urea (EX-41) from INT-10a-ii and INT-14d. TLC system: EtOAc/PE (1:1), $R_f$: 0.4; ESI (m/z, MH$^+$): 460.8

1-((4-(3-chlorophenyl)-2-(trifluoromethyl)oxazol-5-yl)methyl)-3-(6-(2-hydroxyethoxy)pyridin-3-yl)urea (EX-42) from INT-10b-i and INT-14d. TLC system: EtOAc/PE (1:1), $R_f$: 0.a; ESI (m/z, MH$^+$): 457.3

1-((4-(3-chlorophenyl)-2-(trifluoromethyl)thiazol-5-yl)methyl)-3-(6-(2-hydroxyethoxy)pyridin-3-yl)urea (EX-43) from INT-10b-ii and INT-14d. TLC system: MeOH/DCM (1:9), $R_f$: 0.2; ESI (m/z, MH$^+$): 473.1

Synthesis of N-((5-(3-chlorophenyl)-2-(tertbutyl)oxazol-4-yl)methyl)-N'-(4-((sulfamoyl-amino)methyl)phenyl)urea (EX-44)

Synthesis of tert-butyl N-(4-(3-((2-(tert-butyl)-4-(3-chlorophenyl)oxazol-5-yl)methyl)ureido)benzyl)sulfamoylcarbamate To a stirred solution of (2-(tert-butyl)-4-(3-chlorophenyl)oxazol-5-yl)methanamine hydrochloride (INT-10a-i, 160 mg, 0.530 mmol, 1.0 eq) in DCM (20 mL) was added TEA (0.38 mL, 2.7 mmol, 5.0 eq) and stirred at RT for 10 min. Then tert-butyl N-(4-(phenyloxycarbonylamino)-benzyl)sulfamoylcarbamate (INT-14e, 224 mg, 0.53 mmol, 1.0 eq) was added and the mixture was stirred at RT for 16 h. The RM was diluted with DCM (10 mL) and washed with water, dried and evaporated to get crude tert-butyl N-(4-(3-((2-(tert-butyl)-4-(3-chlorophenyl)oxazol-5-yl)methyl)ureido)benzyl)-sulfamoylcarbamate (300 mg) as thick brown liquid which was used without further purification. TLC system: EtOAc/PE (1:1), $R_f$: 0.4.

Synthesis of N-((5-(3-chlorophenyl)-2-(tertbutyl)oxazol-5-yl)methyl)-N'-(4-((sulfamoylamino)methyl)phenyl)urea (EX-44)

To a stirred solution of N-(4-(3-((2-(tert-butyl)-4-(3-chlorophenyl)oxazol-5-yl)methyl)ureido)benzyl)sulfamoylcarbamate (0.30 g, 0.50 mmol, 1.0 eq) in DCM (10 mL) was added TFA (2 mL) at 0° C., stirred for 30 min and then at RT for another 2 h. The RM was slowly quenched with saturated NaHCO$_3$ solution (pH 8) and extracted with DCM (20 mL), dried (Na$_2$SO$_4$) and evaporated under reduced pressure. This crude was purified by preparative TLC to get N-((5-(3-chlorophenyl)-2-(tert-butyl)oxazol-5-yl)methyl)-N'-(4-((sulfamoylamino)methyl)phenyl)urea (EX-44, 75 mg, 28% over 2 steps) as off-white solid. TLC system: EtOAc, $R_f$: 0.25; ESI (m/z MH$^+$): 491.8

According to the procedure described for EX-44, N-((5-(3-chlorophenyl)-2-(tertbutyl)thiazol-5-yl)methyl)-N'-(4-((sulfamoylamino)methyl)phenyl)urea (EX-45) from INT-10aii and INT-14e. TLC system: EtOAc/PE (1:1), $R_f$: 0.15; ESI (m/z, MH$^+$): 507.8

Synthesis of 1-((2-(tert-butyl)-4-(3-chlorophenyl)oxazol-5-yl)methyl)-3-(6-((2-hydroxyethoxy)methyl)pyridin-3-yl)urea dihydrochloride (EX-46)

Synthesis of 1-((2-(tert-butyl)-4-(3-chlorophenyl)oxazol-5-yl)methyl)-3-(6-((2-methoxyethoxy)methyl)pyridin-3-yl)urea To a stirred solution of (2-(tert-butyl)-4-(3-chlorophenyl)oxazol-5-yl)methanamine hydrochloride (INT-10a-i, 150 mg, 0.500 mmol, 1.0 eq) in DCM (5 mL) were added TEA (151 mg, 1.50 mmol, 3 eq) and phenyl (6-((2-methoxyethoxy)methyl)pyridin-3-yl)carbamate (INT-14f, 151 mg, 0.500 mmol, 1.0 eq) at 0° C. and stirred at RT for 12 h. Then the RM was diluted with DCM (10 mL), washed with water (20 mL) and dried over Na$_2$SO$_4$ and concentrated under reduced pressure to get 1-((2-(tert-butyl)-4-(3-chlorophenyl)oxazol-5-yl)methyl)-3-(6-((2-methoxyethoxy)methyl)pyridin-3-yl)urea (200 mg, 85%) as a yellow liquid which was used without further purification. TLC system: EtOAc/PE (7:3), $R_f$: 0.5

Synthesis of 1-((2-(tert-butyl)-4-(3-chlorophenyl) oxazol-5-yl)methyl)-3-(6-((2-hydroxyethoxy) methyl)pyridin-3-yl)urea dihydrochloride (EX-46)

To a stirred solution of get 1-((2-(tert-butyl)-4-(3-chlorophenyl)oxazol-5-yl)methyl)-3-(6-((2-methoxyethoxy) methyl)pyridin-3-yl)urea (200 mg, 0.423 mmol, 1.0 eq) in DCM (20 mL) was added 1 M BBr$_3$ solution in DCM (0.85 mL, 0.87 mmol, 2.0 eq), at −78° C. and stirred at RT for 2 h. The RM was quenched with saturated NaHCO$_3$ solution (10 mL), diluted with DCM (10 mL), washed with water (20 mL), dried over Na$_2$SO$_4$ and concentrated under reduced pressure. The crude was purified by preperative HPLC, dissolved in Et$_2$O (5 mL) and precipitated with HCl in Et$_2$O to get 1-((2-(tert-butyl)-4-(3-chlorophenyl)oxazol-5-yl) methyl)-3-(6-((2-hydroxyethoxy)methyl)pyridin-3-yl)urea dihydrochloride (EX-46, 60 mg, 30%) as off white solid. TLC system: EtOAC/PE (9:1), R$_f$: 0.4; ESI (m/z MH$^+$): 459.2

According to the procedure described for EX-46, the following ureas were prepared:

1-((2-(tert-butyl)-4-(3-chlorophenyl)thiazol-5-yl)methyl)-3-(6-((2-hydroxyethoxy)methyl)pyridin-3-yl)urea dihydrochloride (EX-47) from INT-10a-ii and INT-14f. TLC system: EtOAc/PE (9:1), R$_f$: 0.4; ESI (m/z, MH$^+$): 475.4

1-((4-(3-chlorophenyl)-2-(trifluoromethyl)oxazol-5-yl) methyl)-3-(6-((2-hydroxyethoxy)methyl)pyridin-3-yl) urea dihydrochloride (EX-48) from INT-10b-i and INT-14f. TLC system: EtOAc/PE (9:1), R$_f$: 0.4; ESI (m/z, MH$^+$): 471.1

1-((4-(3-chlorophenyl)-2-(trifluoromethyl)thiazol-5-yl) methyl)-3-(6-((2-hydroxyethoxy)methyl)pyridin-3-yl) urea dihydrochloride (EX-49) from INT-10b-ii and INT-14f. TLC system: EtOAc/PE (9:1), R$_f$: 0.2; ESI (m/z, MH$^+$): 487.2

Synthesis of 1-((4-(3-chlorophenyl)-2-(trifluoromethyl)oxazol-5-yl)methyl)-3-(6-(2-(methylsulfonyl) ethyl)pyridin-3-yl)urea (EX-30)

To a stirred solution of (4-(3-chlorophenyl)-2-(trifluoromethyl)oxazol-5-yl)methanamine hydrochloride (INT-10b-i, 0.15 g, 0.48 mmol) in DCM (10 mL) at 0° C. was added TEA (0.21 mL, 1.44 mmol) followed by phenyl (6-(2-(methylsulfonyl)ethyl)pyridin-3-yl)carbamate (INT-14ab, 0.15 g, 0.48 mmol) and stirred at rt for 16 h. The RM was diluted with water (10 mL), extracted with DCM (2×20 mL), washed with brine (10 mL), dried over anhydrous Na$_2$SO$_4$ and evaporated the solvent to get the crude compound. The crude was purified by silica gel column chromatography (60-120 mesh) using 5% MeOH in DCM as eluent to get 1-((4-(3-chlorophenyl)-2-(trifluoromethyl)oxazol-5-yl) methyl)-3-(6-(2-(methylsulfonyl)ethyl)pyridin-3-yl)urea (EX-30, 0.16 g, 66%). TLC system: EtOAc, R$_f$: 0.2, ESI (m/z MH$^+$): 503.3

According to the procedure described for EX-30, the following ureas were prepared:

1-((2-(tert-butyl)-4-(3-chlorophenyl)thiazol-5-yl)methyl)-3-(2-methoxypyrimidin-5-yl)urea (EX-29) from INT-10a-ii and INT-14a. ESI (m/z, MH$^+$): 432.2

1-((4-(3-chlorophenyl)-2-(trifluoromethyl)thiazol-5-yl) methyl)-3-(6-(2-(methylsulfonyl)ethyl)pyridin-3-yl)urea (EX-31) from INT-10b-ii and INT-14ab. TLC system: EtOAc/hexane (7:3), R$_f$: 0.2; ESI (m/z, MH$^+$): 518.9

N-(4-(3-((2-(tert-butyl)-4-(3-chlorophenyl)oxazol-5-yl) methyl)ureido)benzyl)methanesulfonamide (EX-38) from INT-10a-i and INT-14c. TLC system: MeOH/DCM (1:9), R$_f$: 0.4; ESI (m/z, MH$^+$): 491.0

N-(4-(3-((2-(tert-butyl)-4-(3-fluorophenyl)thiazol-5-yl) methyl)ureido)benzyl)methanesulfonamide (EX-39) from INT-10a-iv and INT-14c. TLC system: EtOAc/PE (7:3), R$_f$: 0.4; ESI (m/z, MH$^+$): 507.0

1-(benzo[d][1,3]dioxol-5-yl)-3-((2-(tert-butyl)-4-(3-chlorophenyl)thiazol-5-yl)methyl)urea (EX-50) from INT-10a-ii and INT-14g.

1-((2-(tert-butyl)-4-(3-chlorophenyl)thiazol-5-yl)methyl)-3-(2,3-dihydro-1H-inden-4-yl)urea (EX-51) from INT-10a-ii and INT-14h.

1-((2-(tert-butyl)-4-(3-chlorophenyl)thiazol-5-yl)methyl)-3-(isoquinolin-6-yl)urea (EX-52) from INT-10a-ii and INT-14i.

1-((2-(tert-butyl)-4-(3-chlorophenyl)thiazol-5-yl)methyl)-3-(quinolin-5-yl)urea (EX-53) from INT-10a-ii and INT-14j.

1-((2-(tert-butyl)-4-(3-chlorophenyl)thiazol-5-yl)methyl)-3-(2,3-dihydrobenzo[b][1,4]dioxin-6-yl)urea (EX-54) from INT-10a-ii and INT-14k.

1-((2-(tert-butyl)-4-(3-chlorophenyl)thiazol-5-yl)methyl)-3-(2,3-dihydro-1H-inden-5-yl)urea (EX-55) from INT-10a-ii and INT-14I. ESI (m/z, MH$^+$): 440.2

1-((2-(tert-butyl)-4-(3-chlorophenyl)thiazol-5-yl)methyl)-3-(isoquinolin-5-yl)urea (EX-56) from INT-10a-ii and INT-14m. ESI (m/z, MH$^+$): 451.2

N-(4-(3-((2-(tert-butyl)-4-(3-chlorophenyl)thiazol-5-yl) methyl)ureido)-2-fluorobenzyl)methanesulfonamide (EX-57) from INT-10a-ii and INT-14n.

N-(4-(3-((2-(tert-butyl)-4-(m-tolyl)thiazol-5-yl)methyl) ureido)-2-fluorobenzyl)methanesulfonamide (EX-58) from INT-10a-iii and INT-14n.

1-((2-(tert-butyl)-4-(3-chlorophenyl)thiazol-5-yl)methyl)-3-(3-fluoro-4-(hydroxymethyl)phenyl)urea (EX-59) from INT-10a-ii and INT-14o. ESI (m/z, MH$^+$): 448.1

1-((2-(tert-butyl)-4-(m-tolyl)thiazol-5-yl)methyl)-3-(3-fluoro-4-(hydroxymethyl)phenyl)urea (EX-60) from INT-10a-iii and INT-14o.

1-((2-(tert-butyl)-4-(3-chlorophenyl)thiazol-5-yl)methyl)-3-(3-methoxypyridin-4-yl)urea (EX-61) from INT-10a-ii and INT-14p. ESI (m/z, MH$^+$): 431.2

1-((2-(tert-butyl)-4-(3-chlorophenyl)thiazol-5-yl)methyl)-3-(pyrimidin-5-yl)urea (EX-62) from INT-10a-ii and INT-14q. ESI (m/z, MH$^+$): 402.1

1-((2-(tert-butyl)-4-(3-chlorophenyl)thiazol-5-yl)methyl)-3-(5-methylpyridin-2-yl)urea (EX-63) from INT-10a-ii and INT-14r. ESI (m/z, MH$^+$): 415.2

1-((2-(tert-butyl)-4-(3-chlorophenyl)thiazol-5-yl)methyl)-3-(pyridin-4-yl)urea (EX-64) from INT-10a-ii and INT-14s. ESI (m/z, MH$^+$): 401.1

1-((2-(tert-butyl)-4-(3-chlorophenyl)thiazol-5-yl)methyl)-3-(pyridin-2-yl)urea (EX-65) from INT-10a-ii and INT-14t. ESI (m/z, MH$^+$): 401.1

1-((2-(tert-butyl)-4-(3-chlorophenyl)thiazol-5-yl)methyl)-3-(pyridin-3-yl)urea (EX-66) from INT-10a-ii and INT-14u. ESI (m/z, MH$^+$): 401.1

1-((2-(tert-butyl)-4-(3-chlorophenyl)thiazol-5-yl)methyl)-3-(3-methylpyridin-4-yl)urea (EX-67) from INT-10a-ii and INT-14v. ESI (m/z, MH+): 415.1

1-((2-(tert-butyl)-4-(3-chlorophenyl)thiazol-5-yl)methyl)-3-(2-methylpyridin-4-yl)urea (EX-68) from INT-10a-ii and INT-14w. ESI (m/z, MH+): 415.1

1-((2-(tert-butyl)-4-(3-chlorophenyl)thiazol-5-yl)methyl)-3-(6-fluoropyridin-3-yl)urea (EX-69) from INT-10a-ii and INT-14x. ESI (m/z, MH+): 419.1

1-((2-(tert-butyl)-4-(3-chlorophenyl)thiazol-5-yl)methyl)-3-(6-methylpyridin-3-yl)urea (EX-70) from INT-10a-ii and INT-14y. ESI (m/z, MH+): 415.1

1-((2-(tert-butyl)-4-(3-chlorophenyl)thiazol-5-yl)methyl)-3-(2-methylpyrimidin-5-yl)urea (EX-71) from INT-10a-ii and INT-14z. ESI (m/z, MH+): 416.2

Pharmacological Methods

FLIPR Assay:

The FLIPR protocol consists of 2 substance additions during a kinetic measurement. First the compounds to be tested (5 µM) are pipetted onto the cells and the $Ca^{2+}$ influx is determined in comparison to the control (capsaicin 10 µM), providing the result as % activation and representing the compound-alone effect (calculation at peak signal related to baseline). A $Ca^{2+}$ influx of 10%-60% reveals a partial agonist (pAG), a $Ca^{2+}$ influx of >60% relates to a pure agonist (AG). After 5 min incubation, the $Ca^{2+}$ influx is related to an injection of 100 nM of capsaicin and thereby the antagonistic effect of the test compounds detected.

Desensitising agonists and antagonists lead to suppression of the $Ca^{2+}$ influx. The % inhibition is calculated compared to the maximum achievable inhibition with 10 µM of capsaicin. Triple analyses (n=3) are carried out and repeated in at least 3 independent experiments.

Starting from the percentage displacement caused by different concentrations of the compounds to be tested of general formula I, $IC_{50}$ inhibitory concentrations which cause a 50-% displacement of capsaicin were calculated. $K_i$ values for the test substances were obtained by conversion by means of the Cheng-Prusoff equation (Cheng, Prusoff; Biochem. Pharmacol. 22, 3099-3108, 1973).

Method:

Chinese hamster ovary cells (CHO K1 cells, European Collection of Cell Cultures (ECACC) United Kingdom) are stably transfected with the VR1 gene. For functional testing, these cells are plated out on poly-D-lysine-coated black 96-well plates having a clear base (BD Biosciences, Heidelberg, Germany) at a density of 25,000 cells/well. The cells are incubated overnight at 37° C. and 5% $CO_2$ in a culture medium (Ham's F12 nutrient mixture, 10% by volume of FCS (foetal calf serum), 18 µg/ml of L-proline). The next day the cells are incubated with Fluo-4 (Fluo-4 2 µM, 0.01% by volume of Pluronic F127, Molecular Probes in HBSS (Hank's buffered saline solution), Gibco Invitrogen GmbH, Karlsruhe, Germany) for 30 min at 37° C. Subsequently, the plates are washed three times with HBSS buffer and after further incubation for 15 min at RT used for $Ca^{2+}$ measurement in a FLIPR assay. The $Ca^{2+}$-dependent fluorescence is measured before and after the addition of the substances to be tested (λex wavelength=488 nm, λem=540 nm). Quantification is carried out by measuring the highest fluorescence intensity (FC, fluorescence counts) over time.

Pharmacological Data

The affinity of the compounds according to the invention for the vanilloid receptor 1 was determined as described hereinbefore (pharmacological method I or II). The compounds according to the invention display affinity to the VR1/TRPV1 receptor (Table 5).

In Table 5 the abbreviations below have the following meanings: Cap=capsaicin; AG=agonist; pAG=partial agonist; ne=no effect (<10% @5 µM); nd=not determined; The value after the "@" symbol indicates the concentration at which the inhibition (as a percentage) was respectively determined.

TABLE 5

| Exemplary Compound | (f) Ki (human) [nM] Cap |
|---|---|
| EX-01 | 1.4 |
| EX-02 | 28.4 |
| EX-03 | 0.6 |
| EX-04 | pAG (1.0) |
| EX-05 | 7.5 |
| EX-06 | 0.7 |
| EX-07 | AG |
| EX-08 | AG |
| EX-09 | pAG (73.8) |
| EX-10 | pAG (8.8) |
| EX-11 | 53.1 |
| EX-12 | 1.1 |
| EX-13 | 5.2 |
| EX-14 | 0.7 |
| EX-15 | 0.4 |
| EX-16 | 41.9 |
| EX-17 | 0.7 |
| EX-18 | 96.7 |
| EX-19 | 13.8 |
| EX-20 | 0.3 |
| EX-21 | ne |
| EX-22 | ne |
| EX-23 | 4.7 |
| EX-24 | 2.35 |
| EX-25 | pAG (73.1) |
| EX-26 | pAG (10.2) |
| EX-27 | 62.5 |
| EX-28 | 19.4 |
| EX-29 | nd |
| EX-30 | 41%@5 µM |
| EX-31 | 48.8 |
| EX-32 | 60.82225 |
| EX-33 | 24.6 |
| EX-34 | pAG (30.2) |
| EX-35 | 78.4 |
| EX-36 | AG |
| EX-37 | 46%@5 µM |
| EX-38 | 52.6 |
| EX-39 | 17.6 |
| EX-40 | 43.6 |
| EX-41 | 27.5 |
| EX-42 | 103.4 |
| EX-43 | 29.8 |
| EX-44 | 29.9 |
| EX-45 | 9.1 |
| EX-46 | 55%@5 µM |
| EX-47 | 33.3 |
| EX-48 | 31%@5 µM |
| EX-49 | 35 |
| EX-50 | pAG (5.6) |
| EX-51 | pAG (2.9) |
| EX-52 | AG |
| EX-53 | AG |
| EX-54 | 5.9 |
| EX-55 | 12.3 |
| EX-56 | 0.1 |
| EX-57 | 6.6 |
| EX-58 | 2.3 |
| EX-59 | pAG (1.1) |
| EX-60 | pAG (3.2) |
| EX-61 | nd |
| EX-62 | nd |
| EX-63 | nd |
| EX-64 | nd |
| EX-65 | nd |
| EX-66 | nd |
| EX-67 | nd |

TABLE 5-continued

| Exemplary Compound | (f) Ki (human) [nM] Cap |
|---|---|
| EX-68 | nd |
| EX-69 | nd |
| EX-70 | nd |
| EX-71 | nd |

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A substituted compound of general formula (I),

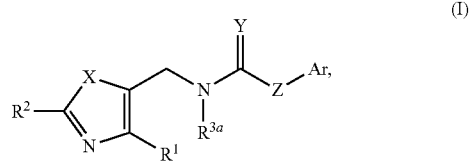

wherein
X represents O or S;
Y represents O, S or N—CN;
Z represents N($R^{3b}$) or C($R^{4a}R^{4b}$);
$R^1$ represents aryl or heteroaryl,
 wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy; $C_{1-4}$-alkoxy-$C_{1-4}$-alkoxy; $C_{1-4}$-alkylS(=O), hydroxy-$C_{1-4}$-alkylS(=O), halo-$C_{1-4}$-alkylS(=O), cyano-$C_{1-4}$-alkylS(=O), $C_{1-4}$-alkoxy-$C_{1-4}$-alkylS(=O), $C_{1-4}$-alkylS(=O)$_2$, hydroxy-$C_{1-4}$-alkylS(=O)$_2$, halo-$C_{1-4}$-alkylS(=O)$_2$, cyano-$C_1$-4-alkylS(=O)$_2$, $C_{1-4}$-alkoxy-$C_{1-4}$-alkylS(=O)$_2$, $H_2N$, ($C_{1-4}$-alkyl)(H)N, (hydroxy-$C_{1-4}$-alkyl)(H)N, (halo-$C_{1-4}$-alkyl)(H)N, (cyano-$C_{1-4}$-alkyl)(H)N, ($C_{1-4}$-alkoxy-$C_{1-4}$-alkyl)(H)N, ($C_{3-6}$-cycloalkyl)(H)N, ($C_{3-7}$-heterocycloalkyl)(H)N, ($C_{1-4}$-alkyl)$_2$N, (hydroxy-$C_{1-4}$-alkyl)($C_{1-4}$-alkyl)N, (halo-$C_{1-4}$-alkyl)($C_{1-4}$-alkyl)N, (cyano-$C_{1-4}$-alkyl)($C_{1-4}$-alkyl)N, ($C_{1-4}$-alkoxy-$C_{1-4}$-alkyl)($C_{1-4}$-alkyl)N, ($C_{3-6}$-cycloalkyl)($C_{1-4}$-alkyl)N, ($C_{3-7}$-heterocycloalkyl)($C_{1-4}$-alkyl)N, (hydroxy-$C_{1-4}$-alkyl)$_2$N, ($C_{3-6}$-cyclo-alkyl)(hydroxy-$C_{1-4}$-alkyl)N, ($C_{3-7}$-heterocycloalkyl)(hydroxy-$C_{1-4}$-alkyl)N,
$R^2$ represents $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, $C_{3-6}$-cycloalkyl or ($C_{3-6}$-cycloalkyl)-$C_{1-4}$-alkyl;
$R^{3a}$ and $R^{3b}$ each independently represent H, $C_{1-4}$-alkyl, hydroxy-$C_{1-4}$-alkyl, halo-$C_{1-4}$-alkyl, cyano-$C_{1-4}$-alkyl or $C_{1-4}$-alkoxy-$C_{1-4}$-alkyl;
$R^{4a}$ and $R^{4b}$ each independently represent H, F, Cl, CN, $C_{1-4}$-alkyl, hydroxy-$C_{1-4}$-alkyl, halo-$C_{1-4}$-alkyl, cyano-$C_{1-4}$-alkyl or $C_{1-4}$-alkoxy-$C_{1-4}$-alkyl; or
$R^{4a}$ and $R^{4b}$ together with the carbon atom connecting them form a $C_{3-6}$-cycloalkyl or a $C_{3-7}$-heterocycloalkyl; and
Ar represents aryl or heteroaryl,
 wherein said aryl or heteroaryl may be condensed with an aromatic or aliphatic ring to form a bicycle,
 and wherein said aryl or heteroaryl and said condensed aromatic or aliphatic ring each independently may be unsubstituted or mono- or independently polysubstituted by one or more substituents, selected from the group consisting of F, Cl, Br, CN, OH, =O, $C_{1-4}$-alkyl, hydroxy-$C_{1-4}$-alkyl, halo-$C_{1-4}$-alkyl, cyano- $C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, hydroxy-$C_{1-4}$-alkoxy-$C_{1-4}$-alkyl, $C_{1-4}$-alkylS(=O), hydroxy-$C_{1-4}$-alkylS(=O), halo-$C_{1-4}$-alkylS(=O), cyano-$C_{1-4}$-alkylS(=O), $C_{1-4}$-alkoxy-$C_{1-4}$-alkylS(=O), $C_{1-4}$-alkylS(=O)$_2$, hydroxy-$C_{1-4}$-alkylS(=O)$_2$, halo-$C_{1-4}$-alkylS(=O)$_2$, cyano-$C_{1-4}$-alkylS(=O)$_2$, $C_{1-4}$-alkoxy-$C_{1-4}$-alkylS(=O)$_2$, $C_{1-4}$-alkylS(=O)$C_{1-4}$-alkyl, hydroxy-$C_{1-4}$-alkylS(=O)$C_{1-4}$-alkyl, $C_{1-4}$-alkylS(=O)$_2C_{1-4}$-alkyl, hydroxy-$C_{1-4}$-alkylS(=O)$_2C_{1-4}$-alkyl, $H_2N$, ($C_{1-4}$-alkyl)(H)N, (hydroxy-$C_{1-4}$-alkyl)(H)N, (halo-$C_{1-4}$-alkyl)(H)N, (cyano-$C_{1-4}$-alkyl)(H)N, ($C_{1-4}$-alkoxy-$C_{1-4}$-alkyl)(H)N, ($C_{3-6}$-cycloalkyl)(H)N, ($C_{3-7}$-heterocycloalkyl)(H)N, ($C_{1-4}$-alkyl)$_2$N, (hydroxy-$C_{1-4}$-alkyl)($C_{1-4}$-alkyl)N, (halo-$C_{1-4}$-alkyl)($C_{1-4}$-alkyl)N, (cyano-$C_{1-4}$-alkyl)($C_{1-4}$-alkyl)N, ($C_{1-4}$-alkoxy-$C_{1-4}$-alkyl)($C_{1-4}$-alkyl)N, ($C_{3-6}$-cycloalkyl)($C_{1-4}$-alkyl)N, ($C_{3-7}$-heterocycloalkyl)($C_{1-4}$-alkyl)N, (hydroxy-$C_{1-4}$-alkyl)$_2$N, ($C_{3-6}$-cycloalkyl)(hydroxy-$C_{1-4}$-alkyl)N, ($C_{3-7}$-heterocycloalkyl)(hydroxy-$C_{1-4}$-alkyl)N, (H)$_2NC_{1-4}$-alkyl, [($C_{1-4}$-alkyl)(H)N]($C_{1-4}$-alkyl), [(hydroxy-$C_{1-4}$-alkyl)(H)N]($C_{1-4}$-alkyl), [(halo-$C_{1-4}$-alkyl)(H)N]($C_{1-4}$-alkyl), [(cyano-$C_{1-4}$-alkyl)(H)N]($C_{1-4}$-alkyl), [($C_{1-4}$-alkoxy-$C_{1-4}$-alkyl)(H)N]($C_{1-4}$-alkyl), [($C_{3-6}$-cycloalkyl)(H)N]($C_{1-4}$-alkyl), [($C_{3-7}$-heterocycloalkyl)-(H)N]($C_{1-4}$-alkyl), [($C_{1-4}$-alkyl)$_2$N]($C_{1-4}$-alkyl), [(hydroxy-$C_{1-4}$-alkyl)($C_{1-4}$-alkyl)N]($C_{1-4}$-alkyl), [(halo-$C_{1-4}$-alkyl)($C_{1-4}$-alkyl)N]($C_{1-4}$-alkyl), [(cyano-$C_{1-4}$-alkyl)($C_{1-4}$-alkyl)N]($C_{1-4}$-alkyl), [($C_{1-4}$-alkoxy-$C_{1-4}$-alkyl)($C_{1-4}$-alkyl)N]($C_{1-4}$-alkyl), [($C_{3-6}$-cycloalkyl)($C_{1-4}$-alkyl)N]($C_{1-4}$-alkyl), [($C_{3-7}$-heterocycloalkyl)($C_{1-4}$-alkyl)N]($C_{1-4}$-alkyl), [(hydroxy-$C_{1-4}$-alkyl)$_2$N]($C_{1-4}$-alkyl), [($C_{3-6}$-cycloalkyl)(hydroxy-$C_{1-4}$-alkyl)N]($C_{1-4}$-alkyl), [($C_{3-7}$-heterocycloalkyl)(hydroxy-$C_{1-4}$-alkyl)N]($C_{1-4}$-alkyl), $H_2NC(=O)$, ($C_{1-4}$-alkyl)(H)NC(=O), (hydroxy-$C_{1-4}$-alkyl)(H)NC(=O), (halo-$C_{1-4}$-alkyl)(H)N—C(=O), (cyano-$C_{1-4}$-alkyl)(H)NC(=O), ($C_{1-4}$-alkoxy-$C_{1-4}$-alkyl)(H)—NC(=O), ($C_{3-6}$-cycloalkyl)(H)NC(=O), ($C_{3-7}$-heterocyclo-alkyl)(H)NC(=O), ($C_{1-4}$-alkyl)$_2$NC(=O), (hydroxy-$C_{1-4}$-alkyl)($C_{1-4}$-alkyl)NC(=O), (halo-$C_{1-4}$-alkyl)($C_{1-4}$-alkyl)NC(=O), (cyano-$C_{1-4}$-alkyl)($C_{1-4}$-alkyl)NC(=O), ($C_{1-4}$-alkoxy-$C_{1-4}$-alkyl)($C_{1-4}$-alkyl)NC(=O), ($C_{3-6}$-cyclo-alkyl)($C_{1-4}$-alkyl)NC(=O), ($C_{3-7}$-heterocycloalkyl)($C_{1-4}$-alkyl)NC(=O), (hydroxy-$C_{1-4}$-alkyl)$_2$NC(=O), ($C_{3-6}$-cycloalkyl)(hydroxy-$C_{1-4}$-alkyl)NC(=O), ($C_{3-7}$-heterocycloalkyl)(hydroxy-$C_{1-4}$-alkyl)NC(=O), $H_2NS(=O)_2$, ($C_{1-4}$-alkyl)(H)NS(=O)$_2$, (hydroxy-$C_{1-4}$-alkyl)(H)NS(=O)$_2$, (halo-$C_{1-4}$-alkyl)(H)NS(=O)$_2$, (cyano-$C_{1-4}$-alkyl)(H)NS(=O)$_2$, ($C_{1-4}$-alkoxy-$C_{1-4}$-alkyl)(H)NS(=O)$_2$, ($C_{3-6}$-cycloalkyl)(H)N S(=O)$_2$, ($C_{3-7}$-heterocycloalkyl)(H)NS(=O)$_2$, ($C_{1-4}$-alkyl)$_2$NS(=O)$_2$, (hydroxy-$C_{1-4}$-alkyl)($C_{1-4}$-alkyl)NS(=O)$_2$, (halo-$C_{1-4}$-alkyl)($C_{1-4}$-alkyl)NS(=O)$_2$, (cyano-$C_{1-4}$-alkyl)($C_{1-4}$-alkyl)NS(=O)$_2$, ($C_{1-4}$-alkoxy-$C_{1-4}$-alkyl)($C_{1-4}$-alkyl)NS(=O)$_2$, ($C_{3-6}$-cycloalkyl)($C_{1-4}$-alkyl)NS(=O)$_2$, ($C_{3-7}$-heterocycloalkyl)($C_{1-4}$-alkyl)NS(=O)$_2$, (hydroxy-$C_{1-4}$-alkyl)$_2$NS(=O)$_2$, ($C_{3-6}$-cyclo-alkyl)(hydroxy-$C_{1-4}$-alkyl)NS(=O)$_2$, ($C_{3-7}$-heterocycloalkyl)(hydroxy-$C_{1-4}$-alkyl)NS(=O)$_2$, $H_2NS(=O)_2N(H)C_{1-4}$-alkyl, ($C_{1-4}$-alkyl)(H)NS(=O)$_2N(H)C_{1-4}$-alkyl, (hydroxy-$C_{1-4}$-alkyl)(H)NS(=O)$_2N(H)C_{1-4}$-alkyl, ($C_{1-4}$-alkyl)$_2$NS(=O)$_2N(H)C_{1-4}$-alkyl, ($C_{1-4}$-alkyl)S(=O)$_2N(H)C_{1-4}$-alkyl, (hydroxy-$C_{1-4}$-alkyl)S(=O)$_2N(H)C_{1-4}$-alkyl, $C_{3-6}$-cycloalkyl, ($C_{3-6}$-cycloalkyl)-$C_{1-4}$-alkyl, ($C_{3-6}$-cycloalkyl)-$C_{1-4}$-alkoxy, $C_{3-7}$-hetero-cycloalkyl, ($C_{3-7}$-heterocycloalkyl)-$C_{1-4}$-alkyl, ($C_{3-7}$-heterocycloalkyl)-$C_1$-4-alkoxy, wherein said $C_{3-6}$-cycloalkyl or $C_{3-7}$-heterocycloalkyl may be unsubstituted or mono- or independently polysubstituted by one or more substituents, selected from H, F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

aryl, heteroaryl, (aryl)$C_{1-4}$-alkyl or (heteroaryl)$C_{1-4}$-alkyl, wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

optionally in the form of a single stereoisomer or a mixture of stereoisomers, in the form of the free compound and/or a physiologically acceptable salt or a solvate thereof.

2. The substituted compound according to claim 1, wherein Y represents O.

3. The substituted compound according to claim 1, wherein $R^{3a}$ represents H.

4. The substituted compound according to claim 1, wherein

Z represents $N(R^{3b})$, wherein $R^{3b}$ represents H; or

Z represents $C(R^{4a}R^{4b})$, wherein $R^{4a}$ represents $CH_3$ and $R^{4b}$ represents H or wherein $R^{4a}$ and $R^{4b}$ each represent H.

5. The substituted compound according to claim 1, wherein $R^2$ represents $CH_3$, $CFH_2$, $CHF_2$, $CF_3$, $CH_2CH_3$, $CH(CH_3)_2$ or $C(CH_3)_3$.

6. The substituted compound according to claim 1, wherein $R^1$ represents

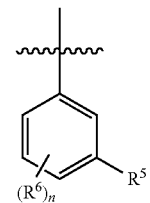

wherein n is 0, 1, 2 or 3;

$R^5$ represents F, Cl, Br, CN, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, and $C_{1-4}$-alkoxy-$C_{1-4}$-alkoxy and each $R^6$ independently is selected from the group consisting of F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, $C_{1-4}$-alkylS(=O), hydroxy-$C_{1-4}$-alkylS(=O), $C_{1-4}$-alkylS(=O)$_2$, hydroxy-$C_{1-4}$-alkylS(=O)$_2$, $H_2N$, ($C_{1-4}$-alkyl)(H)N, (hydroxy-$C_{1-4}$-alkyl)(H)N, ($C_{1-4}$-alkyl)$_2$N, (hydroxy-$C_{1-4}$-alkyl)($C_{1-4}$-alkyl)N, (hydroxy-$C_{1-4}$-alkyl)$_2$N, [($C_{1-4}$-alkyl)(H)N]($C_{1-4}$-alkyl), [(hydroxy-$C_{1-4}$-alkyl)(H)N]($C_{1-4}$-alkyl), [($C_{1-4}$-alkyl)$_2$N]($C_{1-4}$-alkyl), [(hydroxy-$C_{1-4}$-alkyl)($C_{1-4}$-alkyl)N]($C_{1-4}$-alkyl), $H_2NC(=O)$, ($C_{1-4}$-alkyl)(H)NC(=O), (hydroxy-$C_{1-4}$-alkyl)(H)NC(=O), ($C_{1-4}$-alkyl)$_2$NC(=O), (hydroxy-$C_{1-4}$-alkyl)($C_{1-4}$-alkyl)NC(=O), (hydroxy-$C_{1-4}$-alkyl)$_2$NC(=O), $H_2NS(=O)_2$ ($C_{1-4}$-alkyl)(H)NS(=O)$_2$, (hydroxy-$C_{1-4}$-alkyl)(H)NS(=O)$_2$, ($C_{1-4}$-alkyl)$_2$NS(=O)$_2$, (hydroxy-$C_{1-4}$-alkyl)($C_{1-4}$-alkyl)NS(=O)$_2$, (hydroxy-$C_{1-4}$-alkyl)$_2$NS(=O)$_2$, $C_{3-6}$-cycloalkyl, ($C_{3-6}$-cycloalkyl)-$C_{1-4}$-alkyl, ($C_{3-6}$-cycloalkyl)-$C_{1-4}$-alkoxy, $C_{3-7}$-heterocycloalkyl, ($C_{3-7}$-heterocycloalkyl)-$C_{1-4}$-alkyl, ($C_{3-7}$-heterocycloalkyl)-$C_{1-4}$-alkoxy, wherein said $C_{3-6}$-cycloalkyl or $C_{3-7}$-heterocycloalkyl may be unsubstituted or mono- or independently polysubstituted by one or more substituents, selected from H, F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

aryl, heteroaryl, (aryl)$C_{1-4}$-alkyl or (heteroaryl)$C_{1-4}$-alkyl, wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy.

7. The substituted compound according to claim 1, wherein the compound of general formula (I) has general formula (Ia)

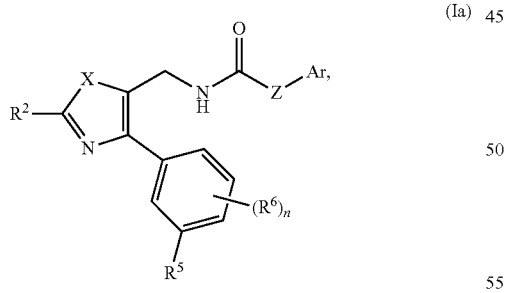

(Ia)

wherein

X represents O or S;

Z represents $N(R^{3b})$ or $C(R^{4a}R^{4b})$;

n is 0, 1 or 2;

$R^2$ represents $CH_3$, $CFH_2$, $CHF_2$, $CF_3$, $CH_2CH_3$, $CH(CH_3)_2$ or $C(CH_3)_3$, $R^{3b}$ independently represent H, $C_{1-4}$-alkyl, hydroxy-$C_{1-4}$-alkyl, halo-$C_{1-4}$-alkyl, cyano-$C_{1-4}$-alkyl or $C_{1-4}$-alkoxy-$C_{1-4}$-alkyl;

$R^{4a}$ and $R^{4b}$ each independently represent H, F, Cl or $C_{1-4}$-alkyl;

$R^5$ represents F, Cl, Br, CN, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, and $C_{1-4}$-alkoxy-$C_{1-4}$-alkoxy and each $R^6$ independently is selected from the group consisting of F, Cl, Br, CN, OH, $C_{1-4}$-alkyl, $CF_3$, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1-4}$-alkoxy, $C_{1-4}$-alkylS(=O), $C_{1-4}$-alkylS(=O)$_2$, $H_2N$, ($C_{1-4}$-alkyl)(H)N, ($C_{1-4}$-alkyl)$_2$N, $H_2NC(=O)$, ($C_{1-4}$-alkyl)(H)NC(=O) and ($C_{1-4}$-alkyl)$_2$NC(=O);

and

Ar represents aryl or heteroaryl, wherein said aryl or heteroaryl may be condensed with an aromatic or aliphatic ring to form a bicycle, and wherein said aryl or heteroaryl and said condensed aromatic or aliphatic ring each independently may be unsubstituted or mono- or independently polysubstituted by one or more substituents, selected from the group consisting of F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy, $C_{1-4}$-alkoxy-$C_{1}$-4-alkoxy, hydroxy-$C_{1-4}$-alkoxy-$C_{1-4}$-alkyl, $C_{1-4}$-alkylS(=O), hydroxy-$C_{1-4}$-alkylS(=O), halo-$C_{1-4}$-alkylS(=O), cyano-$C_{1-4}$-alkylS(=O), $C_{1-4}$-alkoxy-$C_{1-4}$-alkylS(=O), $C_{1-4}$-alkylS(=O)$_2$, hydroxy-$C_{1-4}$-alkylS(=O)$_2$, halo-$C_{1-4}$-alkylS(=O)$_2$, cyano-$C_{1-4}$-alkylS(=O)$_2$, $C_{1-4}$-alkoxy-$C_{1-4}$-alkylS(=O)$_2$, $C_{1-4}$-alkylS(=O)$C_{1-4}$-alkyl, hydroxy-$C_{1-4}$-alkylS(=O)$C_{1-4}$-alkyl, $C_{1-4}$-alkylS(=O)$_2C_{1-4}$-alkyl, hydroxy-$C_{1-4}$-alkylS(=O)$_2C_{1-4}$-alkyl, $H_2N$, ($C_{1-4}$-alkyl)(H)N, (hydroxy-$C_{1-4}$-alkyl)(H)N, (halo-$C_{1-4}$-alkyl)(H)N, (cyano-$C_{1-4}$-alkyl)(H)N, ($C_{1-4}$-alkoxy-$C_{1-4}$-alkyl)(H)N, ($C_{3-6}$-cycloalkyl)(H)N, ($C_{3-7}$-heterocycloalkyl)(H)N, ($C_{1-4}$-alkyl)$_2$N, (hydroxy-$C_{1-4}$-alkyl)($C_{1-4}$-alkyl)N, (halo-$C_{1-4}$-alkyl)($C_{1-4}$-alkyl)N, (cyano-$C_{1-4}$-alkyl)($C_{1-4}$-alkyl)N, ($C_{1-4}$-alkoxy-$C_{1-4}$-alkyl)($C_{1-4}$-alkyl)N, ($C_{3-6}$-cycloalkyl)($C_{1-4}$-alkyl)N, ($C_{3-7}$-heterocycloalkyl)($C_{1-4}$-alkyl)N, (hydroxy-$C_{1-4}$-alkyl)$_2$N, ($C_{3-6}$-cycloalkyl)(hydroxy-$C_{1-4}$-alkyl)N, ($C_{3-7}$-heterocycloalkyl)(hydroxy-$C_{1-4}$-alkyl)N, $(H)_2NC_{1-4}$-alkyl, [($C_{1-4}$-alkyl)(H)N]($C_{1-4}$-alkyl), [(hydroxy-$C_{1-4}$-alkyl)(H)N]($C_{1-4}$-alkyl), [(halo-$C_{1-4}$-alkyl)(H)N]($C_{1-4}$-alkyl), [(cyano-$C_{1-4}$-alkyl)(H)N]($C_{1-4}$-alkyl), [($C_{1-4}$-alkoxy-$C_{1-4}$-alkyl)(H)N]($C_{1-4}$-alkyl), [($C_{3-6}$-cycloalkyl)(H)N]($C_{1-4}$-alkyl), [($C_{3-7}$-heterocycloalkyl)(H)N]($C_{1-4}$-alkyl), [($C_1$-4-alkyl)$_2$N]($C_{1-4}$-alkyl), [(hydroxy-$C_{1-4}$-alkyl)($C_{1-4}$-alkyl)N]($C_{1-4}$-alkyl), [(halo-$C_{1-4}$-alkyl)($C_{1-4}$-alkyl)N]($C_{1-4}$-alkyl), [(cyano-$C_{1-4}$-alkyl)($C_{1-4}$-alkyl)N]($C_{1-4}$-alkyl), [($C_{1-4}$-alkoxy-$C_{1-4}$-alkyl)($C_{1-4}$-alkyl)N]($C_{1-4}$-alkyl), [($C_{3-6}$-cycloalkyl)($C_{1-4}$-alkyl)N]($C_{1-4}$-alkyl), [($C_{3-7}$-heterocycloalkyl)($C_{1-4}$-alkyl)N]($C_{1-4}$-alkyl), [(hydroxy-$C_{1-4}$-alkyl)$_2$N]($C_{1-4}$-alkyl), [($C_{3-6}$-cycloalkyl)(hydroxy-$C_{1-4}$-alkyl)N]($C_{1-4}$-alkyl), [($C_{3-7}$-heterocycloalkyl)(hydroxy-$C_{1-4}$-alkyl)N]($C_{1-4}$-alkyl), $H_2NC(=O)$, ($C_{1-4}$-alkyl)(H)NC(=O), (hydroxy-$C_{1-4}$-alkyl)(H)NC(=O), (halo-$C_{1-4}$-alkyl)(H)NC(=O), (cyano-$C_{1-4}$-alkyl)(H)NC(=O), ($C_{1-4}$-alkoxy-$C_{1-4}$-alkyl)(H)NC(=O), ($C_{3-6}$-cycloalkyl)-(H)NC(=O), ($C_{3-7}$-heterocycloalkyl)(H)NC(=O), ($C_{1-4}$-alkyl)$_2$NC(=O), (hydroxy-$C_{1-4}$-alkyl)($C_{1-4}$-alkyl)NC(=O), (halo-$C_{1-4}$-alkyl)($C_{1-4}$- alkyl)N—C(=O), (cyano-$C_{1-4}$-alkyl)($C_{1-4}$-alkyl)NC(=O), ($C_{1-4}$-alkoxy-$C_{1-4}$-alkyl)($C_{1}$-4-alkyl)NC(=O), ($C_{3-6}$-cycloalkyl)($C_{1-4}$-alkyl)NC(=O), ($C_{3-7}$-heterocyclo-alkyl)($C_{1-4}$-alkyl)NC(=O), (hydroxy-$C_{1-4}$-alkyl)$_2$NC(=O), ($C_{3-6}$-cycloalkyl)(hydroxy-$C_{1-4}$-alkyl)NC(=O), ($C_{3-7}$-heterocycloalkyl)(hydroxy-$C_{1-4}$-alkyl)NC(=O), $H_2NS(=O)_2$, ($C_{1-4}$-alkyl)(H)NS(=O)$_2$, (hydroxy-$C_{1-4}$-alkyl)(H)NS(=O)$_2$, (halo-$C_{1-4}$-alkyl)(H)NS(=O)$_2$, (cyano-$C_{1-4}$-alkyl)(H)N—S(=O)$_2$, ($C_{1-4}$-alkoxy-$C_{1-4}$-alkyl)(H)NS(=O)$_2$, ($C_{3-6}$-cycloalkyl)(H)NS(=O)$_2$, ($C_{3-7}$-heterocycloalkyl)(H)NS(=O)$_2$, ($C_{1-4}$-alkyl)$_2$NS(=O)$_2$, (hydroxy-$C_{1-4}$-alkyl)($C_{1-4}$-alkyl)NS(=O)$_2$, (halo-$C_{1-4}$-alkyl)($C_{1-4}$-alkyl)NS(=O)$_2$, (cyano-$C_{1-4}$-alkyl)($C_{1-4}$-alkyl)NS(=O)$_2$, ($C_{1-4}$-alkoxy-$C_{1-4}$-alkyl)($C_{1-4}$-alkyl)NS(=O)$_2$, ($C_{3-6}$-cycloalkyl)($C_{1-4}$-alkyl)NS(=O)$_2$, ($C_{3-7}$-heterocyclo-alkyl)($C_{1-4}$-alkyl)NS(=O)$_2$, (hydroxy-$C_{1-4}$-alkyl)$_2$NS(=O)$_2$, ($C_{3-6}$-cycloalkyl)(hydroxy-$C_{1-4}$-alkyl)NS(=O)$_2$, ($C_{3-7}$-heterocycloalkyl)(hydroxy-$C_{1-4}$-alkyl)NS(=O)$_2$, $H_2NS(=O)_2N(H)C_{1-4}$-alkyl, ($C_{1-4}$-alkyl)(H)N—S(=O)$_2$N(H)$C_{1-4}$-alkyl, (hydroxy-$C_{1-4}$-alkyl)(H)NS(=O)$_2$N(H)$C_{1-4}$-alkyl, ($C_{1-4}$-alkyl)$_2$NS(=O)$_2$N(H)$C_{1-4}$-alkyl, ($C_{1-4}$-alkyl)S(=O)$_2$N(H)$C_{1-4}$-alkyl, (hydroxy-$C_{1-4}$-alkyl)S(=O)$_2$N(H)$C_{1-4}$-alkyl, $C_{3-6}$-cycloalkyl, ($C_{3-6}$-cyclo-alkyl)-$C_{1-4}$-alkyl, ($C_{3-6}$-cycloalkyl)-$C_{1-4}$-alkoxy, $C_{3-7}$-heterocloalkyl, ($C_{3-7}$-heterocycloalkyl)-$C_{1-4}$-alkyl, ($C_{3-7}$-heterocycloalkyl)-$C_{1-4}$-alkoxy, wherein said $C_{3-6}$-cycloalkyl or $C_{3-7}$-heterocycloalkyl may be unsubstituted or mono- or independently polysubstituted by one or more substituents, selected from H, F, Cl, Br, CN, OH, =O, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

aryl, heteroaryl, (aryl)$C_{1-4}$-alkyl or (heteroaryl)$C_{1-4}$-alkyl, wherein said aryl or heteroaryl may be unsubstituted or mono- or independently polysubstituted by one or more substituents, selected from the group consisting of H, F, Cl, Br, CN, OH, $C_{1-4}$-alkyl, hydroxy-$C_{1-4}$-alkyl, halo-$C_{1-4}$-alkyl, cyano-$C_{1-4}$-alkyl, $C_{1-4}$-alkoxy-$C_{1-4}$-alkyl, hydroxy-$C_{1-4}$-alkoxy, halo-$C_{1-4}$-alkoxy, cyano-$C_{1-4}$-alkoxy and $C_{1-4}$-alkoxy-$C_{1-4}$-alkoxy;

optionally in the form of a single stereoisomer or a mixture of stereoisomers, in the form of the free compound and/or a physiologically acceptable salt or a solvate thereof.

8. The substituted compound according to claim 7, wherein n is 0.

9. The substituted compound according to claim 1, wherein $R^5$ is F, Cl, CN, $CH_3$, $CHF_2$, $CF_3$, $CH_2CH_3$, $OCH_3$, $OCF_3$, $OCHF_2$ or $CH_2OCH_3$.

10. The substituted compound according to claim 1, wherein Ar is selected from phenyl or pyridinyl, wherein said phenyl or pyridinyl may be condensed with an aromatic or aliphatic ring to form a bicycle, and wherein said phenyl or pyridinyl and said condensed aromatic or aliphatic ring each independently may be unsubstituted or mono- or independently polysubstituted by one or more substituents, selected from the group consisting of F, Cl, Br, CN, OH, =O, $C_{1-4}$-alkyl, hydroxy-$C_{1-4}$-alkyl, halo-$C_{1-4}$-alkyl, $C_{1-4}$-alkoxy-$C_{1-4}$-alkyl, hydroxy-$C_{1-4}$-alkoxy, halo-$C_{1-4}$-alkoxy, $C_{1-4}$-alkoxy-$C_{1-4}$-alkoxy, $H_2N$, ($C_{1-4}$-alkyl)(H)N, (hydroxy-$C_{1-4}$-alkyl)(H)N, $H_2NC(=O)$, ($C_{1-4}$-alkyl)(H)NC(=O), (hydroxy-$C_{1-4}$-alkyl)(H)NC(=O), ($C_{1-4}$-alkyl)$_2$NC(=O), (hydroxy-$C_{1-4}$-alkyl)($C_{1-4}$-alkyl)NC(=O) and $C_{3-6}$-cycloalkyl.

11. The substituted compound according to claim 1, wherein Ar is selected from

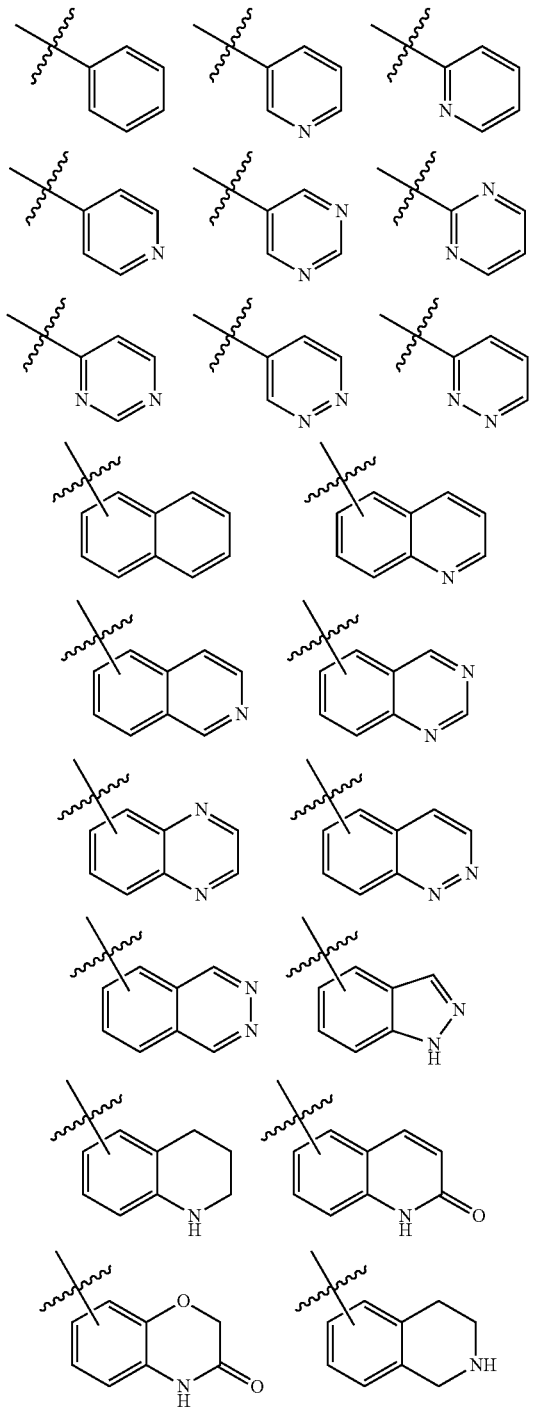

-continued

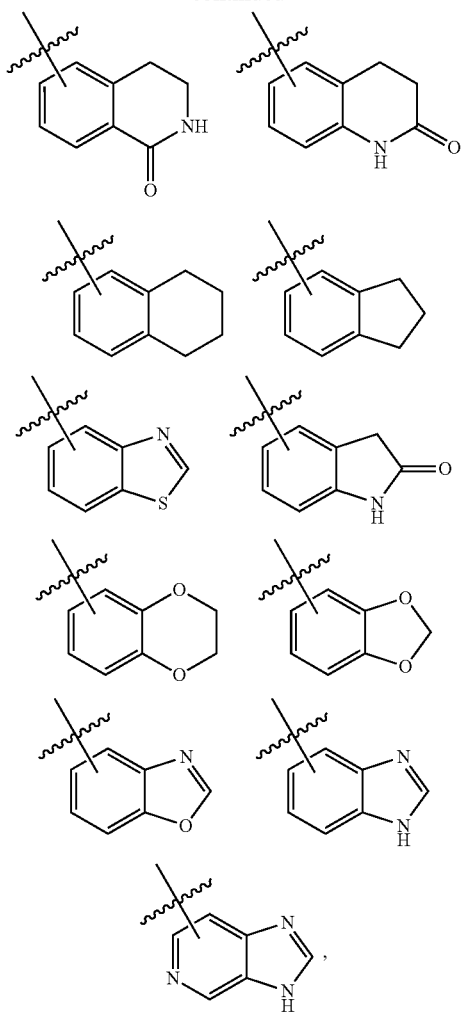

each unsubstituted or mono- or independently polysubstituted by one or more substituents, wherein said substituent(s) are selected from the group consisting of F, Cl, Br, CN, =O, OH, $CH_3$, $CHF_2$, $CF_3$, $CH_2CH_3$, $(CH_2)_2CH_3$, $CH(CH_3)_2$, $(CH_2)_3CH_3$, $CH_2CH(CH_3)_2$, $CH(CH_3)CH_2CH_3$, $C(CH_3)_3$, $OCH_3$, $OCF_3$, $OCHF_2$, $CH_2OCH_3$, $CH_2OCF_3$, $CH_2OH$, $CH_2CH_2OH$, $OCH_2CH_2OH$, $N(H)CH_2CH_2OH$, $N(CH_3)CH_2CH_2OH$, $CH_2OCH_2CH_2OH$, $CH_2N(H)CH_2CH_2OH$, $CH_2N(CH_3)CH_2CH_2OH$, $CH_2CH_2S(=O)_2CH_3$, $CH_2CH_2S(=O)_2N(H)CH_3$, $CH_2N(H)S(=O)_2NH_2$, $CH_2N(H)S(=O)_2CH_3$,

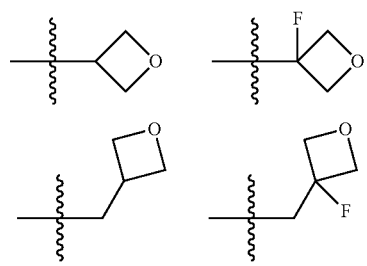

-continued

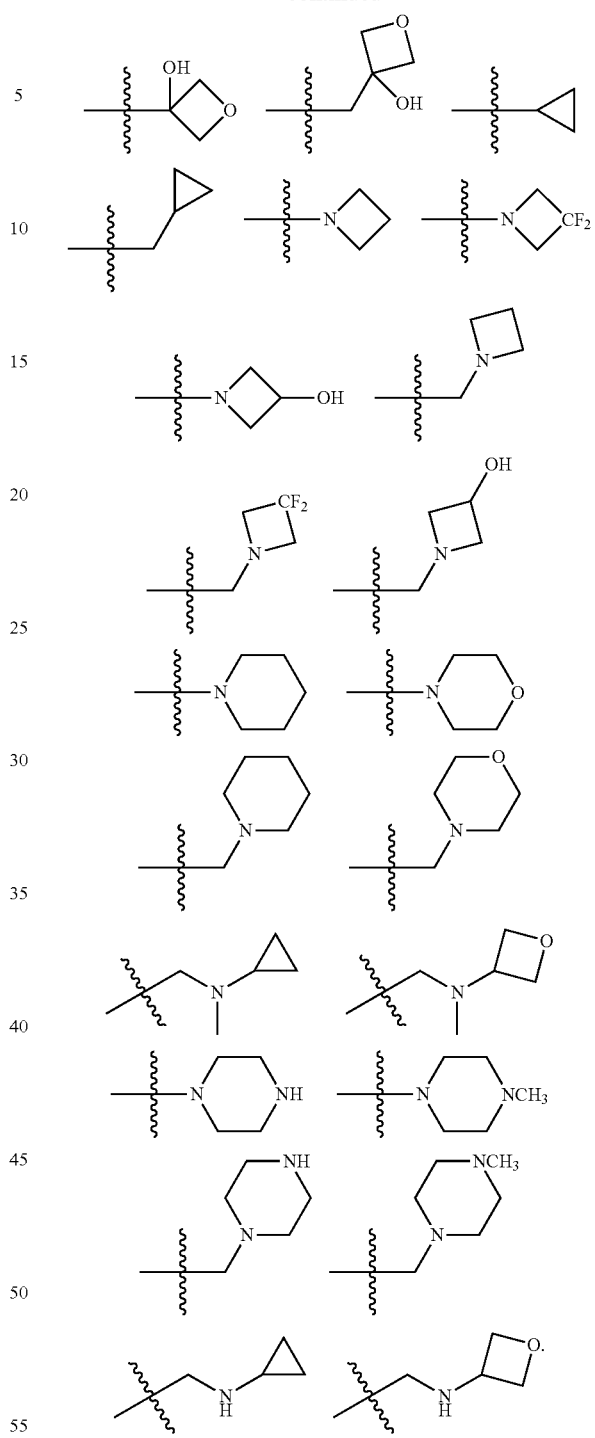

12. The substituted compound according to claim 1, wherein Ar is selected from

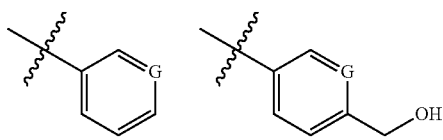

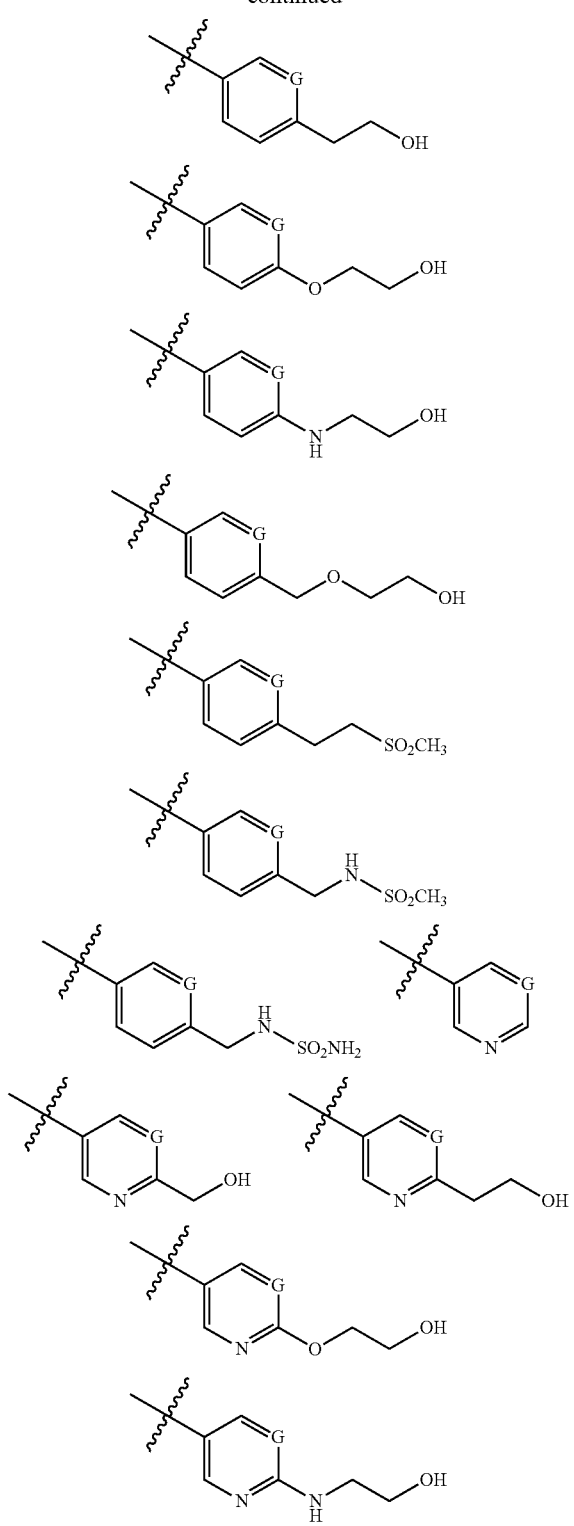

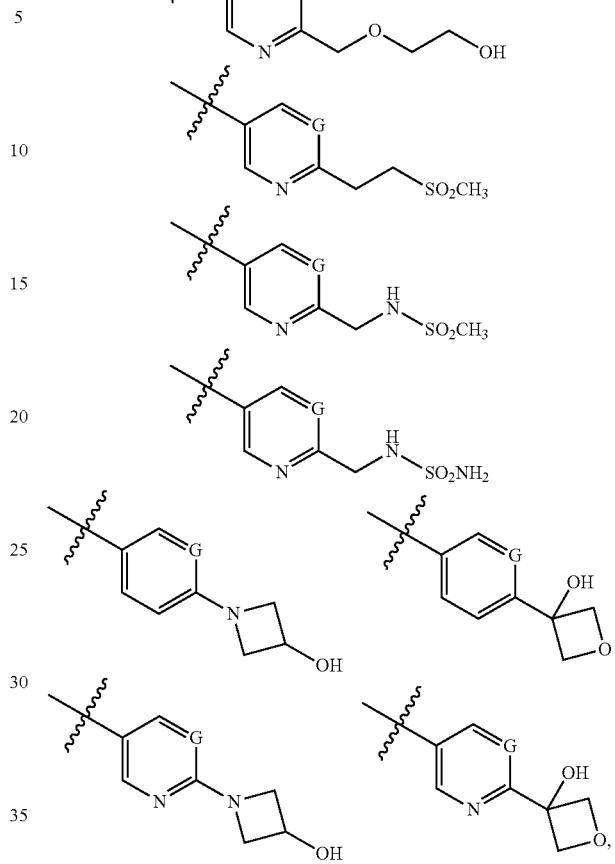

wherein G is CH or CF.

13. A pharmaceutical composition comprising at least one substituted compound according to claim 1.

14. A substituted compound according to claim 1 for use in the treatment and/or prophylaxis of one or more diseases and/or disorders selected from the group consisting of pain.

15. A method of treatment and/or prophylaxis of disorders and/or diseases selected from the group consisting of pain in a mammal comprising administering an effective amount of at least one compound according to claim 1 to the mammal.

16. The substituted compound according to claim 4, wherein Z represents $N(R^{3b})$, wherein $R^{3b}$ represents H.

17. The substituted compound according to claim 5, wherein $R^2$ represents $CF_3$ or $C(CH_3)_3$.

18. The substituted compound according to claim 14, wherein the pain is selected from the group consisting of acute pain, chronic pain, neuropathic pain, visceral pain and joint pain.

19. The method according to claim 15, wherein the pain is selected from the group consisting of acute pain, chronic pain, neuropathic pain, visceral pain and joint pain.

* * * * *